US008691781B2

(12) United States Patent
Tang et al.

(10) Patent No.: US 8,691,781 B2
(45) Date of Patent: Apr. 8, 2014

(54) COMPOSITIONS FOR TREATING RESPIRATORY VIRAL INFECTIONS AND THEIR USE

(75) Inventors: Qingquan Tang, Gaithersburg, MD (US); Patrick Lu, Potomac, MD (US); Martin Woodle, Bethesda, MD (US); Bojian Zheng, Hong Kong (CN)

(73) Assignee: Sirnaomics, Inc., Gaithersburg, MD (US)

( * ) Notice: Subject to any disclaimer, the term of this patent is extended or adjusted under 35 U.S.C. 154(b) by 267 days.

(21) Appl. No.: 11/792,179

(22) PCT Filed: Nov. 4, 2005

(86) PCT No.: PCT/US2005/040048
§ 371 (c)(1),
(2), (4) Date: Jun. 1, 2007

(87) PCT Pub. No.: WO2006/121464
PCT Pub. Date: Nov. 16, 2006

(65) Prior Publication Data
US 2008/0279920 A1   Nov. 13, 2008

Related U.S. Application Data

(63) Continuation-in-part of application No. PCT/US2005/003858, filed on Feb. 7, 2005.

(60) Provisional application No. 60/625,677, filed on Nov. 5, 2004.

(51) Int. Cl.
*A01N 43/04* (2006.01)
*C12Q 1/68* (2006.01)
*C12N 15/58* (2006.01)
*C07H 21/02* (2006.01)
*C07H 21/04* (2006.01)

(52) U.S. Cl.
USPC .............. 514/44; 435/6; 435/91.1; 435/91.31; 435/455; 435/458; 536/23.1; 536/24.32; 536/24.5

(58) Field of Classification Search
USPC ......... 435/6, 91.31, 455, 91.1, 458; 536/23.1, 536/24.5, 24.32, 24.3; 514/44
See application file for complete search history.

(56) References Cited

U.S. PATENT DOCUMENTS

| 7,199,109 | B2 | 4/2007 | Pal et al. | |
| 7,297,786 | B2 * | 11/2007 | McCray et al. | ............... 536/24.5 |
| 2002/0095692 | A1 * | 7/2002 | Thomas et al. | ................... 800/8 |
| 2005/0176024 | A1 | 8/2005 | McSwiggen et al. | |
| 2006/0025366 | A1 * | 2/2006 | MacLachlan et al. | .......... 514/44 |
| 2006/0134787 | A1 | 6/2006 | Zamore et al. | |
| 2007/0197460 | A1 | 8/2007 | de Fougerolles et al. | |

FOREIGN PATENT DOCUMENTS

| WO | WO 01/08703 A1 | 2/2001 |
| WO | WO 01/47496 A1 | 7/2001 |
| WO | WO 03/070918 | * 2/2003 |
| WO | WO 03/040399 A2 | 5/2003 |
| WO | WO 03/070918 | * 8/2003 |
| WO | WO 03/070918 A2 | 8/2003 |
| WO | WO 03/090719 A1 | 11/2003 |
| WO | WO 2004/028471 A2 | 4/2004 |
| WO | WO 2005/076999 A2 | 8/2005 |

OTHER PUBLICATIONS

Barik, Sailen, "Control of nonsegmented negative-strand RNA virus replication by siRNA," Virus Research, vol. 102, 2004, pp. 27-35.
Bitko, Vira, et al, "Phenotypic silencing of cytoplasmic genes using sequence-specific double-stranded short interfering RNA and its application in the reverse genetics of wild type negative-strand RNA viruses" BMC Microbiology, vol. 1, No. 34, Dec. 20, 2001, pp. 1-11.
Bitko, Vira, et al, "Inhibition of respiratory viruses by nasally administered siRNA," Nature Medicine, vol. 11, No. 1, Jan. 2005, pp. 50-55.
Ge, Qing, et al, "RNA interference of influenza virus production by directly targeting mRNA for degradation and indirectly inhibiting all viral RNA transcription," PNAS, vol. 100, No. 5, Mar. 4, 2003, pp. 2718-2723.
Ge, Qing, et al, "Inhibition of influenza virus production in virus-infected mice by RNA interference," PNAS, vol. 101, No. 23, Jun. 8, 2004, pp. 8676-8681.
Ge, Qing, et al, "Use of siRNAs to prevent and treat influenza virus infection," Virus Research, Elsevier, Amsterdam, NL, vol. 102, 2004, pp. 37-42.
Li, Bao-Jian, et al, "Using siRNA in prophylactic and therapeutic regimens against SARS coronavirus in Rhesus macaque," Nature Medicine Advance Online Publication, Aug. 21, 2005, pp. 1-8.
Pickering, Lulu, "Progress in RNA-based therapeutics," Spectrum Drug Discovery and Design, Decision Resources, Inc., Waltham, Massachusetts, Aug. 4, 2005, pp. 6-1 to 6-20.
Xu, Zan, et al, "Potent inhibition of respiratory syncytial virus by combination treatment with 2-5A antisense and ribavirin," Antiviral Research, vol. 61, 2004, pp. 195-206.
Zhang, W., et al, "Inhibition of respiratory syncytial virus replication by vector-derived small interfering RNAs against NS1 protein," Journal of Allergy and Clinical Immunology, vol. 113, No. 2 Supplement, Feb. 2004, pp. S330-S331.
Zhang, Weidong, et al, "Inhibition of respiratory syncytial virus infection with intranasal siRNA nanoparticles targeting the viral NS1 gene," Nature Medicine, vol. 11, No. 1, Jan. 2005, pp. 56-62.

(Continued)

Primary Examiner — Jane Zara
(74) Attorney, Agent, or Firm — Geoffrey M. Karny

(57) ABSTRACT

The invention provides siRNA compositions that interfere with viral replication in respiratory viral infections, including respiratory syncytial virus and avian influenza A, including the H5N1 strain. The invention further provides uses of the siRNA compositions to inhibit expression of viral genes in respiratory virus-infected cells, and to uses in the treatment of respiratory virus infections in a subject. Generally the invention provides polynucleotide that includes a first nucleotide sequence of 15 to 30 bases that targets the genome of a respiratory syncytial virus or an influenza A virus, a complement thereof, a double stranded polynucleotide or a hairpin polynucleotide. Additionally the invention provides vectors, cells and pharmaceutical compositions containing siRNA sequences.

21 Claims, 6 Drawing Sheets

(56) References Cited

OTHER PUBLICATIONS

Zheng, Bo-Jian, et al, "Prophylactic and therapeutic effects of small interfering RNA targeting SARS-coronavirus," Antiviral Therapy, vol. 9, 2004, 365-374.

International Search Report of the International Searching Authority, European Patent Office, on International App. No. PCT/US2005/040048 (WO 06/121464 A3) of Intradigm Corporation for "Compositions for Treating Respiratory Viral Infections and Their Use," Feb. 15, 2007.

Written Opinion of the International Searching Authority, European Patent Office, on International App. No. PCT/US2005/040048 (WO 06/121464 A3) of Intradigm Corporation for "Compositions for Treating Respiratory Viral Infections and Their Use," Feb. 15, 2007.

International Preliminary Report on Patentability of the International Bureau of WIPO on International App. No. PCT/US2005/040048 (WO 06/121464 A3) of Intradigm Corporation for "Compositions for Treating Respiratory Viral Infections and Their Use," May 8, 2007.

De Wolf, Holger, et al., "Effect of Cationic Carriers on the Pharmacokinetics and Tumor Localization of Nucleic Acids after Intravenous Administration," International Journal of Pharmaceutics, 331, 2007, pp. 167-175.

Leng, Qixin, et al., "Highly Branched HK Peptides Are Effective Carriers of siRNA," The Journal of Gene Medicine, 2005, 7, pp. 977-986.

\* cited by examiner

COMPOSITIONS FOR TREATING RESPIRATORY VIRAL INFECTIONS AND THEIR USE

FIELD OF THE INVENTION

The invention relates to siRNA compositions that interfere with viral replication in respiratory viral infections, especially in respiratory syncytial virus and avian influenza A including the H5N1 strain. The invention further relates to uses of the siRNA compositions to inhibit expression of viral genes in respiratory virus-infected cells, and to uses in the treatment of respiratory virus infections in a subject.

BACKGROUND OF THE INVENTION

Respiratory viral infections have been significant threats to human health and lives for centuries. Notorious episodes include infections caused by influenza strains, respiratory syncytial virus, and sever acute respiratory syndrome (SARS). These include the global influenza pandemic of 1918, which killed approximately 20-40 million people worldwide. There have been other influenza pandemics in more recent decades as well. A SARS outbreak in 2002 claimed around 800 lives (2).

Respiratory Syncytial Virus

Respiratory syncytial virus (RSV) infection is the major cause of serious pediatric respiratory tract disease. About two-third of infants are infected with RSV during the first year of life and almost 100% have been infected by age 2. There is currently no specific and effective therapeutic available to treat RSV infection.

Respiratory syncytial virus (RSV) is an enveloped, non-segmented single-strand negative RNA virus (NNR) belonging to the family Paramyxoviradae, in the order mononegaviruses (14, 29). The paramyxoviruses share the following features. 1) They have a single stranded RNA genome that is tightly wrapped with the viral nucleocapsid protein (N)29, 30. 2) Sub-genomic mRNAs are transcribed from the negative genome by RdRP. 3) Virus replication takes place in the cytoplasm of host cells. The details of RSV life cycle from infection to release of progeny virions are well studied (15).

The RSV genome is a negative strand 15.5 kb long, containing the genes 3'-NS1, NS2, N, P, M, SH, G, F, M2, L-5' (see FIG. 1). Of these seven gene products are common to other paramyxoviruses 3, namely, N, P, SH, G, F, and L. Several viral or host factors are involved in the regulation of RNA transcription and replication (20). There are in addition viral cis-acting signals that play regulatory roles in transcription of mRNAs and RNA replication (3).

The incubation period for RSV infection is about 4 to 5 days; it first affects the nasopharynx, then in a few days it reaches the bronchi and bronchioles, with infection confined to the superficial layer of the respiratory epithelium.

Influenza A

Beginning in 1997, a new strain of avian influenza A, H5N1, has appeared. Although confined mostly to fowl, both wild populations and domesticated birds, the virus infects humans apparently only be direct contact with infected birds. In humans infection causes serious disease, leading to severe respiratory illness and death in human beings (3-12). Numerous cases and outbreaks have occurred in various nations of southeast Asia. In view of the ability of the avian virus to infect humans, there is increased risk of mutation to a contagious human variant, risking the emergence of a new influenza pandemic with efficient and sustained human-to-human transmission, and significant mortality.

Since avian flu H5N1 is a newly emerging infectious agent associated with pneumonia and its pathology and mechanism is not very clear, there is no specific and effective treatment for H5N1 avian flu in the human disease cases yet. Currently influenza infections are treated with antivirals, such as the two drugs (in the neuraminidase inhibitors class), oseltamivir (commercially known as Tamiflu) and zanamivir (commercially known as Relenza), or the older M2 inhibitors amantadine and rimantadine.

H5N1 is a subtype of influenza virus type A. As such it is an enveloped, fragmented, negative-single stranded RNA virus, belonging to the family Orthomyxoviridae. During the life cycle of the influenza A virus (including H5N1), the viral genome RNA (vRNA) serves as a template for complementary RNA (cRNA) production, which also serves as the template for messenger RNA (mRNA) production. Each of these three forms of RNA molecules arising during viral replication can all be targeted for siRNA-mediated degradation, using either sense or antisense siRNAs. The influenza A genome, consisting of 8 separate RNA segments containing at least 10 open reading frames (ORFs), serves as template for both viral genome replication and subgenomic or gene-directed mRNA synthesis. FIG. 2 shows a diagram representing the structure of an influenza A virion. Polymerases PB2, PB1 (polymerase basic protein 1 and 2) and PA (polymerase acidic protein) were coded by RNA1, RNA2 and RNA3 respectively. Four viral structural proteins H (hemagglutinin), N (neuraminidase), M1 and M2 (matrix proteins 1 and 2) are respectively coded by RNA segments 4, 6 and 7, while RNA5 codes for NP (nucleocapsid protein) and RNA8 codes for NS1 and NS2 (nonstructural proteins 1 and 2).

RNA Interference

RNA interference (RNAi) is a sequence-specific RNA degradation process that provides a relatively easy and direct way to knockdown, or silence, theoretically any gene (17, 18, 19). In naturally occurring RNA interference, a double stranded RNA is cleaved by an RNase III/helicase protein, Dicer, into small interfering RNA (siRNA) molecules, a dsRNA of 19-23 nucleotides (nt) with 2-nt overhangs at the 3' ends. These siRNAs are incorporated into a multicomponent-ribonuclease called RNA-induced-silencing-complex (RISC). One strand of siRNA remains associated with RISC, and guides the complex towards a cognate RNA that has sequence complementary to the guider ss-siRNA in RISC. This siRNA-directed endonuclease digests the RNA, thereby inactivating it. Recent studies have revealed that the use of chemically synthesized 21-25-nt siRNAs exhibit RNAi effects in mammalian cells 20, and the thermodynamic stability of siRNA hybridization (at terminals or in the middle) plays a central role in determining the molecule's function (21, 22). These and other characteristics of RISC, siRNA molecules and RNAi have been described (23-28).

Application of RNAi in mammalian cells in laboratory or potentially, in therapeutic applications, uses either chemically synthesized siRNAs or endogenously expressed molecules (2, 21). The endogenous siRNA is first expressed as a small hairpin RNAs (shRNAs) by an expression vector (plasmid or virus vector), and then processed by Dicer into siRNAs. It is thought that siRNAs hold great promise to be therapeutics for human diseases especially that caused by viral infections (19, 20, 27-30).

Importantly, it is presently not possible to predict with any degree of confidence which of many possible candidate siRNA sequences potentially targeting a viral genome sequence (e.g., oligonucleotides of about 16-30 base pairs) will in fact exhibit effective siRNA activity. Instead, individual specific candidate siRNA polynucleotide or oligonucleotide sequences must be generated and tested to determine whether the intended interference with expression of a targeted gene has occurred. Accordingly, no routine method exists in the art for designing a siRNA polynucleotide that is, with certainty, capable of specifically altering the expression of a given mRNA.

There remains a significant need for compositions and methods that inhibit expression of viral pathogen genes and their cognate protein products. In particular there is an urgent need for compositions and methods to inhibit expression of pathogenic respiratory viral genes in virus-infected-cells, and for treating a respiratory viral infection in a subject. There further is a need for compositions and methods addressing infection by RSV and avian influenza A, especially the H5N1 strain. There additionally is a need for compositions and methods for treatment that are highly effective, and do not rely on use or modification of known antiviral agents. The present invention addresses these and related needs.

SUMMARY OF THE INVENTION

The present invention provides compositions and methods related to use of RNA interference to inhibit viral infection and replication through disruption of viral RNA molecules of viral pathogens, such as those causing respiratory viral infections including influenza A H5N1 and RSV. These viruses are pathogens causing severe respiratory diseases in humans and other mammals. Inhibition of viral replication will combat the viral infection in cultured cells and in subjects infected with the virus, including relief from its symptoms.

In a first aspect, the invention provides an isolated polynucleotide whose length can be any number of nucleotides that is 200 or fewer, and 15 or greater. The polynucleotide includes a first nucleotide sequence that targets the genome of a respiratory syncytial virus or an influenza A virus. In the polynucleotide any T (thymidine) or any U (uridine) may optionally be substituted by the other. Additionally, in the polynucleotide the first nucleotide sequence consists of a) a sequence whose length is any number of nucleotides from 15 to 30, or b) a complement of a sequence given in a). Such a polynucleotide may be termed a linear polynucleotide herein.

In a related aspect of the invention, the polynucleotide described above further includes a second nucleotide sequence separated from the first nucleotide sequence by a loop sequence, such that the second nucleotide sequence
   a) has substantially the same length as the first nucleotide sequence, and
   b) is substantially complementary to the first nucleotide sequence.

In this latter structure, termed a hairpin polynucleotide, the first nucleotide sequence hybridizes with the second nucleotide sequence to form a hairpin whose complementary sequences are linked by the loop sequence.

In many embodiments of the linear polynucleotide and of the hairpin polynucleotide the first nucleotide sequence is either
   a) a sequence chosen from SEQ ID NOS:1-263,
   b) a targeting sequence longer than the sequence given in item a), wherein the targeting sequence targets the genome of a respiratory virus and includes a sequence chosen from SEQ ID NOS:1-263,
   c) a fragment of a sequence chosen from SEQ ID NOS:1-263 wherein the fragment consists of a sequence of contiguous bases at least 15 nucleotides in length and at most one base shorter than the chosen sequence,
   d) a sequence wherein up to 5 nucleotides differ from a sequence chosen from SEQ ID NOS:1-263, or
   e) a complement of any sequence given in a) to d).

In various embodiments of a linear polynucleotide or a hairpin polynucleotide the length of the first nucleotide sequence is any number of nucleotides from 21 to 25. In many embodiments a linear polynucleotide or a hairpin polynucleotide consists of a sequence chosen from SEQ ID NOS:1-263, and optionally includes a dinucleotide overhang bound to the 3' of the chosen sequence. In yet additional embodiments of a linear polynucleotide or a hairpin polynucleotide the dinucleotide sequence at the 3' end of the first nucleotide sequence is TT, TU, UT, or UU and includes either ribonucleotides or deoxyribonucleotides or both. In various further embodiments a linear or hairpin polynucleotide may be a DNA, or it may be an RNA, or it may be composed of both deoxyribonucleotides and ribonucleotides.

In an additional aspect the invention provides a double stranded polynucleotide that includes a first polynucleotide strand described in claim 1 and a second polynucleotide strand that is complementary to at least the first nucleotide sequence of the first strand and is hybridized thereto to form a double stranded composition. These polynucleotide structures may also be termed linear polynucleotides.

In still a further aspect the invention provides a combination that includes two or more targeting polynucleotides described in claim 1, claim 2, or both, such that each polynucleotide of the combination targets a different sequence in the genome of the target virus.

Because of the high degree of similarity or identity to the respiratory viral pathogen target, and not wishing to be bound by theory, it is believed that upon introduction within a virally infected cell the polynucleotide induces RNA interference, leading to digestion of the pathogen genomic RNA, complementary RNA, and messenger RNA. In particular, in important embodiments of these aspects of the invention it is believed that the first nucleotide sequence or its complement in these polynucleotides forms an RNA Induced Silencing Complex (RISC) that introduces the polynucleotide siRNA sequence to the pathogen genomic RNA sequence, thereby promoting cleavage of the pathogen genomic RNA.

In additional aspects the invention provides a vector that harbors a sequence given by a linear polynucleotide or a hairpin polynucleotide of the invention. In various embodiments any of these vectors may be a plasmid, a recombinant virus, a transposon, or a minichromosome. Still additional aspects provide cells transfected by one or more linear polynucleotides of the invention, or by one or more hairpin polynucleotides of the invention.

In still further aspects the invention provides a pharmaceutical composition that contains one or more linear polynucleotides or hairpin polynucleotides, or a mixture thereof, wherein each polynucleotide targets a different sequence in the genome of the target virus, and a pharmaceutically acceptable carrier.

In yet an additional aspect the invention provides a pharmaceutical composition containing one or more vectors harboring a linear polynucleotide, or a vector harboring a hairpin polynucleotide, or a mixture thereof, wherein each vector harbors a polynucleotide targeting a different sequence in the genome of the target virus, and a pharmaceutically acceptable carrier.

In various embodiments of the pharmaceutical compositions, the carrier includes a synthetic cationic polymer, a liposome, dextrose, a surfactant, or a combination of any two or more of them.

In still a further aspect the invention provides a method of synthesizing a linear polynucleotide or a hairpin polynucleotide having a sequence that targets the genome of a respiratory syncytial virus or an influenza A virus. The method includes the steps of
   a) providing a nucleotide reagent including a live reactive end and corresponding to the nucleotide at a first end of the sequence;
   b) adding a further nucleotide reagent including a live reactive end and corresponding to a successive position of the sequence to react with the live reactive end from the preceding step and increase the length of the growing polynucleotide sequence by one nucleotide, and removing undesired products and excess reagent; and
   c) repeating step b) until the nucleotide reagent corresponding to the nucleotide at a second end of the sequence has been added;
   thereby providing the completed polynucleotide.

In still an additional aspect the invention provides methods for transfecting a cell with an RNA inhibitor wherein the method includes contacting the cell with a composition containing one or more linear polynucleotides, or one or more hairpin polynucleotides. In many embodiments the cell so transfected includes a respiratory virus that is targeted by the one or more polynucleotides.

In yet an additional aspect the invention provides a method of inhibiting replication of a respiratory virus in a cell infected with the virus that includes contacting the cell with a composition containing one or more linear polynucleotides, or one or more hairpin polynucleotides, wherein the one or more polynucleotides target the virus.

In still a further aspect the invention provides a use of a linear polynucleotide that targets a respiratory virus, or of a mixture of two or more of them, or the use of a hairpin polynucleotide targeting a respiratory virus, or of a mixture of two or more of them, in the manufacture of a pharmaceutical composition effective to treat an infection due to the respiratory virus in a subject. In various embodiments of the use, the subject is a human.

In yet an additional aspect the invention provides a method of treating an infection due to a respiratory virus in a subject. The method includes administering an effective dose of a linear polynucleotide targeting the respiratory virus, or of a mixture of two or more of them, or an effective dose of a hairpin polynucleotide targeting the respiratory virus, or a mixture of two or more of them, to the subject. In various embodiments of this method, the subject is a human. In additional embodiments both a linear polynucleotide and a hairpin polynucleotide is administered to the subject.

BRIEF DESCRIPTION OF THE FIGURES

Figures 1, 2:
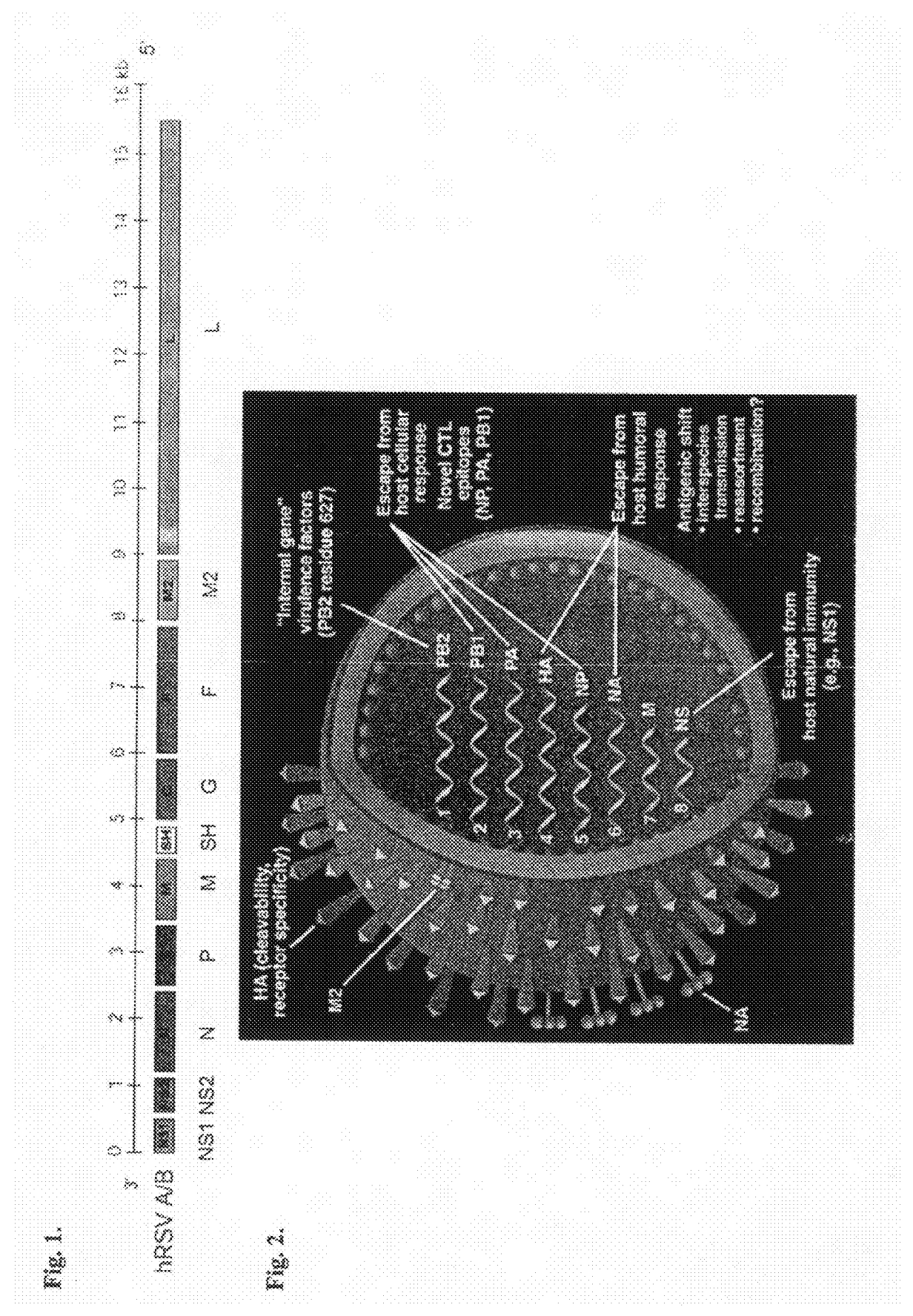

FIG. 1. Schematic representation of the human respiratory syncytial virus (hRSV, RSV) (−)ssRNA genome. Based on GenBank accession no. NC_001781.

FIG. 2. Schematic representation of influenza type A viral structure. The drawing shows the eight segments of the viral genome incorporated within the virion.

DETAILED DESCRIPTION OF THE INVENTION

Figure 3:
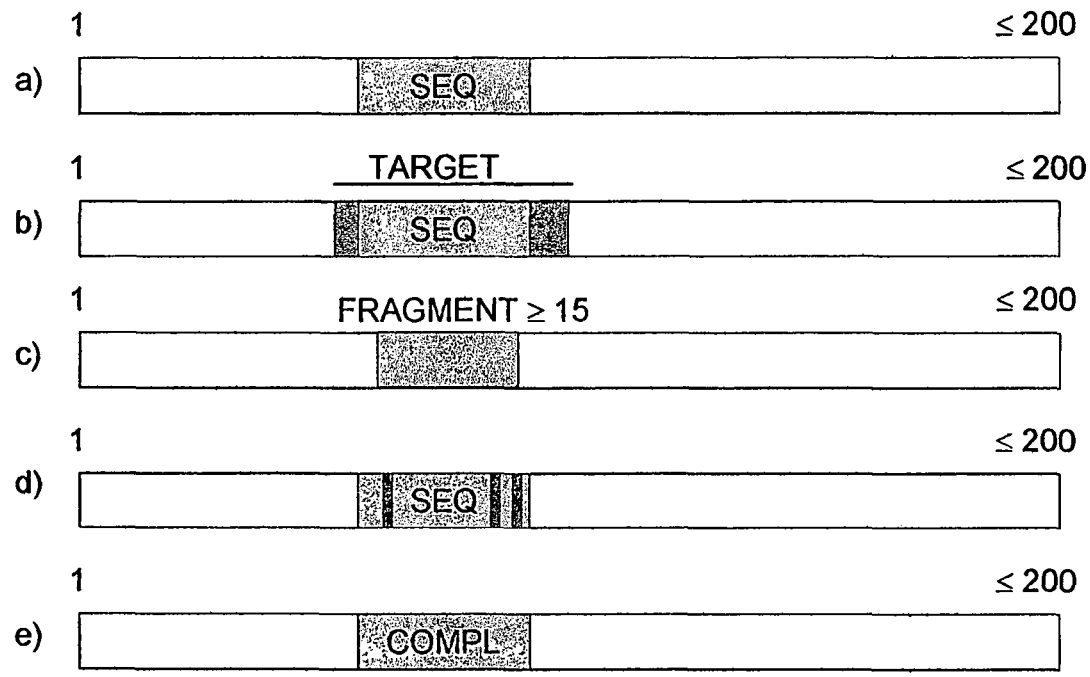
FIG. 3. Schematic representation of various embodiments of the polynucleotides of the invention. Panel A, embodiments of a linear polynucleotide. The length is 200 nucleotides or less, and 15 nucleotides or greater. In b), a specified targeting sequence is contained within a larger targeting sequence. In d) the darker vertical bars diagrammatically represent substituted nucleotides. Panel B, an embodiment of a hairpin polynucleotide of overall length 200 nucleotides or less.
Figure 3:
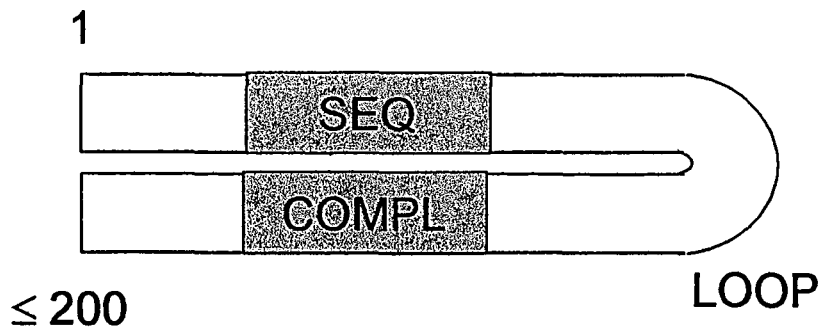

All patents, patent application publications, and patent applications identified herein are incorporated by reference in their entireties, as if appearing herein verbatim. All technical publications identified herein are also incorporated by reference.

In the present description, the articles "a", "an", and "the" relate equivalently to a meaning as singular or as plural. The particular sense for these articles is apparent from the context in which they are used.

As used herein the term "target" sequence and similar terms and phrases relate to a nucleotide sequence that occurs in the genome of a pathogen against which a polynucleotide of the invention is directed. A polynucleotide targets a pathogen sequence either a) by including a sequence that is homologous or identical to a particular subsequence (termed a target sequence) contained within the genome of the pathogen, or b) by including a sequence whose complement is homologous or identical to the target sequence. It is believed that any polynucleotide so targeting a pathogen sequence has the ability to hybridize with the target sequence according to the RNA interference phenomenon, thereby initiating RNA interference.

As used herein; the terms "complement", "complementarity", and similar terms and phrases relate to two sequences whose bases form complementary base pairs, base by base, as conventionally understood by workers of skill in fields such as biochemistry, molecular biology, genomics, and similar fields related to the field of the invention.

As used herein, a first sequence or subsequence is "identical", or has "100% identity", or is described by a term or phrase conveying the notion of 100% identity, to a second sequence or subsequence when the first sequence or subsequence has the same base as the second sequence or subsequence at every position of the sequence or subsequence. In determining identity, any particular base position containing a T (thymidine) or any derivative thereof, or a U (uridine) or any derivative thereof, are equivalent to each other, and so considered identical.

As described herein, a sequence of a targeting polynucleotide, or its complement, may be completely identical to the target sequence, or it may include mismatched bases at particular positions in the sequence. Incorporation of mismatches is described fully herein. Without wishing to be bound by theory, it is believed that incorporation of mismatches provides an intended degree of stability of hybridization under physiological conditions to optimize the RNA interference phenomenon for the particular target sequence in question. The extent of identity determines the percent of the positions in the two sequences whose bases are identical to each other. The "percentage of sequence identity" is calculated by comparing two optimally aligned sequences over that region of comparison, determining the number of positions at which the identical nucleic acid base (e.g., A, T or U, C, G, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. Sequences that are less than 100% identical to each other are "similar" or "homologous" to each other; the degree of homology or the percent similarity are synonymous terms relating to the percent of identity between two sequences or subsequences as determined in the following paragraphs. For example, two sequences displaying at least 60% identity, or preferably at least 65% identity, or preferably at least 70% identity, or preferably at least 75% identity, or preferably at least 80% identity, or more preferably at least 85% identity, or more preferably at least 90% identity, or still more preferably at least 95% identity, to each other are "similar" or "homologous" to each other. Alternatively, with reference to the oligonucleotide sequence of an siRNA molecule, two sequences that differ by 5 or fewer bases, or by 4 or fewer bases, or by 3 or fewer bases, or by two or fewer bases, or by one base, are termed "similar" or "homologous" to each other.

"Identity," as known in the art, is a relationship between two or more polypeptide sequences or two or more polynucleotide sequences, as determined by, comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (Computational Molecular Biology, Lesk. A. M., ed., Oxford University Press, New York, 1988; Biocomputing: Informatics and Genome Projects, Smith, D. W., ed., Academic Press, New York, 1993; Computer Analysis of Sequence Data, Part I. Griffin, A. M., and Griffin, H. G., eds. Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press. New York, 1991; and Carillo, H., and Lipman, D., SIAM J. Applied Math. (1988) 48: 1073. Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devercux, J., et al. (1984) Nucleic Acids Research 12(1): 387), BLASTP, BLASTN, and FASTA (Atschul, S. F. et al. (1990) J. Molec. Biol. 215: 403-410. The BLAST X program is publicly available from NCBI and other sources (BLAST Manual, Altschul, S., et al., NCBI NLM NIH Bethesda, Md. 20894; Altschul, S., et al. (1990) J. Mol. Biol. 215: 403-410. The well known Smith Waterman algorithm may also be used to determine identity.

Parameters for sequence comparison include the following: Algorithm: Needleman and Wunsch, J. Mol. Biol. 48: 443-453 (1970).

Comparison matrix: BLOSSUM62 from Hentikoff and Hentikoff, (1992) Proc. Natl. Acad. Sci. USA. 89:10915-10919.

As used herein, the term "isolated", and similar words, when used to describe a nucleic acid, a polynucleotide, or an oligonucleotide relate to being removed from its natural or original state. Thus, if it occurs in nature, it has been removed from its original environment. If it has been prepared synthetically, it has been removed from an original product mixture resulting from the synthesis. For example, a naturally occurring polynucleotide naturally present in a living organism in its natural state is not "isolated," but the same polynucleotide separated from materials with which it coexists in its natural state is "isolated", as the term is employed herein. Generally, removal of at least one significant coexisting material constitutes "isolating" a nucleic acid, a polynucleotide, an oligonucleotide. In many cases several, many, or most coexisting materials may be removed to isolate the nucleic acid, a polynucleotide, an oligonucleotides, a protein, a polypeptide, or an oligopeptide. By way of nonlimiting example, with respect to polynucleotides, the term "isolated" may mean that it is separated from the chromosome and cell in which it naturally occurs. Further by way of example, "isolating" a protein or polypeptide may mean separating it from another component in a cell lysate or cell homogenate.

A nucleic acid, a polynucleotide, or an oligonucleotide that is the product of an in vitro synthetic process or a chemical synthetic process is essentially isolated as the result of the synthetic process. In important embodiments such synthetic products are treated to remove reagents and precursors used, and side products produced, by the process.

Similarly, the polynucleotides and polypeptides may occur in a composition, such as a formulation, a composition for introduction of polynucleotides into cells, compositions or solutions for chemical or enzymatic reactions, for instance, which are not naturally occurring compositions, and, therein remain isolated polynucleotides or polypeptides within the meaning of that term as it is employed herein.

As used herein and in the claims, a "nucleic acid" or "polynucleotide", and similar terms based on these, refer to polymers composed of naturally occurring nucleotides as well as to polymers composed of synthetic or modified nucleotides. Thus, as used herein, a polynucleotide that is a RNA, or a polynucleotide that is a DNA may include naturally occurring moieties such as the naturally occurring bases and ribose or deoxyribose rings, or they may be composed of synthetic or modified moieties as described in the following. The linkages between nucleotides is commonly the 3'-5' phosphate linkage, which may be a natural phosphodiester linkage, a phosphothioester linkage, and still other synthetic linkages. Examples of modified backbones include, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates. Additional linkages include phosphotriester, siloxane, carbonate, carboxymethylester, acetamidate, carbamate, thioether, bridged phosphoramidate, bridged methylene phosphonate, bridged phosphorothioate and sulfone internucleotide linkages. Other polymeric linkages include 2'-5' linked analogs of these. See U.S. Pat. Nos. 6,503,754 and 6,506,735 and references cited therein, incorporated herein by reference.

Nucleic acids and polynucleotides may be 20 or more nucleotides in length, or 30 or more nucleotides in length, or 50 or more nucleotides in length, or 100 or more, or 1000 or more, or tens of thousands or more, or hundreds of thousands or more, in length. An siRNA may be a polynucleotide as defined herein. As used herein, "oligonucleotides" and similar terms based on this relate to short polymers composed of naturally occurring nucleotides as well as to polymers composed of synthetic or modified nucleotides, as described in the immediately preceding paragraph. Oligonucleotides may be 10 or more nucleotides in length, or 15, or 16, or 17, or 18, or 19, or 20 or more nucleotides in length, or 21, or 22, or 23, or 24 or more nucleotides in length, or 25, or 26, or 27, or 28 or 29, or 30 or more nucleotides in length, 35 or more, 40 or more, 45 or more, up to about 50, nucleotides in length. An oligonucleotide that is an siRNA may have any number of nucleotides between 15 and 30 nucleotides. In many embodiments an siRNA may have any number of nucleotides between 21 and 25 nucleotides.

It is understood from the definitions just provided that, because of the overlap in size ranges the term "polynucleotide" and "oligonucleotide" may be used synonymously herein to refer to an siRNA of the invention.

As used herein and in the claims "nucleotide sequence", "oligonucleotide sequence" or "polynucleotide sequence", and similar terms, relate interchangeably both to the sequence of bases that an oligonucleotide or polynucleotide has, as well as to the oligonucleotide or polynucleotide structure possessing the sequence. A nucleotide sequence or a polynucleotide sequence furthermore relates to any natural or synthetic polynucleotide or oligonucleotide in which the sequence of bases is defined by description or recitation of a particular sequence of letters designating bases as conventionally employed in the field.

The bases in oligonucleotides and polynucleotides may be "unmodified" or "natural" bases include the purine bases adenine (A) and guanine (G), and the pyrimidine bases thymine (T), cytosine (C) and uracil (U). In addition they may be bases with modifications or substitutions. As used herein, nonlimiting examples of modified bases include other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-fluoro-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine (1H-pyrimido[5,4-b][1,4]benzoxazin-2(3H)-one), phenothiazine cytidine (1-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo [2,3-d]pyrimidin-2-one). Modified bases may also include those in which the purine or pyrimidine base is replaced with other heterocycles, for example 7-deaza-adenine, 7-deazaguanosine, 2-aminopyridine and 2-pyridone. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition (1991) 30, 613, and those disclosed by Sanghvi, Y. S., Chapter 15, Antisense Research and Applications, pages 289-302, Crooke, S. T. and Lebleu, B., ed., CRC Press, 1993. Certain of these bases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi, Y. S., Crooke, S. T. and Lebleu, B., eds., Antisense Research and Applications, CRC Press, Boca Raton, 1993, pp. 276-278) and are presently preferred base substitutions, even more particularly when combined with 2'-O-methoxyethyl sugar modifications. See U.S. Pat. Nos. 6,503,754 and 6,506,735 and references cited therein, incorporated herein by reference. Use of any modified base is equivalent to use of a naturally occurring base having the same base-pairing properties, as understood by a worker of skill in the art.

As used herein and in the claims, the term "complementary" and similar words based on this, relate to the ability of a first nucleic acid base in one strand of a nucleic acid, polynucleotide or oligonucleotide to interact specifically only with a particular second nucleic acid base in a second strand of a nucleic acid, polynucleotide or oligonucleotide. By way of nonlimiting example, if the naturally occurring bases are considered, A and T or U interact with each other, and G and C interact with each other. As employed in this invention and in the claims, "complementary" is intended to signify "fully complementary", namely, that when two polynucleotide strands are aligned with each other, there will be at least a portion of the strands in which each base in a sequence of contiguous bases in one strand is complementary to an interacting base in a sequence of contiguous bases of the same length on the opposing strand.

As used herein, "hybridize", "hybridization" and similar words relate to a process of forming a nucleic acid, polynucleotide, or oligonucleotide duplex by causing strands with complementary sequences to interact with each other. The interaction occurs by virtue of complementary bases on each of the strands specifically interacting to form a pair. The ability of strands to hybridize to each other depends on a variety of conditions, as set forth below. Nucleic acid strands hybridize with each other when a sufficient number of corresponding positions in each strand are occupied by nucleotides that can interact with each other. It is understood by workers of skill in the field of the present invention, including by way of nonlimiting example molecular biologists and cell biologists, that the sequences of strands forming a duplex need not be 100% complementary to each other to be specifically hybridizable.

As used herein "fragment" and similar words based on this, relate to portions of a nucleic acid, polynucleotide or oligonucleotide shorter than the full sequence of a reference. The sequence of bases in a fragment is unaltered from the sequence of the corresponding portion of the molecule from which it arose; there are no insertions or deletions in a fragment in comparison with the corresponding portion of the molecule from which it arose. As contemplated herein, a fragment of a nucleic acid or polynucleotide, such as an oligonucleotide, is 15 or more bases in length, or 16 or more, 17 or more, 18 or more, or 19 or more, or 20 or more, or 21 or more, or 22 or more, or 23 or more, or 24 or more, or 25 or more, or 26 or more, or 27 or more, or 28 or more, or 29 or more, 30 or more, 50 or more, 75 or more, 100 or more bases in length, up to a length that is one base shorter than the full length sequence. Oligonucleotides may be chemically synthesized and may be used as siRNAs, PCR primers, or probes.

Detection and Labeling. A targeting polynucleotide, such as a polynucleotide that includes an siRNA sequence, as well as a viral polynucleotide target, may be detected in many ways. Detecting may include any one or more processes that result in the ability to observe the presence and or the amount of a targeting polynucleotide. In one embodiment a sample nucleic acid containing a targeting polynucleotide or a viral target may be detected prior to expansion. In an alternative embodiment a targeting polynucleotide in a sample may be expanded to provide an expanded targeting polynucleotide, or an expanded viral target, and the expanded polynucleotide is detected or quantitated. Physical, chemical or biological methods may be used to detect and quantitate a targeting polynucleotide. Physical methods include, by way of nonlimiting example, surface plasmon resonance (SPR) detection such as binding a probe to a surface and using SPR to detect binding of a targeting polynucleotide to the immobilized probe, or having a probe in a chromatographic medium and detecting binding of a targeting polynucleotide in the chromatographic medium. Physical methods further include a gel electrophoresis or capillary electrophoresis format in which targeting polynucleotides are resolved from other polynucleotides, and the resolved targeting polynucleotides are detected. Chemical methods include polymerase chain reaction (PCR) methods, and hybridization methods generally in which a targeting polynucleotide hybridizes to a probe. Biological methods include causing a targeting polynucleotide or a target polynucleotide to exert a biological effect on a cell, and detecting the effect. The present invention discloses examples of biological effects which may be used as a biological assay. These include enumeration of virions by particle counting, plaque assays, evaluation of cytopathic effects on infected cells, and the like. In many embodiments, the polynucleotides may be labeled as described below to assist in detection and quantitation. For example, in embodiments not including expansion, a sample nucleic acid may be labeled by chemical or enzymatic addition of a labeled moiety such as a labeled nucleotide or a labeled oligonucleotide linker.

Expanded polynucleotides may be detected and/or quantitated directly. For example, an expanded polynucleotide may be subjected to electrophoresis in a gel that resolves by size, and stained with a dye that reveals its presence and amount. Alternatively an expanded targeting polynucleotide may be detected upon exposure to a probe nucleic acid under hybridizing conditions (see below) and binding by hybridization is detected and/or quantitated. Detection is accomplished in any way that permits determining that a targeting polynucleotide has bound to the probe. This can be achieved by detecting the change in a physical property of the probe brought about by hybridizing a fragment. A nonlimiting example of such a physical detection method is SPR.

An alternative way of accomplishing detection is to use a labeled form of the expanded polynucleotide, and to detect the bound label. A label may be a radioisotopic label, such as 125I, 35S, 32P, 14C, or 3H, for example, that is detectable by its radioactivity. Alternatively, a label may be selected such that it can be detected using a spectroscopic method, for example by fluorescence, phosphorescence, or chemiluminescence. Thus a label that fluoresces, or that phosphoresces, or that induces a chemiluminescent reaction, may be employed. A label may still further be a ligand in a specific ligand-receptor pair; the presence of the ligand is then detected by the secondary binding of the specific receptor, which commonly is itself labeled for detection.

Interfering RNA

According to the invention, gene expression of respiratory viral targets is attenuated by RNA interference. Expression products of a viral gene are targeted by specific double stranded siRNA nucleotide sequences that are complementary to at least a segment of the viral target that contains any number of nucleotides between 15 and 30, or in many cases, contains anywhere between 21 and 25 nucleotides. The target may occur in the 5' untranslated (UT) region, in a coding sequence, or in the 3' UT region. See, e.g., PCT applications WO00/44895, WO99/32619, WO01/75164, WO01/92513, WO 01/29058, WO01/89304, WO02/16620, and WO02/29858, each incorporated by reference herein in their entirety.

According to the methods of the present invention, respiratory viral gene expression, and thereby respiratory viral replication, is suppressed using siRNA. A targeting polynucleotide according to the invention includes an siRNA oligonucleotide. Such an siRNA can also be prepared by chemical synthesis of nucleotide sequences identical or similar to a viral sequence. See, e.g., Tuschl, Zamore, Lehmann, Bartel and Sharp (1999), Genes & Dev. 13: 3191-3197, incorporated herein by reference in its entirety. Alternatively, a targeting siRNA can be obtained using a targeting polynucleotide sequence, for example, by digesting a respiratory viral ribopolynucleotide sequence in a cell-free system, such as but not limited to a Drosophila extract, or by transcription of recombinant double stranded viral cRNA.

Efficient silencing is generally observed with siRNA duplexes composed of a 16-30 nt sense strand and a 16-30 nt antisense strand of the same length. In many embodiments each strand of an siRNA paired duplex has in addition a 2-nt overhang at the 3' end. The sequence of the 2-nt 3' overhang makes an additional small contribution to the specificity of siRNA target recognition. In one embodiment, the nucleotides in the 3' overhang are ribonucleotides. In an alternative embodiment, the nucleotides in the 3' overhang are deoxyribonucleotides. Use of 3' deoxynucleotides provides enhanced intracellular stability.

A recombinant expression vector of the invention, when introduced within a cell, is processed to provide an RNA that includes an siRNA sequence targeting a respiratory virus. Such a vector is a DNA molecule cloned into an expression vector comprising operatively-linked regulatory sequences flanking the viral targeting sequence in a manner that allows for expression. From the vector, an RNA molecule that is antisense to viral RNA is transcribed by a first promoter (e.g., a promoter sequence 3' of the cloned DNA) and an RNA molecule that is the sense strand for the viral RNA target is transcribed by a second promoter (e.g., a promoter sequence 5' of the cloned DNA). The sense and antisense strands then hybridize in vivo to generate siRNA constructs targeting the respiratory virus for silencing of the viral gene. Alternatively, two constructs can be utilized to create the sense and antisense strands of a siRNA construct. Further, cloned DNA can encode a transcript having secondary structure, wherein a single transcript has both the sense and complementary antisense sequences from the target gene or genes. In an example of this embodiment, a hairpin RNAi product is similar to all or a portion of the target gene. In another example, a hairpin RNAi product is a siRNA. The regulatory sequences flanking the viral sequence may be identical or may be different, such that their expression may be modulated independently, or in a temporal or spatial manner.

In certain embodiments, siRNAs are transcribed intracellularly by cloning the viral gene templates into a vector containing, e.g., a RNA pol III transcription unit from the smaller nuclear RNA (snRNA) U6 or the human RNase P RNA H1. One example of a vector system is the GeneSuppressor™ RNA Interference kit (commercially available from Imgenex). The U6 and H1 promoters are members of the type III class of Pol III promoters. The +1 nucleotide of the U6-like promoters is always guanosine, whereas the +1 for H1 promoters is adenosine. The termination signal for these promoters is defined by five consecutive thymidines. The transcript is typically cleaved after the second uridine. Cleavage at this position generates a 3' UU overhang in the expressed siRNA, which is similar to the 3' overhangs of synthetic siRNAs. Any sequence less than 400 nucleotides in length can be transcribed by these promoter, therefore they are ideally suited for the expression of around 21-nucleotide siRNAs in, e.g., an approximately 50-nucleotide RNA stem-loop transcript. The characteristics of RNAi and of factors affecting siRNA efficacy have been studied (See, e.g., Elbashir, Lendeckel and Tuschl (2001). Genes & Dev. 15: 188-200).

An initial BLAST homology search for the selected siRNA sequence is done against an available nucleotide sequence library to ensure that only a viral gene, but no host gene, is targeted. See, Elbashir et al. 2001 EMBO J. 20(23):6877-88.

Synthesis of Polynucleotides

Oligonucleotides corresponding to targeting nucleotide sequences, and polynucleotides that include targeting sequences, can be prepared by standard synthetic techniques, e.g., using an automated DNA synthesizer. Methods for synthesizing oligonucleotides include well-known chemical processes, including, but not limited to, sequential addition of nucleotide phosphoramidites onto surface-derivatized particles, as described by T. Brown and Dorcas J. S. Brown in Oligonucleotides and Analogues A Practical Approach, F. Eckstein, editor, Oxford University Press, Oxford, pp. 1-24 (1991), and incorporated herein by reference.

An example of a synthetic procedure uses Expedite RNA phosphoramidites and thymidine phosphoramidite (Proligo, Germany). Synthetic oligonucleotides are deprotected and gel-purified (Elbashir et al. (2001) Genes & Dev. 15, 188-200), followed by Sep-Pak C18 cartridge (Waters, Milford, Mass., USA) purification (Tuschl et al. (1993) Biochemistry, 32:11658-11668). Complementary ssRNAs are incubated in an annealing buffer (100 mM potassium acetate, 30 mM HEPES-KOH at pH 7.4, 2 mM magnesium acetate) for 1 min at 90° C. followed by 1 h at 37° C. to hybridize to the corresponding ds-siRNAs.

Other methods of oligonucleotide synthesis include, but are not limited to solid-phase oligonucleotide synthesis according to the phosphotriester and phosphodiester methods (Narang, et al., (1979) Meth. Enzymol. 68:90), and to the H-phosphonate method (Garegg, P. J., et al., (1985) "Formation of internucleotidic bonds via phosphonate intermediates", Chem. Scripta 25, 280-282; and Froehler, B. C., et al., (1986a) "Synthesis of DNA via deoxynucleoside H-phosphonate intermediates", Nucleic Acid Res., 14, 5399-5407, among others) and synthesis on a support (Beaucage, et al. (1981) Tetrahedron Letters 22:1859-1862) as well as phosphoramidate techniques (Caruthers, M. H., et al., "Methods in Enzymology," Vol. 154, pp. 287-314 (1988), U.S. Pat. Nos. 5,153,319, 5,132,418, 4,500,707, 4,458,066, 4,973,679, 4,668,777, and 4,415,732, and others described in "Synthesis and Applications of DNA and RNA," S. A. Narang, editor, Academic Press, New York, 1987, and the references contained therein, and nonphosphoramidite techniques. Solid phase synthesis helps isolate the oligonucleotide from impurities and excess reagents. Once cleaved from the solid support the oligonucleotide may be further isolated by known techniques.

Inhibitory Polynucleotides of the Invention

The invention provides broadly for oligonucleotides intended to provoke an RNA interference phenomenon upon entry into a cell infected with a respiratory viral pathogen. The present invention, while not restricted in the nature of a respiratory virus target, emphasizes oligonucleotides targeting RSV and several strains of influenza A. RNA interference is engendered within the cell by appropriate double stranded RNAs one of whose strands is identical to or highly similar to a sequence in a target gene of the virus. In general, an oligonucleotide that targets a respiratory virus may be a DNA or an RNA, or it may contain a mixture of ribonucleotides and deoxyribonucleotides. An example of the latter is an RNA sequence terminated at the 3' end with a deoxydinucleotide sequence, such as d(TT), d(UU), d(TU), d(UT), as well as other possible dinucleotides. In additional embodiments the 3' overhang may be constituted of ribonucleotides having the bases specified above, or others. Furthermore, the oligonucleotide pharmaceutical agent may be single stranded or double stranded. Several embodiments of the therapeutic oligonucleotides of the invention are envisioned to be oligoribonucleotides, or oligoribonucleotides with 3' d(TT) terminals. A single stranded targeting polynucleotide, upon entry into a mammalian cell, is readily converted to a double stranded molecule by endogenous enzyme activity resident in the cell.

Most generally the invention provides oligonucleotides or polynucleotides that may range in length anywhere from 15 nucleotides to as long as 200 nucleotides. The polynucleotides include a first nucleotide sequence that targets the genome of a respiratory syncytial virus or an influenza A virus. The first nucleotide sequence consists of either a) a sequence whose length is any number of nucleotides from 15 to 30, or b) a complement thereof. Such a polynucleotide is termed a linear polynucleotide herein.

FIG. 3 provides schematic representations of certain embodiments of the polynucleotides of the invention. The invention discloses target sequences in an RSV or in various strains of influenza A, or in certain cases siRNA sequences that are slightly mismatched from a target sequence, all of which are provided in SEQ ID NOS:1-263. The sequences disclosed therein range in length from 19 nucleotides to 25 nucleotides. The targeting sequences are represented by the lightly shaded blocks in FIG. 3. FIG. 3, Panel A, a) illustrates an embodiment in which the disclosed sequence shown as "SEQ" may optionally be included in a larger polynucleotide whose overall length may range up to 200 nucleotides.

The invention additionally provides that, in the targeting polynucleotide, a sequence chosen from SEQ ID NOS:1-263 may be part of a longer targeting sequence such that the targeting polynucleotide targets a sequence in the viral genome that is longer than the first nucleotide sequence represented by SEQ. This is illustrated in FIG. 3, Panel A, b), in which the complete targeting sequence is shown by the horizontal line above the polynucleotide, and by the darker shading surrounding the SEQ block. As in all embodiments of the polynucleotides, this longer sequence may optionally be included in a still larger polynucleotide of length 200 or fewer bases (FIG. 3, Panel A, b)).

The invention further provides a sequence that is a fragment of any of SEQ ID NOS:1-263 that is at least 15 nucleotides in length (and at most 1 base shorter than the reference SEQ ID NO:; illustrated in FIG. 3, Panel A, c)), as well as a sequence wherein up to 5 nucleotides may differ from the target sequence given in SEQ ID NOS:1-263 (illustrated in FIG. 3, Panel A, d), showing, in this example, three variant bases represented by the three darker vertical bars).

Still further the invention provides a sequence that is a complement to any of the above-described sequences (shown in FIG. 3, Panel A, e), and designated as "COMPL"). Any of these sequences are included in the oligonucleotides or polynucleotides of the invention. Any linear polynucleotide of the invention may be constituted of only the sequences described in a)-e) above, or optionally may include additional bases up to the limit of 200 nucleotides. Since RNA interference requires double stranded RNAs, the targeting polynucleotide itself may be double stranded, including a second strand complementary to at least the sequence given by SEQ ID NOS:1-263 and hybridized thereto, or intracellular processes may be relied upon to generate a complementary strand.

Thus the polynucleotide may be single stranded, or it may be double stranded. In still further embodiments, the polynucleotide contains only deoxyribonucleotides, or it contains only ribonucleotides, or it contains both deoxyribonucleotides and ribonucleotides. In important embodiments of the polynucleotides described herein the target sequence consists of a sequence that may be either 15 nucleotides (nt), or 16 nt, or 17 nt, or 18 nt, or 19 nt, or nt, or 21 nt, or 22 nt, or 23 nt, or 24 nt, or 25 nt, or 26 nt, or 27 nt, or 28 nt, or 29, or 30 nt in length. In still additional advantageous embodiments the targeting sequence may differ by up to 5 bases from a target sequence in the viral pathogen genome.

In several embodiments of the invention, the polynucleotide is an siRNA consisting of the targeting sequence with optional inclusion of a 3' dinucleotide overhang described herein.

Alternatively, in recognition of the need for a double stranded RNA in RNA interference, the oligonucleotide or polynucleotide may be prepared to form an intramolecular hairpin looped double stranded molecule. Such a molecule is formed of a first sequence described in any of the embodiments of the preceding paragraphs followed by a short loop sequence, which is then followed in turn by a second sequence that is complementary to the first sequence. Such a structure forms the desired intramolecular hairpin. Furthermore, this polynucleotide is disclosed as also having a maximum length of 200 nucleotides, such that the three required structures enumerated may be constituted in any oligonucleotide or polynucleotide having any overall length of up to 200 nucleotides. A hairpin loop polynucleotide is illustrated in FIG. 3, Panel B.

RSV Strains as Targets

For RSV, although any portion of the viral genome may be targeted, it is reasonable that targeting genes that code for viral-specific enzymatic functions should provide potent siRNA candidates. These include the L, F, G and P genes. The L gene, located at the 5' end of the viral genome, is expressed in only small amounts, so that effective RNAi silencing may require only small amounts of siRNA. The structural genes may also be targeted.

Sequences of the following representative strains of RSV subgroups A and B were used to select target sequences that are either common between subgroups A and B (Table 1) or specific for subgroup A (Table 2) or B (Table 3):

Subgroup A: Strain A2 (GenBank M74568) and strain Long (only the P-mRNA, GenBank M22644, and F-mRNA, GenBank M22643).

Subgroup B: Strain B1 (GenBank NC_001781) and strain 9320 (GenBank AY353550).

The viral gene sequences were aligned to seek common or unique regions. For each targeted gene or region at least two targets were chosen unless not applicable (NA). It was more difficult to find target sequences common to both subgroups than to find targets unique for either of them, since there are very few homologous or identical sequences available. In this case (Table 1), it was sometimes necessary to introduce a mismatch into the 5' base of one end of the RNA duplex.

TABLE 1

Gene targets common to RSV subgroups A and B (strains A2, B1 and 9230)

| Target gene* | Sequence (5' to 3')** | Position on A2 (M734568) | Position on B1 (NC_001781) | Position on 9230 (AY353550) | SEQ ID NO: |
|---|---|---|---|---|---|
| Leader/NS1 (−) strand | AATGGGGCAAATAAGAATTTG | 42-62 | 42-62 | 42-62 | 1 |
| Leader/NS1 | AATGGGGCAAATAAGAATTTg | 42-62 | 42-62 | 42-62 | 2 |
| N | AAGATGGCTCTTAGCAAAGTc | 1137-1157 | 1137-1157 | 1135-1155 | 3 |
| P | AATTCCTAGAATCAATAAAGg | 2401-2421 | 2403-2423 | 2401-2421 | 4 |
| M | AAGCTTCACGAAGGCTCCACA | 3279-3299 | 3281-3301 | 3279-3299 | 5 |
| SH | NA | | | | |
| G | NA | | | | |
| F | AATGATATGCCTATAACAAAt | 6444-6464 | 6449-6469 | 6447-6467 | 6 |
| M2 | AAGATAAGAGTGTACAATACT | 7975-7995 | 7987-8007 | 7986-8006 | 7 |
| M2/L | NA | | | | |
| L | AACATCCTCCATCATGGTTAA | 9090-9110 | 9101-9121 | 9100-9120 | 8 |
| L | AAGTACTAATTTAGCTGGACA | 12973-12993 | 12984-13004 | 12983-13003 | 9 |
| L | AAGATTGCAATGATCATAGTT | 14133-14153 | 14144-14164 | 14143-14163 | 10 |
| L | AACATTCATTGGTCTTATTTA | 14243-14263 | 14254-14274 | 14253-14273 | 11 |
| Trail | NA | | | | |

NA = Not applicable
*Targets are mostly (+) strand RNAs, e.g., mRNAs; except otherwise specified, e.g., the first target.
**When siRNAs are designed, a "mismatch" is needed for each of these nucleotides in lowercase (g, c, or t), in order to reduce the thermodynamic energy value at this end of siRNA duplex.
Bases in bold lower case italics represent mismatches.

TABLE 2

Gene targets specific for subgroup A (Strains A2 & F/P of Long strains)

| Target gene | Sequence (5' to 3')* | Position in A2 genome (M734568) | SEQ ID NO: |
|---|---|---|---|
| Leader (−) strand | AAATGCGTACAACAAACTTGC | 9-29 | 12 |
| Leader | AACAAACTTGCATAAACCAAA | 19-39 | 13 |
| NS1 | AAGAATTTGATAAGTACCACT | 54-74 | 14 |
| NS1 | AACTAACGCTTTGGCTAAGGC | 209-229 | 15 |
| NS2 | AATAAATCAATTCAGCCAACC | 602-622 | 16 |
| NS2 | AACTATTACACAAAGTAGGAA | 830-850 | 17 |
| N | AACAAAGATCAACTTCTGTCA | 1176-1196 | 18 |
| N | AAGAAATGGGAGAGGTAGCTC | 1558-1578 | 19 |
| P | AATTCAACTATTATCAACCCA | 2520-2530 | 20 |
| P | AACAATGAAGAAGAATCCAGC | 2676-2696 | 21 |
| M | AAATAAAGATCTGAACACACT | 3770-3790 | 22 |
| M | AAATATCCACACCCAAGGGAC | 3442-3462 | 23 |
| M | AAATAAAGATCTGAACACACT | 3770-3790 | 24 |
| SH | AACATAGACAAGTCCACACAC | 4266-4286 | 25 |
| SH | AACAATAGAATTCTCAAGCAA | 4320-4340 | 26 |
| G | AAACAAGGACCAACGCACCGC | 4696-4716 | 27 |
| G | AACTTCACTTATAATTGCAGC | 4840-4860 | 28 |
| F | AAATAAGTGTAATGGAACAGA | 5858-5878 | 29 |
| F | AAACAATCGAGCCAGAAGAGA | 5969-5989 | 30 |
| M2 | AAATAAGTGGAGCTGCAGAGT | 7781-7801 | 31 |
| M2 | AACAATCAGCATGTGTTGCCA | 7880-7900 | 32 |
| M2/L | NA | | |
| L | AAGTTACATATTCAATGGTCC | 8593-8613 | 33 |
| L | AACTAAATATAACACAGTCCT | 8685-8905 | 34 |
| Trail | NA | | |

NA = Not applicable

TABLE 3

Gene targets specific for subgroup B (Strains B1 and 9320)

| Target gene | Sequence (5' to 3')* | Position in B1 genome (NC-001781) | Position in 9320 genome (AY353550) | SEQ ID NO: |
|---|---|---|---|---|
| Leader (−) strand | AATGCGTACTACAAACTTGCA | 10-30 | 10-30 | 35 |
| Leader | AAATGCGTACTACAAACTTGC | 9-29 | 9-29 | 36 |
| NS1 | AATTAATTCTTCTGACCAATG | 196-216 | 196-216 | 37 |
| NS1 | AACAAGCAGTGAAGTGTGCCC | 278-298 | 278-298 | 38 |
| NS2 | AATAATAACATCTCTCACCAA | 700-720 | 700-720 | 39 |
| NS2 | AATGTATTGGCATTAAGCCTA | 936-956 | 936-956 | 40 |
| N | AAATAAGGATCAGCTGCTGTC | 1175-1195 | 1173-1193 | 41 |
| N | AACAAACTATGTGGTATGCTA | 1272-1292 | 1270-1290 | 42 |
| P | AATAAAGGGCAAGTTCGCATC | 2416-2436 | 2414-2434 | 43 |
| P | AACAAATGACAACATTACAGC | 2725-2745 | 2723-2743 | 44 |
| M | AATATGGGTGCCTATGTTCCA | 3361-3381 | 3359-3379 | 45 |
| M | AACATACTAGTGAAGCAGATC | 3428-3448 | 3426-3446 | 46 |
| SH | AAATACATCCATCACAATAGA | 4308-4328 | 4306-4326 | 47 |
| SH | AAACATTCTGTAACAATACTC | 4445-4465 | 4443-4463 | 48 |
| G | AATCTATAGCACAAATAGCAC | 4796-4816 | 4794-4814 | 49 |
| G | AATATTCATCATCTCTGCCAA | 4866-4886 | 4864-4884 | 50 |
| F | AAAGAAACCAAATGCAATGGA | 5858-5878 | 5856-5876 | 51 |

TABLE 3-continued

Gene targets specific for subgroup B
(Strains B1 and 9320)

| Target gene | Sequence (5' to 3')* | Position in B1 genome (NC-001781) | Position in 9320 genome (AY353550) | SEQ ID NO: |
|---|---|---|---|---|
| F | AAACAAAGCTGTAGTCAGTCT | 6187-6207 | 6185-6205 | 52 |
| M2 | AAATAAGTGGAGCTGCTGAAC | 7793-7813 | 7792-7812 | 53 |
| M2 | AACAATCAGCATGTGTTGCTA | 7892-7912 | 7892-7911 | 54 |
| M2/L | NA | | | |
| L | AAATAACATCACAGATGCAGC | 9591-9611 | 9590-9610 | 55 |
| L | AATACCTACAACAGATGGCCC | 9931-9951 | 9930-9950 | 56 |
| Trail | NA | | | |

NA = Not applicable

In order provide siRNA agents directed to the 5'-end of the viral genome, trail-targets unique to either strain B1 or strain 9320 individually are shown below (Table 4). The 5' terminus of the (+) strand (anti-genomic RNA) is targeted, i.e., the nascent leader sequence produced when the viral genome begins to replicate using the positive RNA strand (the antigenomic RNA) as template.

TABLE 4

Trail targets for two strains of RSV subgroup B

| Target gene | Sequence (5' to 3')* | Position in B1 genome (NC_001781) | Position in 9320 genome (AY353550) | SEQ ID NO: |
|---|---|---|---|---|
| Trail | AATTTAGCTTACTGATTCCAA | 15098-15108 | NA | 57 |
| Trail | AACTAACAATGATACATGTGC | 15159-15179 | NA | 58 |
| Trail | AATTTAGCATA*T*TGATTCCAA | NA | 15097-15107 | 59 |
| Trail | AACTAACAAT*T*ATACATGTGC | NA | 15158-15178 | 60 |

Bases in BOLD ITALICS represent mismatches.

Based upon the targets listed above in Table 1-Table 4, siRNAs may be created as follows: a) Each strand of a double stranded siRNA are provided with a 3'-dTdT overhang b) In case a "mismatch" is needed, G:C are changed to G:T or G:A; A:T will be changed to A:C or A:G; and C:G will be changed to C:T or C:A.

Influenza a Strains as Targets siRNA target sequences of lengths of 25 and 19 nucleotides within the (+) stranded mRNA sequences have been identified in all eight segments. The sequences are presented in Table 5-Table 12. siRNA sequences s from each of the eight segments. The entry for each sequence also shows the starting nucleotide location in the mRNA from the 5' end.

TABLE 5 siRNA sequences targeting the hemagglutinin gene of influenza A virus (A/chicken/Thailand/CH-2/2004(H5N1); GenBank AY649382).

| Start Nucleotide No. | Sequence | SEQ ID NO: |
|---|---|---|
| 177 | TCTAGATGGAGTGAAGCCTCTAATT | 61 |
| 295 | GCCAATCCAGTCAATGACCTCTGTT | 62 |
| 453 | TCCATACCAGGGAAAGTCCTCCTTT | 63 |
| 601 | GCAGAGCAGACAAAGCTCTATCAAA | 64 |
| 678 | ACCAAGAATAGCTACTAGATCCAAA | 65 |
| 710 | GCCAAAGTGGAAGGATGGAGTTCTT | 66 |

TABLE 5-continued siRNA sequences targeting the hemagglutinin gene of influenza A virus (A/chicken/Thailand/CH-2/2004(H5N1); GenBank AY649382).

| Start Nucleotide No. | Sequence | SEQ ID NO: |
|---|---|---|
| 718 | GGAAGGATGGAGTTCTTCTGGACAA | 67 |
| 869 | GCAACACCAAGTGTCAAACTCCAAT | 68 |
| 1501 | GGAACGTATGACTACCCGCAGTATT | 69 |
| 1673 | CCAATGGGTCGTTACAATGCAGAAT | 70 |
| 25 | GCAATAGTCAGTCTTGTTA | 71 |
| 267 | GCCGGAATGGTCTTACATA | 72 |
| 416 | CCAGTCATGAAGCCTCATT | 73 |
| 533 | GGAGCTACAATAATACCAA | 74 |
| 688 | GCTACTAGATCCAAAGTAA | 75 |
| 875 | CCAAGTGTCAAACTCCAAT | 76 |
| 988 | GCGACTGGGCTCAGAAATA | 77 |
| 1302 | CCTAGATGTCTGGACTTAT | 78 |
| 1625 | CCCTAGCACTGGCAATCAT | 79 |
| 1678 | GGGTCGTTACAATGCAGAA | 80 |

TABLE 6 siRNA sequences targeting the matrix protein 2 and matrix protein 1 (M) genes of influenza A virus (A/Thailand/1(KAN-1)/2004(H5N1); GenBank AY626144).

| Start Nucleotide No. | Sequence | SEQ ID NO: |
|---|---|---|
| 171 | GACCAATCCTGTCACCTCTGACTAA | 81 |
| 172 | ACCAATCCTGTCACCTCTGACTAAA | 82 |
| 178 | CCTGTCACCTCTGACTAAAGGGATT | 83 |
| 265 | CCAGAATGCCCTAAATGGAAATGGA | 84 |
| 272 | GCCCTAAATGGAAATGGAGATCCAA | 85 |
| 373 | ACTCAGCTACTCAACCGGTGCACTT | 86 |
| 521 | GCAACTACCACCAACCCACTAATCA | 87 |
| 772 | GCGATTCAAGTGATCCTATTGTTGT | 88 |
| 786 | CCTATTGTTGTTGCCGCAAATATCA | 89 |
| 826 | TGATATTGTGGATTCTTGATCGTCT | 90 |
| 31 | TCTTCTAACCGAGGTCGAA | 91 |
| 177 | TCCTGTCACCTCTGACTAA | 92 |
| 178 | CCTGTCACCTCTGACTAAA | 93 |
| 399 | CCAGTTGCATGGGTCTCAT | 94 |
| 573 | GCACTACAGCTAAGGCTAT | 95 |

TABLE 6-continued siRNA sequences targeting the matrix protein 2 and matrix protein 1 (M) genes of influenza A virus (A/Thailand/1(KAN-1)/2004(H5N1); GenBank AY626144).

| Start Nucleotide No. | Sequence | SEQ ID NO: |
|---|---|---|
| 772 | GCGATTCAAGTGATCCTAT | 96 |
| 813 | GGGATCTTGCACTTGATAT | 97 |
| 814 | GGATCTTGCACTTGATATT | 98 |
| 821 | GCACTTGATATTGTGGATT | 99 |
| 862 | GCATTTATCGTCGCCTTAA | 100 |

TABLE 7 siRNA sequences targeting the neuraminidase gene of influenza A virus (A/chicken/Thailand/CH-2/2004(H5N1) GenBank AY649383).

| Start Nucleotide No. | Sequence | SEQ ID NO: |
|---|---|---|
| 53 | ACCATCGGATCAATCTGTATGGTAA | 101 |
| 164 | GCTGAACCAATCAGCAATACTAATT | 102 |
| 401 | TCCAATGGGACTGTCAAAGACAGAA | 103 |
| 577 | GGCTGTATTGAAATACAATGGCATA | 104 |
| 662 | GCATGTGTAAATGGCTCTTGCTTTA | 105 |
| 749 | GGGAAAGTGGTTAAATCAGTCGAAT | 106 |
| 750 | GGAAAGTGGTTAAATCAGTCGAATT | 107 |
| 779 | GCTCCTAATTATCACTATGAGGAAT | 108 |
| 843 | GCAGGGATAATTGGCATGGCTCAAA | 109 |
| 1189 | CCAGCATCCAGAACTGACAGGACTA | 110 |
| 54 | CCATCGGATCAATCTGTAT | 111 |
| 59 | GGATCAATCTGTATGGTAA | 112 |
| 164 | GCTGAACCAATCAGCAATA | 113 |
| 407 | GGGACTGTCAAAGACAGAA | 114 |
| 500 | GCTTGGTCAGCAAGTGCTT | 115 |
| 528 | GCACCAGTTGGTTGACAAT | 116 |
| 572 | GCTGTGGCTGTATTGAAAT | 117 |
| 662 | GCATGTGTAAATGGCTCTT | 118 |
| 675 | GCTCTTGCTTTACTGTAAT | 119 |
| 1068 | CCAGGAGCGGCTTTGAAAT | 120 |

TABLE 8 siRNA sequences targeting the nucleocapsid protein (NP) gene of influenza A virus (A/Thailand/1(KAN-1)/2004(H5N1); GenBank AY626145).

| Start Nucleotide No. | Sequence | SEQ ID NO: |
|---|---|---|
| 64 | GCGTCTCAAGGCACCAAACGATCTT | 121 |
| 191 | GCACAGAACTCAAACTCAGTGACTA | 122 |
| 451 | GCTGGTCTTACCCACCTGATGATAT | 123 |
| 627 | GGTGATGGAGCTGATTCGGATGATA | 124 |
| 854 | TCCTGAGAGGATCAGTGGCCCATAA | 125 |
| 910 | GCAGTGGCCAGTGGATATGACTTTG | 126 |
| 916 | GCCAGTGGATATGACTTTGAGAGAG | 127 |
| 993 | GGTCTTTAGTCTCATTAGACCAAAT | 128 |
| 1173 | GGAGGCAATGGACTCCAACACTCTT | 129 |
| 1331 | CCATTATGGCAGCATTTACAGGAAA | 130 |
| 116 | GCCAGAATGCTACTGAGAT | 131 |
| 381 | GCTAATTCTGTACGACAAA | 132 |
| 413 | GGATTTGGCGTCAAGCGAA | 133 |
| 989 | GCCAGGTCTTTAGTCTCAT | 134 |
| 1024 | CCAGCACATAAGAGTCAAT | 135 |
| 1066 | GCAGCATTTGAGGACCTTA | 136 |
| 1182 | GGACTCCAACACTCTTGAA | 137 |
| 1327 | GCGACCATTATGGCAGCAT | 138 |
| 1339 | GCAGCATTTACAGGAAATA | 139 |
| 1351 | GGAAATACTGAGGGCAGAA | 140 |

TABLE 9 siRNA sequences targeting the nonstructural protein 1 and nonstructural protein 2 (NS) genes of influenza A virus (A/Thailand/1(KAN-1)/2004(H5N1); GenBank AY626146).

| Start Nucleotide No. | Sequence | SEQ ID NO: |
|---|---|---|
| 82 | TCTTTGGCATGTCCGCAAACGATTT | 141 |
| 299 | GACATGACTCTCGAAGAAATGTCAA | 142 |
| 509 | CCATTACCTTCTCTTCCAGGACATA | 143 |
| 564 | TCCTCATCGGAGGACTTGAATGGAA | 144 |
| 565 | CCTCATCGGAGGACTTGAATGGAAT | 145 |
| 570 | TCGGAGGACTTGAATGGAATGATAA | 146 |
| 603 | GAGTCACTGAAACTATACAGAGATT | 147 |
| 827 | GCAAGAGATAAGAGCCTTCTCGTTT | 148 |
| 838 | GAGCCTTCTCGTTTCAGCTTATTTA | 149 |
| 840 | GCCTTCTCGTTTCAGCTTATTTAAT | 150 |
| 48 | CCAACACTGTGTCAAGCTT | 151 |
| 63 | GCTTTCAGGTAGACTGCTT | 152 |
| 88 | GCATGTCCGCAAACGATTT | 153 |
| 165 | CCCTAAGAGGAAGAGGCAA | 154 |
| 253 | GGAGTCTGATAAGGCACTT | 155 |
| 324 | GGGACTGGTTCATGCTCAT | 156 |
| 330 | GGTTCATGCTCATGCCCAA | 157 |
| 337 | GCTCATGCCCAAGCAGAAA | 158 |
| 840 | GCCTTCTCGTTTCAGCTTA | 159 |
| 841 | CCTTCTCGTTTCAGCTTAT | 160 |

TABLE 10 siRNA sequences targeting the polymerase acidic protein (PA) gene of influenza A virus (A/Thailand/1(KAN-1)/2004(H5N1); GenBank AY626147).

| Start Nucleotide No. | Sequence | SEQ ID NO: |
|---|---|---|
| 64 | CCAATGATCGTCGAGCTTGCGGAAA | 161 |
| 159 | GGAGGTCTGTTTCATGTATTCGGAT | 162 |
| 296 | GGACTGTGGTGAATAGTATCTGCAA | 163 |
| 588 | GGGTCTATGGGATTCCTTTCGTCAA | 164 |
| 691 | CCACCGAACTTCTCCAGCCTTGAAA | 165 |
| 888 | GGATGCCCTTAAATTAAGCATCGAA | 166 |
| 935 | GGATACCACTATACGATGCAATCAA | 167 |
| 991 | CCCAACATCGTGAAACCACATGAAA | 168 |
| 1568 | GGAATGATACCGATGTGGTAAATTT | 169 |
| 2189 | GGCAATGCTACTATTTGCTATCCAT | 170 |
| 36 | GGAAGACTTTGTGCGACAA | 171 |
| 340 | CCTAAATTTCTCCCAGATT | 172 |
| 510 | GGACTACACCCTTGATGAA | 173 |
| 882 | GCTGATGGATGCCCTTAAA | 174 |
| 1602 | GGAATTCTCTCTTACTGAT | 175 |
| 1690 | GCAGTAGGCCAAGTTTCAA | 176 |
| 1710 | GCCCATGTTCCTGTATGTA | 177 |

TABLE 10-continued siRNA sequences targeting the polymerase acidic protein (PA) gene of influenza A virus (A/Thailand/1(KAN-1)/2004(H5N1); GenBank AY626147).

| Start Nucleotide No. | Sequence | SEQ ID NO: |
|---|---|---|
| 1770 | GGAAATGAGGCGATGCCTT | 178 |
| 2163 | CCTCGCACATGCACTGAAA | 179 |
| 2190 | GCAATGCTACTATTTGCTA | 180 |

TABLE 11 siRNA sequences targeting the polymerase basic protein 1 (PB1) gene of influenza A virus (A/Thailand/1(KAN-1)/2004(H5N1); GenBank AY626148).

| Start Nucleotide No. | Sequence | SEQ ID NO: |
|---|---|---|
| 28 | GGCAAACCATTTGAATGGATGTCAA | 181 |
| 90 | GCTATAAGTACCACATTCCCTTATA | 182 |
| 424 | CCTATGACTGGACATTGAATAGAAA | 183 |
| 1028 | GCCAGAATGGTTTCGGAATGTCTTA | 184 |
| 1042 | GGAATGTCTTAAGCATTGCACCTAT | 185 |
| 1355 | GGACGGACTCCAATCCTCTGATGAT | 186 |
| 1444 | GGACTTGTAAACTAGTTGGAATCAA | 187 |
| 1824 | GGACCAAATCTATACAATATCCGAA | 188 |
| 2022 | GCAACTACACATTCATGGATTCCTA | 189 |
| 2206 | CCCGAATTGACGCACGAATTGATTT | 190 |
| 25 | GCAGGCAAACCATTTGAAT | 191 |
| 34 | CCATTTGAATGGATGTCAA | 192 |
| 288 | GCACAAACAGATTGTGTAT | 193 |
| 702 | GCACTGACACTGAACACAA | 194 |
| 765 | GCAACACCCGGAATGCAAA | 195 |
| 988 | GGATGTTTCTGGCAATGAT | 196 |
| 1021 | GGAACCAGCCAGAATGGTT | 197 |
| 1059 | GCACCTATAATGTTCTCAA | 198 |
| 1157 | GCTTGCAAACATTGATCTT | 199 |
| 1753 | GGAGATCATTCGAGCTGAA | 200 |

TABLE 12 siRNA sequences targeting the polymerase basic protein 2 (PB2) gene of influenza A virus (A/Thailand/1(KAN-1)/2004(H5N1); GenBank AY626149).

| Start Nucleotide No. | Sequence | SEQ ID NO: |
|---|---|---|
| 68 | CCCGCACTCGCGAGATACTAACAAA | 201 |
| 193 | CCAATCACAGCGGACAAGAGAATAA | 202 |
| 870 | GGAGATGTGTCACAGCACACAAATT | 203 |
| 939 | GGAACAAGCTGTGGATATATGCAAA | 204 |
| 1315 | CCCATGCATCAACTCCTGAGACATT | 205 |
| 1403 | GGATGATCGGAATATTACCTGACAT | 206 |
| 1420 | CCTGACATGACTCCCAGCACAGAAA | 207 |
| 1849 | GGGACATTTGATACTGTCCAGATAA | 208 |
| 1866 | CCAGATAATAAAGCTGCTACCATTT | 209 |
| 2135 | GGTATGGACCAGCATTGAGCATCAA | 210 |
| 310 | GCTGTAACTTGGTGGAATA | 211 |
| 413 | CCTTTGGTCCCGTTCATTT | 212 |
| 603 | GCTCCAAGATTGTAAGATT | 213 |
| 717 | GGTATTGCATTTGACTCAA | 214 |
| 811 | GCTGCCAGAAACATTGTTA | 215 |
| 899 | GGATAAGGATGGTGGACAT | 216 |
| 1189 | GGAAGAGACGAACAATCAA | 217 |
| 1320 | GCATCAACTCCTGAGACAT | 218 |
| 2153 | GCATCAATGAACTGAGCAA | 219 |
| 2296 | GCCATCAATTAGTGTCGAA | 220 |

Another approach for selection of the potent siRNA candidate sequences targeting influenza A is to focus on the subtype-specificity of the two major viral surface glycoproteins, hemagglutinin (HA) and neuraminidase (NA). The subtypes that have been reported to cause human infection are H5N1, H7N7, and H9N2. The following are examples of the subtype-specific HA and NA targets.

TABLE 13 siRNA-targeted sequences of H5N1 Hemagglutinin (HA) (based on GenBank DQ023145, GI: 66775624):

| No. | Sequence (5' to 3') | Position | SEQ ID NO: |
|---|---|---|---|
| 1 | AATGGTAGATGGTTGGTATGG | 1091-1111 | 221 |
| 2 | AAGGCAATAGATGGAGTCACC | 1170-1190 | 222 |
| 3 | AACACTCAGTTTGAGGCCGTT | 1221-1241 | 223 |
| 4 | AAGATGGAAGACGGATTCCTA | 1290-1310 | 224 |
| 5 | AATGCTGAACTTCTGGTTCTC | 1326-1346 | 225 |

TABLE 13-continued siRNA-targeted sequences of H5N1 Hemagglutinin (HA) (based on GenBank DQ023145, GI: 66775624):

| No. | Sequence (5' to 3') | Position | SEQ ID NO: |
|---|---|---|---|
| 6 | AACTCTAGACTTTCATGACTC | 1361-1381 | 226 |
| 7 | AAGGTCCGACTACAGCTTAGG | 1404-1424 | 227 |
| 8 | AATGTGATAATGAATGTATGG | 1471-1491 | 228 |
| 9 | AACAGTGGCGAGTTCCCTAGC | 1516-1636 | 229 |

The sequences in Table 13 are shared by six H5N1 strains isolated from chicken infected by HPAI viruses in China between year 2000 and 2003. These H5N1 strains are listed in the Table 14.

TABLE 14

| No. | Definition | Accession code |
|---|---|---|
| 1 | A/chicken/Huadong/1/2000(H5N1) | DQ201829, GI:76786306 |
| 2 | A/chicken/Zhengahou/1/2002(H5N1) | DQ211923, GI:76800615 |
| 3 | A/chicken/China/1/2002(H5N1) | DQ023145, GI:66775624 |
| 4 | A/chicken/Zhoukou/2/2002(H5N1) | DQ211924, GI:76800617 |
| 5 | A/chicken/Jiyuan/1/2003(H5N1) | DQ211922, GI:76800613 |
| 6 | A/chicken/Luohuo/3/2003(H5N1) | DQ211925, GI:76800619 |

TABLE 15 siRNA-targeted sequences of H5N1 Neuraminidase (NA) (based on GenBank DQ023147, GI: 66775628).

| No. | Sequence (5' to 3') | Position | SEQ ID NO: |
|---|---|---|---|
| 1 | AATCTGTATGGTAATTGGAAT | 48-68 | 230 |
| 2 | AACATTAGCGGGCAATTCATC | 201-221 | 231 |
| 3 | AAAGACAGAAGCCCTCACAGA | 400-420 | 232 |
| 4 | AATTGGAATTTCTGGCCCAGA | 528-548 | 233 |
| 5 | AATGGGGCTGTGGCTGTATTG | 550-570 | 234 |
| 6 | AACAGACACTATCAAGAGTTG | 588-608 | 235 |
| 7 | AACATACTGAGAACTCAAGAG | 616-636 | 236 |
| 8 | AATGTGCATGTGTAAATGGCT | 641-661 | 237 |
| 9 | AATTATCACTATGAGGAGTGC | 769-789 | 238 |
| 10 | AATCACATGTGTGTGCAGGGA | 813-833 | 239 |
| 11 | AAGGGTTTTCATTTAAATACG | 992-1012 | 240 |
| 12 | AATGGGTGGACTGGAACGGAC | 1084-1104 | 241 |
| 13 | AACTGATTGGTCAGGATATAG | 1140-1160 | 242 |
| 14 | AACTGACAGGATTAGATTGCA | 1184-1204 | 243 |
| 15 | AAGACCTTGTTTCTGGGTTGA | 1206-1226 | 244 |
| 16 | AATCAGAGGGCGGCCCAAAGA | 1230-1250 | 245 |

The above sequences are shared by six H5N1 strains isolated from chicken or swine infected by in China between year 2001 and 2003. These H5N1 strains are listed in Table 16 below.

TABLE 16

| No. | Definition | Accession code |
|---|---|---|
| 1 | A/chicken/Kaifeng/1/2001 (H5N1) | DQ211930, GI:76800629 |
| 2 | A/Swine/Fujian/F1/2001 (H5N1) | AY747618, GI:54126532 |
| 3 | A/chicken/Zhengzhou/1/2002 (H5N1) | DQ211927, GI:76800623 |
| 4 | A/chicken/China/1/2002 (H5N1) | DQ023147, GI:66775628 |
| 5 | A/chicken/Zhoukou/2/2002 (H5N1) | DQ211928, GI:76800625 |
| 6 | A/chicken/Luohuo/3/2003 (H5N1) | DQ211929, GI:76800627 |

TABLE 17 siRNA-targeted sequences of H7N7 Hemagglutinin (HA) (based on GenBank AY999986, GI:66394837):

| No. | Sequence (5' to 3') | Position | SEQ ID NO: |
|---|---|---|---|
| 1 | AAGGTCTGATTGATGGGTGGT | 1061-1081 | 246 |
| 2 | AATGCACAAGGGGAGGGAACT | 1099-1119 | 247 |
| 3 | AAGCACCCAATCAGCAATTGA | 1134-1164 | 248 |
| 4 | AATAGACAATGAATTCACTGA | 1212-1232 | 249 |
| 5 | AAGCAAATTGGCAATGTGATA | 1240-1260 | 250 |
| 6 | AATTGGACCAGAGATTCCATG | 1261-1281 | 251 |
| 7 | AAGAGACAACTGAGAGAGAAT | 1384-1404 | 252 |
| 8 | AAGATGGCACTGGTTGCTTCG | 1412-1432 | 253 |
| 9 | AACACCTATGATCACAGCAAG | 1480-1500 | 254 |
| 10 | AATAGAATACAGATTGACCCA | 1522-1542 | 255 |

All these above sequences are shared by six H7N7 strains isolated from Mallard in Sweden in year 2002. These H7N7 strains are listed in Table 18 below.

By comparison of the six HA sequences, it was found the HA1 related domain has higher frequency of point mutations, therefore, 10 targets are chosen from the HA2 domain.

TABLE 18

| No. | Definition | Accession code |
|---|---|---|
| 1 | A/Mallard/Sweden/102/02 (H7N7) | AY999986, GI:66394837 |
| 2 | A/Mallard/Sweden/103/02 (H7N7) | AY999987, GI:66394839 |
| 3 | A/Mallard/Sweden/104/02 (H7N7) | AY999988, GI:66394841 |
| 4 | A/Mallard/Sweden/105/02 (H7N7) | AY999989, GI:66394843 |
| 5 | A/Mallard/Sweden/106/02 (H7N7) | AY999990, GI:66394845 |
| 6 | A/Mallard/Sweden/107/02 (H7N7) | AY999991, GI:66394847 |

Figure 4:
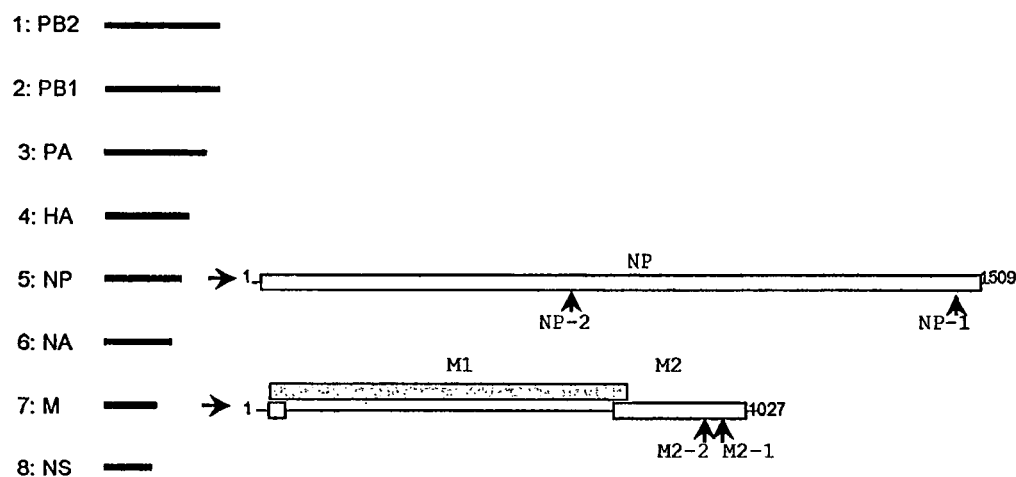
FIG. 4. Schematic diagrams showing the locations of siRNA sequences in the H5N1 genome FIG. 5. Inhibition of H5N1 virus growth in MDCK cell cultures FIG. 6. Inhibitory effect of siRNA determined in different time points
Figure 5:
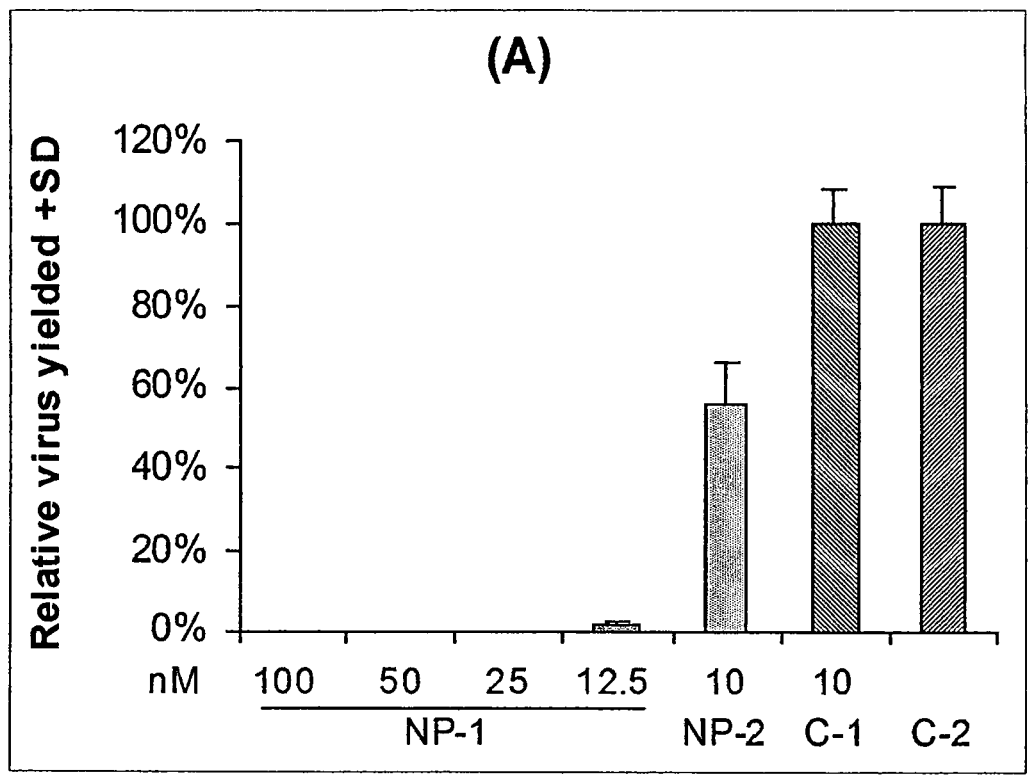
Figure 5:
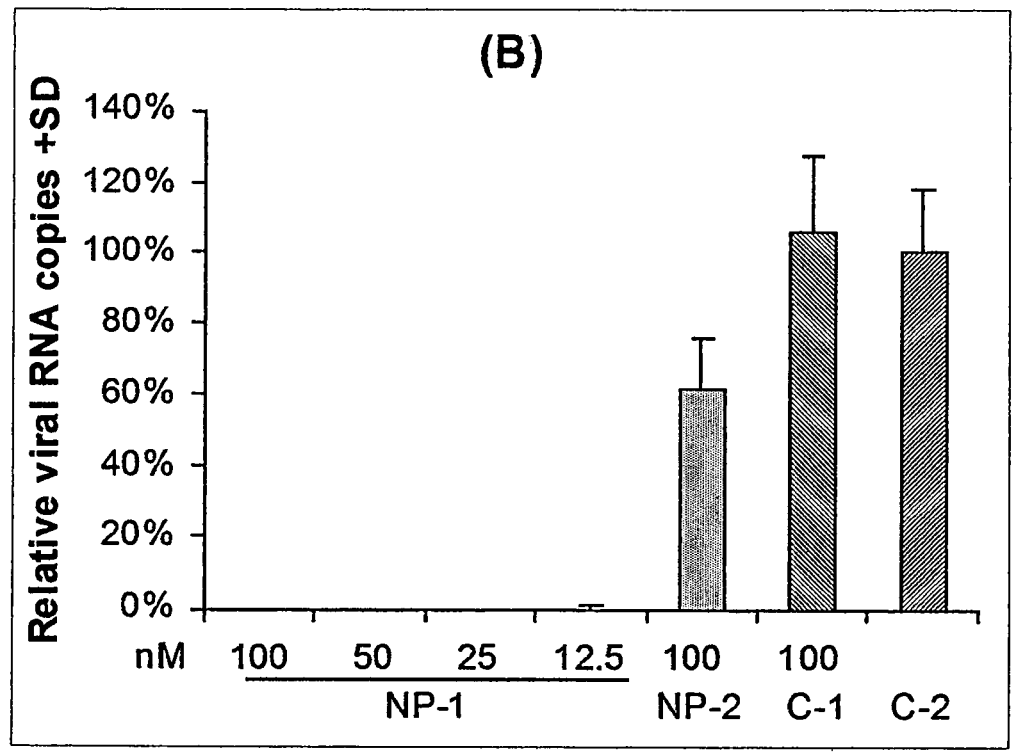
Figure 5:
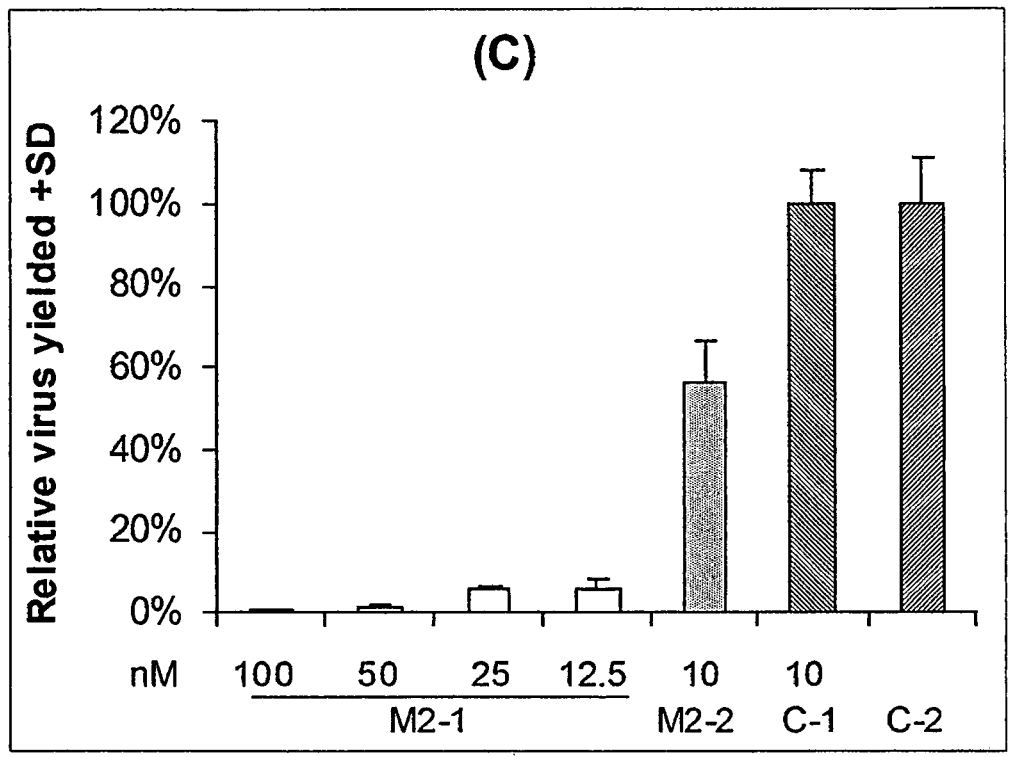
Figure 5:
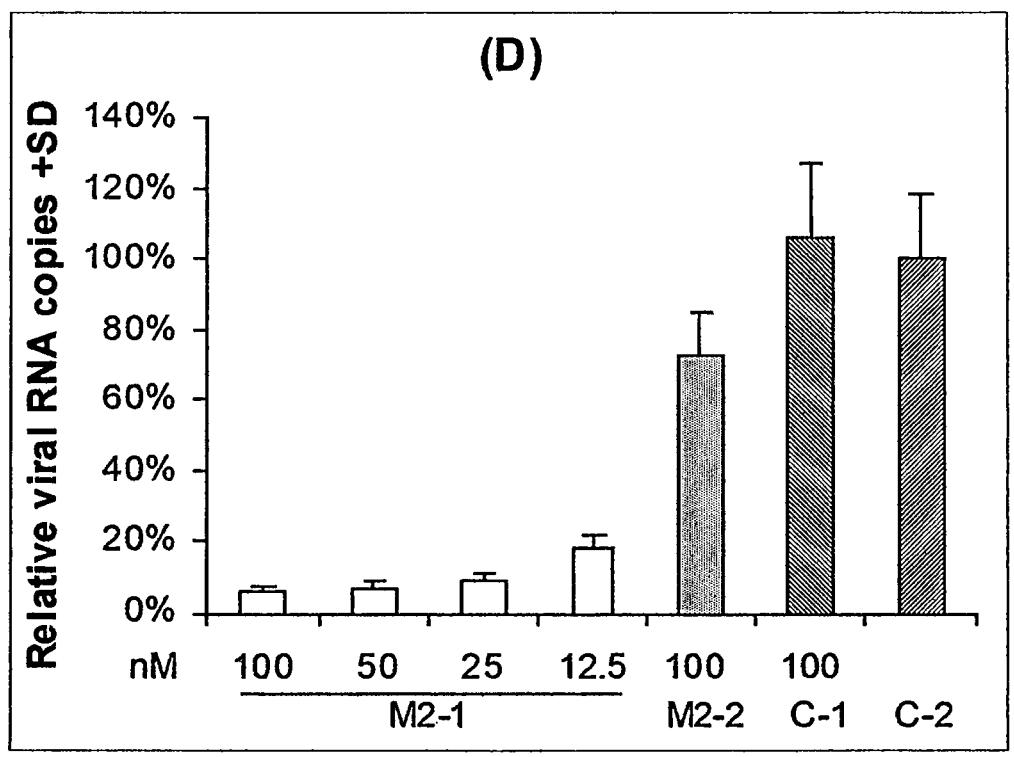

Additional siRNA duplexes against several influenza A H5N1 mRNA sequences were identified. These are shown in Table 19. Their positions are illustrated in FIG. 4.

TABLE 19

RNAi sequences targeting H5N1 avian influenza

| GENE | STRAND | SEQUENCE | SEQ ID NO: |
|---|---|---|---|
| NP-1 | Sense | 5'-GGAUCUUAUUUCUUCGGAG(dTdT)-3' | 256 |
|  | Antisense | 5'-CUCCGAAGAAAUAAGAUCC-(dTdT)-3' | 257 |
| NP-2 | Sense | 5'-UAUGAGAGAAUGUGCAACA(dTdT)-3' | 258 |
|  | Antisense | 5'-UGUUGCACAUUCUCUCAUA(dTdT)-3' | 259 |
| M2-1 | Sense | 5'-ACAGCAGAAUGCUGUGGAU(dTdT)-3' | 260 |
|  | Antisense | 5'-AUCCACAGCAUUCUGCUGU-(dTdT)-3' | 261 |
| M2-2 | Sense | 5'-CUGAGUCUAUGAGGGAAGA(dTdT)-3' | 262 |
|  | Antisense | 5'-UCUUCCCUCAUAGACUCAG(dTdT)-3' | 263 |

Combinations of siRNA

Several embodiments of the invention provide pharmaceutical compositions containing two or more oligonucleotides or polynucleotides each of which includes a sequence targeting genes in the genome of a respiratory virus. Related embodiments provide methods of treating cells, and methods of treating respiratory viral infections, using the combinations, as well as uses of such combination compositions in the manufacture of pharmaceutical compositions intended to treat respiratory viral infections. The individual polynucleotide components of the combination may target different portions of the same gene, or different genes, or several portions of one gene as well as more than one gene, in the genome of the viral pathogen. An advantage of using a combination of oligonucleotides or polynucleotides is that the benefits of inhibiting expression of a given gene are multiplied in the combination. Greater efficacy is achieved in knocking down a gene or silencing a viral genome by use of multiple targeting sequences. Enhanced efficiency in inhibiting viral replication is achieved by targeting more than one gene in the viral genome.

Pharmaceutical Compositions

The targeting polynucleotides of the invention are designated "active compounds" or "therapeutics" herein. These therapeutics can be incorporated into pharmaceutical compositions suitable for administration to a subject.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in textbooks such as Remington's Pharmaceutical Sciences, Gennaro A R (Ed.) 20$^{th}$ edition (2000) Williams & Wilkins P A, USA, and Wilson and Gisvold's Textbook of Organic Medicinal and Pharmaceutical Chemistry, by Delgado and Remers, Lippincott-Raven., which are incorporated herein by reference. Preferred examples of components that may be used in such carriers or diluents include, but are not limited to, water, saline, phosphate salts, carboxylate salts, amino acid solutions, Ringer's solutions, dextrose (a synonym for glucose) solution, and 5% human serum albumin. By way of nonlimiting example, dextrose may used as 5% or 10% aqueous solutions. Liposomes and non-aqueous vehicles such as fixed oils may also be used. The use of such media and agents for pharmaceutically active substances is well known in the art. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral, nasal, inhalation, transdermal (topical), transmucosal, and rectal administration. Solutions or suspensions used for parenteral, intravenous, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose.

For administration by inhalation, the compounds are delivered in the form of an aerosol spray from pressured container or dispenser which contains a suitable propellant, e.g., a gas such as carbon dioxide, or a nebulizer.

In one embodiment, the active compounds are prepared with carriers that will protect the compound against rapid elimination from the body, such as a controlled release formulation, including implants and microencapsulated delivery systems. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release pharmaceutical active agents over shorter time periods. Advantageous polymers are biodegradable, or biocompatible. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811. Sustained-release preparations having advantageous forms, such as microspheres, can be prepared from materials such as those described above.

The siRNA polynucleotides of the invention can be inserted into vectors and used as gene therapy vectors. Gene therapy vectors can be delivered to a subject by any of a number of routes, e.g., as described in U.S. Pat. No. 5,703,055. Delivery can thus also include, e.g., intravenous injection, local administration (see U.S. Pat. No. 5,328,470) or stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a kit, e.g., in a container, pack, or dispenser together with instructions for administration.

Also within the invention is the use of a therapeutic in the manufacture of a pharmaceutical composition or medicament for treating a respiratory viral infection in a subject.

Delivery

In several embodiments the siRNA polynucleotides of the invention are delivered into cells in culture by liposome-mediated transfection, for example by using commercially available reagents or techniques, e.g., Oligofectamine™, LipofectAmine™ reagent, LipofectAmine 2000™ (Invitrogen), as well as by electroporation, and similar techniques. Additionally siRNA polynucleotides are, is delivered to animal models, such as rodents or non-human primates, through inhalation and instillation into the respiratory tract. Additional routes for use with animal models include intravenous (IV), subcutaneous (SC), and related routes of administration. The pharmaceutical compositions containing the siRNAs include additional components that protect the stability of siRNA, prolong siRNA lifetime, potentiate siRNA function, or target siRNA to specific tissues/cells. These include a variety of biodegradable polymers, cationic polymers (such as polyethyleneimine), cationic copolypeptides such as histidine-lysine (HK) polypeptides see, for example, PCT publications WO 01/47496 to Mixson et al., WO 02/096941 to Biomerieux, and WO 99/42091 to Massachusetts Institute of Technology), PEGylated cationic polypeptides, and ligand-incorporated polymers, etc. positively charged polypeptides, PolyTran polymers (natural polysaccharides, also known as scleroglucan), a nano-particle consists of conjugated polymers with targeting ligand (TargeTran variants), surfactants (Infasurf; Forest Laboratories, Inc.; ONY Inc.), and cationic polymers (such as polyethyleneimine). Infasurf® (calfactant) is a natural lung surfactant isolated from calf lung for use in intratracheal instillation; it contains phospholipids, neutral lipids, and hydrophobic surfactant-associated proteins B and C. The polymers can either be uni-dimensional or multi-dimensional, and also could be microparticles or nanoparticles with diameters less than 20 microns, between 20 and 100 microns, or above 100 micron. The said polymers could carry ligand molecules specific for receptors or molecules of special tissues or cells, thus be used for targeted delivery of siRNAs. The siRNA polynucleotides are also delivered by cationic liposome based carriers, such as DOTAP, DOTAP/Cholesterol (Qbiogene, Inc.) and other types of lipid aqueous solutions. In addition, low percentage (5-10%) glucose aqueous solution, and Infasurf are effective carriers for airway delivery of siRNA[30].

Using fluorescence-labeled siRNA suspended in an oral-tracheal delivery solution of 5% glucose and Infasurf examined by fluorescence microscopy, it has been shown that after siRNA is delivered to mice via the nostril or via the oral-tracheal route, and washing the lung tissues the siRNA is widely distributed in the lung (see co-owned WO 2005/01940, incorporated by reference herein in its entirety). The delivery of siRNA into the nasal passage and lung (upper and deeper respiratory tract) of mice was shown to successfully silence the indicator genes (GFP or luciferase) delivered simultaneously with the siRNA in a plasmid harboring a fusion of the indicator gene and the siRNA target (see co-owned WO 2005/01940). In addition, experiments reported by the inventors, working with others, have demonstrated that siRNA species inhibit the replication of SARS coronavirus, thus relieving the lung pathology, in the SARS-infected rhesus monkeys[30].

siRNA Recombinant Vectors

Another aspect of the invention pertains to vectors, preferably expression vectors, containing an siRNA polynucleotide of the invention. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g. in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel (1990) Gene Expression Technology: Methods in Enzymology 185, Academic Press, San Diego, Calif. Regulatory sequences include those that direct constitutive expression of a nucleotide sequence in many types of host cell and those that direct expression of the nucleotide sequence only in certain host cells (e.g., tissue-specific regulatory sequences). In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J* 6: 187-195). When used in mammalian cells, the expression vector's control functions are often provided by viral regulatory elements. For example, commonly used promoters are derived from polyoma, Adenovirus 2, cytomegalovirus and Simian Virus 40. Additional vectors include minichromosomes such as bacterial artificial chromosomes, yeast artificial chromosomes, or mammalian artificial chromosomes. For other suitable expression systems for both prokaryotic and eukaryotic cells. See, e.g., Chapters 16 and 17 of Sambrook et al., Molecular Cloning: A Laboratory Manual. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type such as a cell of the respiratory tract. Tissue-specific regulatory elements are known in the art. The invention further provides a recombinant expression vector comprising a DNA molecule of the invention cloned into the expression vector. The DNA molecule is operatively linked to a regulatory sequence in a manner that allows for expression (by transcription of the DNA molecule) of an RNA molecule that includes an siRNA targeting a viral RNA. Regulatory sequences operatively linked to a nucleic acid can be chosen that direct the continuous expression of the RNA molecule in a variety of cell types, for instance viral promoters and/or enhancers, or regulatory sequences can be chosen that direct constitutive, tissue specific or cell type specific expression of antisense RNA.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (2001), Ausubel et al. (2002), and other laboratory manuals.

Methods of Assaying for Virus Titer or Amount

In practicing the present invention assaying for the virus may be carried out by several procedures. Among these are, by way of nonlimiting example, immunoblot (Western blot), immunoprecipitation (I.P.), and combined reverse transcription-polymerase chain reaction (RT-PCR) assay, and the like. Such procedures measure the reduction of the synthesis of the targeted mRNAs or their protein products that may present in the lysate or supernatant of the transfected tissue cultures. Likewise, these assays may be used as diagnostic procedures, to measure the reduction of the synthesis of the targeted mRNAs or their products that may present in homogenized tissue samples, nasopharyngeal washes, secretions, obtained from infected animals or human subjects.

In the RT-PCR assay methods the synthesis of viral genomic RNA is detected using primers complementary to the sequence across the junction between NS1 and NS2 ORFs. The result of this RT-PCR using NS1/NS2 primers will reflect the synthesis of the whole genomic RNA.

The methods further include assays wherein siRNA-induced interference of viral replication in tissue culture is measured by quantitative real-time PCR (RTQ-PCR), TCID50, viral plaque assay, immunofluorescence assay, and immunohistochemistry, and the like, as known to a worker of skill in the field of the invention. In addition the methods further include assaying for the presence of virus, employing the said TCID50 method to monitor the inhibition of viral replication in tissue culture, wherein the viral titer is measured by any kind of cell pathogenic endpoints, including by way of nonlimiting example, cell fusion, cytopathic effect (CPE), cell adsorption, and the like.

The methods further include assays wherein the said siRNA-mediated viral replication in tested animals is measured by RTQ-PCR, pathology, immunohistochemistry, and re-isolation of virus, and the like.

Primers are designed for RT-PCR detection that is used to measure the reduction of mRNA synthesis by RNAi. The RT reaction is initiated by hexamer or poly-dT primers; and PCR is performed by using upstream and downstream primers specific for each gene targeted by siRNA.

For the detection of genomic RNA synthesis, a pair of primers (up and down) is designed correspondent to sequences within NS1 and NS2 ORFs. The purpose of using "joint-crossing" primers, instead of primers complementary to either end of the viral genome, is to avoid the big size of whole RNA transcripts (around 15K-nt of length) that is not easy to handle. The product of this RT-PCR, by the design, will reflect the synthesis of the whole genomic RNA.

Primers that have been identified, and the sizes of the RT-PCR products, are listed below in Tables 20, 21, and 22.

TABLE 20

Primers for RSV strain A2 (subgroup A).

| GENE | STRAND | POSITIONS | SEQUENCE | SEQ ID NO: |
|---|---|---|---|---|
| Genome-NS1 | Up | 399-419 | CCTAATGGTCTACTAGATGAC | 264 |
| Genome-NS2 | Down | 738-718 | TGTGTGTTATGATGTCTCTGG | 265 |
| L | Up | 8773-8793 | GACATACAAGAGTATGACCTC | 266 |
| L | Down | 9410-9390 | ATCCGCATCTTAAGCCTAAGC | 267 |
| F | Up | 5786-5806 | AGGCTATCTTAGTGCTCTGAG | 268 |
| F | Down | 6205-6185 | GATAAGCTGACTAGAGCCTTG | 269 |
| G | Up | 4727-4747 | GAAAGGACCTGGGACACTCTC | 270 |
| G | Down | 5394-5374 | ATGGTTGGCTCTTCTGTGGGC | 271 |
| P | Up | 2356-2376 | TTGCTCCTGAATTCCATGGAG | 272 |
| P | Down | 2809-2789 | GCCACTACTAATGTGTGAAGC | 273 |

TABLE 21

Primers for RSV strain B2 (subgroup B).

| GENE | STRAND | POSITIONS | SEQUENCE | SEQ ID NO: |
|---|---|---|---|---|
| Genome-NS1 | Up | 280-300 | CAAGCAGTGAAGTGTGCCCTG | 274 |
| Genome-NS2 | Down | 849-829 | CTCCCTACTTTGTGCAGTAGC | 275 |
| L | Up | 8866-8886 | AGTGATGTAAAGGTGTACGCC | 276 |
| L | Down | 9343-9323 | TGCTAAGGCTGATGTCTTTCC | 277 |
| F | Up | 5773-5793 | ATGTAGTGCAGTTAGCAGAGG | 278 |
| F | Down | 6298-6278 | GCTCTGTTGATTTACTATGGG | 279 |
| G | Up | 4843-4863 | ACCTCTCTCATAATTGCAGCC | 280 |
| G | Down | 5301-5281 | GTTTGTGGGTTTGATGGTTGG | 281 |
| P | Up | 2420-2440 | AAGGGCAAGTTCGCATCATCC | 282 |
| P | Down | 2946-2926 | TTCCTAAGTCTTGCCATAGCC | 283 |

TABLE 22

Size of PCR products

| Gene | Primers SEQ ID NOS: | Product (bp) |
|---|---|---|
| A2-genome | 264 & 265 | 340 |
| A2-L | 266 & 267 | 638 |
| A2-F | 268 & 269 | 420 |
| A2-G | 270 & 271 | 668 |
| A2-P | 272 & 273 | 454 |

TABLE 22-continued

| Size of PCR products | | |
|---|---|---|
| Gene | Primers SEQ ID NOS: | Product (bp) |
| B1-genomic | 274 & 275 | 550 |
| B1-L | 276 & 277 | 478 |
| B1-F | 278 & 279 | 526 |
| B1-G | 280 & 281 | 459 |
| B1-P | 282 & 283 | 527 |

EXAMPLES

Example 1

Effect of anti-H5N1 Influenza A siRNA Molecules on Cell Culture

This Example reports evaluation of the inhibitory effects of siRNAs on H5N1 infected cells in culture.

Design and Synthesis of siRNAs

Two siRNAs respectively targeting the NP(NP-1 & NP-2; Table 19, SEQ ID NOS:) and M2 (M2-1 & M2-2; Table 19, SEQ ID NOS:) genes of H5N1 were developed. These siRNAs target sequences conserved in several strains of H5N1 virus (e.g. gi|47834945_10-1506, gi|8452827_1-1497, gi|13925158_46-1542, gi|61927237_46-1542, gi|59940391_44->1535, gi|9802277_46-1542). The ds-siRNA, fluorescein-labeled at the 5'-sense strand, were chemically synthesized by Proligo BioTech Ltd (Paris, France). Their anti-H5N1 effects were detected in siRNA-transfected MDCK cells (Madin-Darby canine kidney; ATCC® Number: CCL-34, Manassas, Va.) infected with H5N1 virus. The inhibition of H5N1 was determined by cytopathic effects (CPE), back titration of the released virus in culture media by standard $TCID_{50}$ (50% tissue culture infectious dose) protocol and quantification of intracellular viral RNA using real-time RT-PCR as described below.

Cell Culture, siRNA Transfection and H5N1 Virus Infection

MDCK cells were cultured and maintained in MEM medium with 10% fetal bovine serum (FBS, Invitrogen). Around 5000 cells were set in each well of a 96-well plate for viral infection and replication assay. The cells were transected with 100, 50, 25 and 12.5 nM siRNA mixing with 0.5 μl of Lipofectamine 2000 (Invitrogen, CA). Unrelated siRNA targeting luciferase (GL21) or siRNAs targeting SARS coronavirus (C-1) and transfectant Lipofectamine 2000 alone (C-2) were included in the experiments as negative controls. Six hours after transfection, the culture medium was removed and the cells were washed twice with PBS before H5N1 virus infection. One hundred microliters of 100 $TCID_{50}$H5N1 virus (strain: A/Hong Kong/486/97)[7] diluted in MEM with 1% FBS was added to the transfected cells. Culture supernatant and the cells were respectively collected at 12, 16 and 24 hours post-infection for detection of released virus titers and intracellular viral RNA copies. Twenty-four hours after infection, the CPEs were observed and recorded under phase-contrast microscopy. The experiments were performed in triplicate and repeated at least three times.

Quantitative RT-PCR

Q-RT-PCR is carried out as follows. Total intracellular RNA was isolated using RNeasy Mini kit (Qiagen, Germany), in accordance with the manufacturer's instructions. The reverse-transcription experiments were performed by oligo-dT priming using ThermoScript RT-PCR systems (Invitrogen, CA). Real-time PCR was then performed using the primers shown in Table 23.

TABLE 23

| H5N1 Primers for Q-RT-PCR | | | |
|---|---|---|---|
| GENE | PRIMER | SEQUENCE | SEQ ID NO: |
| NP | forward | 5'-GACCAGGAGTGGAGGAAACA-3 | 284 |
| NP | reverse | 5'-CGGCCATAATGGTCACTCTT-3' | 285 |
| M2 | forward | 5'-CGTCGCTTTAAATACGGTTTG-3' | 286 |
| M2 | reverse' | 5'-CGTCAACATCCACAGCATTC-3 | 287 |

Five μl of the RT product (template), 1 μl of each forward and reverse primers (final concentration 500 nM), 2 μl of 255 mM $MgCl_2$, and 9 μl of $H_2O$ were mixed with 2 μl of SYBR Green I Master Mix (Roche, USA) Master Mix and real-time quantification was carried out using an ABI7900 Sequence Detection System. The PCR conditions were: 50° C. for 5 min, 95° C. for 10 min, then 40 cycles of 95° C. for 10 sec, 61° C. for 5 sec and 72° C. for 5 sec. Copies of β-actin were also measured as an internal control. The copy numbers of intracellular viral RNA per 1000 copies of β-actin were calculated and expressed as relative viral RNA copies as compared to the untreated control (copies of treated/copies of untreated×100%).

Measurement of Viral Titers

The virus titers in cultures with or without siRNA treatment were tested as follows. Briefly, the conditioned medium from infected cells was diluted in 10-fold serial steps in MEM with 1% FBS. Each dilution was used for infecting cells according to the standard $TCID_{50}$ protocol. Briefly, cells were set in 96-well dishes sixteen hours before infection. Seventy-two hours post-infection, CPEs were observed under phase-contrast microscopy and CPE-positive (CPE+) cells determined. $TCID_{50}$ is then evaluated as follows:

$$h = \frac{(\%\text{ wells }(CPE+)\text{ at dilution above }50\%) - 50\%}{(\%\text{ wells }(CPE+)\text{ at dilution above }50\%) - (\%\text{ wells }(CPE+)\text{ at dilution below }50\%)},$$

where h=an interpolated $\log_{10}$ value of a dilution step, which is added to the $\log_{10}$ step above the 50% value. The infectious viral titer was calculated and expressed as relative virus yielded as compared to the untreated control (titer of treated/titer of untreated×100%).

Results

The siRNA NP-1 (Table 19) treatment reduced H5N1 virus production in culture media (FIG. 5, panel A) and replication of viral RNA copies in the cells (FIG. 5, panel B) by over 99% at concentrations of 12.5 to 100 nM while treatment with siRNA targeting NP-2 (Table 19) inhibited only about 60% of the virus growth in the cell cultures at concentration of 100 mM. By contrast, unrelated siRNA treated control (C-1) and carrier treated control (C-2) did not significantly inhibit the virus growth as compared to the untreated control.

Treatment with siRNA directed against M2-1 (Table 19) also exhibited about 80 to 94% of inhibitory effects to the virus growth (FIG. 5, panel C) and replication of viral RNA ((FIG. 5, panel D) at different concentrations, whereas M2-2 showed around 60% inhibitory effect at concentration of 100 nM but not at the lower concentrations tested.

Figure 6:
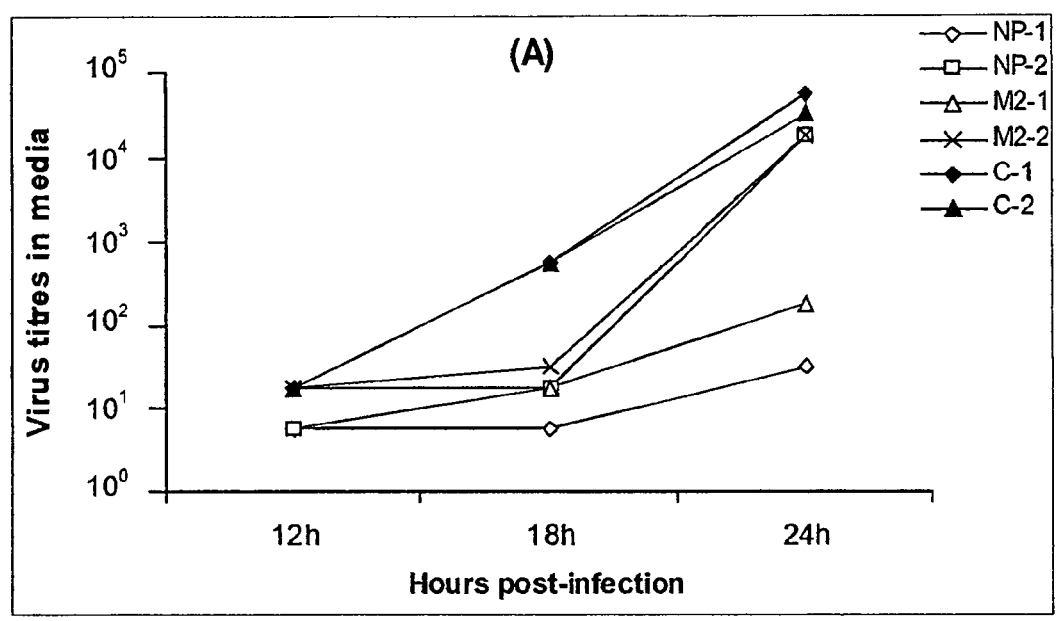
Figure 6:
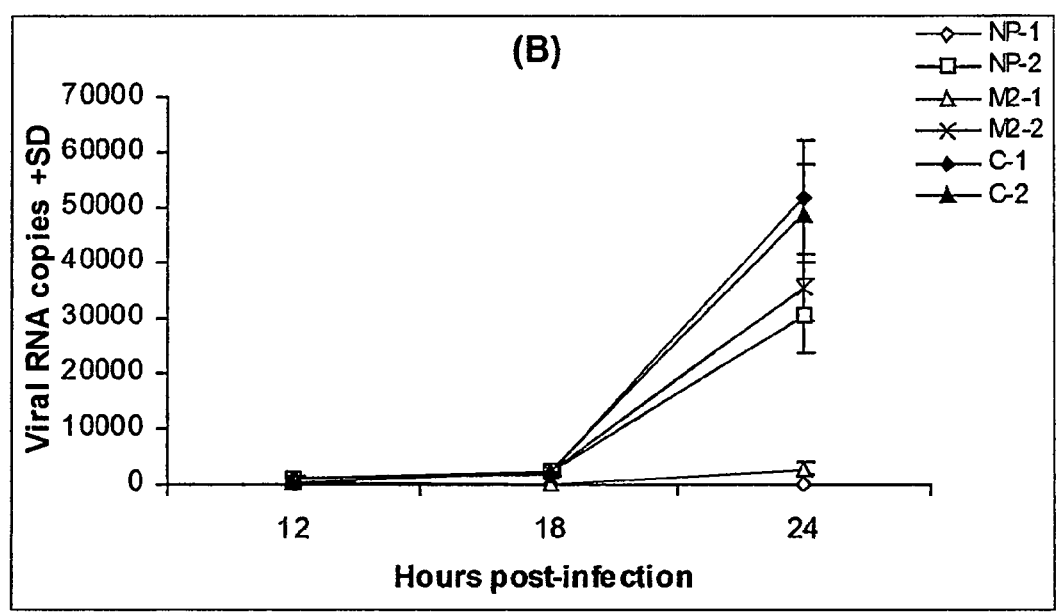

In a second experiment, the cells in culture were treated with various siRNAs at 50 nM. The virus produced in the culture supernatant media was collected at three time points. The samples were titrated by determining the tissue culture infection dose required to infect 50% of the cells in the culture (TCID$_{50}$) (FIG. 6, panel A; note this is presented on a logarithmic ordinate scale). The number of viral RNA copies/1000 copies of β-actin was determined by real-time RT-PCR (FIG. 6, panel B). Unrelated siRNA (C-1) and transfectant (C-2) were applied in the experiments as controls. It is seen that NP-1 and NP-2 siRNAs are highly effective in inhibiting the growth of viral particles and the increase in viral RNA. Use of M1-1 and M2-2 siRNAs was partially effective in preventing viral replication.

The results in this Example demonstrate that various siRNAs directed against different genes in the H5N1 genome are highly effective in inhibiting viral replication in infected cells grown in culture.

Example 2

Combinations of siRNA Directed against H5N1 Influenza A

Combinations of siRNAs directed against different genes in the H5N1 genome were identified in order to provide effective anti-H5N1 activity. This Example presents two such combinations.

```
Combination A:
NP-1:
5'-GGAUCUUAUUUCUUCGGAG(dTdT)-3',   (SEQ ID NO:256)

M2-1:
5'-ACAGCAGAAUGCUGUGGAU(dTdT)-3',   (SEQ ID NO:260)
and

HA-1:
5'-TGGTAGATGGTTGGTATGG(dtdt)-3'.   (SEQ ID NO:221,
                                    bases 3-21,
                                    plus 3'
                                    terminal
                                    (dtdt))
Combination B:
NP-1:
5'-GGAUCUUAUUUCUUCGGAG(dTdT)-3',   (SEQ ID NO:256)

M2-1:
5'-ACAGCAGAAUGCUGUGGAU(dTdT)-3',   (SEQ ID NO:260)
and

NA-1:
5'-TCTGTATGGTAATTGGAAT(dtdt)-3'.   (SEQ ID NO:230,
                                    bases 3-21,
                                    plus 3'
                                    terminal
                                    (dtdt))
```

Example 3

Inhibition of Target Genes and Viral Replication in Cells In vitro by siRNA

In this Example optimally effective siRNAs, and optimally effective combinations of siRNAs, targeting different respiratory viral genes in their ability to silence the cognate target gene(s) or inhibiting viral replication, are identified by experiments in cell culture. The siRNAs effective in vitro are to be candidates to be further tested and used in vivo.

Cultured permissive cell lines, such as, by way of nonlimiting example, A549 (ATCC® Number: CCL-185™, a type II alveolar epithelial lung carcinoma cell line) are infected with an RSV viral strain or an influenza A strain such as H5N1, and then are transfected with various siRNAs either individually or in combination. In the case of combinations, two siRNAs targeting one single gene, or a combination of siRNAs targeting two or more genes are to be employed. The total siRNA dosage of single or combination of siRNAs is kept the same. In different experimental protocols, the siRNA transfection is performed several hours prior to the RSV or influenza A infection, or simultaneously with viral infection, or several hours post-infection. These different procedures provide information on whether the tested siRNAs exhibit prophylactic and/or therapeutic effects at the cellular level.

The extent of inhibition of target gene(s), or the inhibition of viral replication is assayed in a variety of ways. Nonlimiting examples of assays include the following procedures:

1) Immunoblot (Western) is performed using cell lysates and RSV or influenza A specific antibody against a given viral antigen.

2) Immunoprecipitation (IP) is performed using cell lysates and RSV or influenza A specific antibody against single gene products as above.

3) rvtr-PCR is performed to demonstrate the inhibition of mRNA transcription or the inhibition of viral RNA replication. Special primers are designed to detect transcripts of targeted gene or detect whether a tested siRNA oligo(s) can also target the genomic RNA.

4) The measurement of cell-fusion-based TCID50 could be used to compared cell cultures treated with specific siRNA of unrelated control siRNA, to monitor the inhibition of viral replication.

5) Immunofluorescence or immunohistochemistry also can be used to titrate virus titers, thus to monitor the siRNA-mediated inhibition of viral replication.

Example 4

Inhibition of Target Genes by siRNA in Small Animal Models

In this Example various siRNAs, individually or their combinations, are examined to determine their efficacy in treating RSV or avian influenza H5N1 in animal models. An RSV or influenza H5N1 strain is used to infect the test animals through the airway, by inhalation or instillation. The siRNAs are delivered through the same route, and are applied prior to, simultaneously with, or after RSV or influenza H5N1 infection. By varying siRNA delivering times, it is possible to get information of the efficacy of siRNAs in inhibiting RSV or influenza H5N1 replication in the test animal, reducing RSV or influenza H5N1-induced pathology, and relieving the RSV or influenza H5N1-like symptoms, as well as the information on whether RSV or influenza H5N1-specific siRNAs demonstrate prophylactic or therapeutic effect on experimental RSV or influenza H5N1 infection in animals.

Although RSV and influenza H5N1 can infect a wide range of animal species, mice and cotton rats are conventionally used in RSV or influenza H5N1 animal model studies. Infection of rodents usually results in a low to moderate level of viral replication that peaks at 4 days and is quickly clear. These animals do not show overt respiratory tract disease, but show lung pathology. At high doses of virus infection they show weigh loss, changes in pulmonary function, and ruffled fur that is indicative of disease.

Same diagnostic assays as described above in Example 3 are used to monitor the siRNA-mediated gene-silencing and inhibition of RSV or influenza H5N1 infection on samples taken from the animals, such as nasal, buccal or pharyngeal swabs. Additionally, lung pathology, lung immunohistochemistry, and symptom observation are carried out to determine the efficacy of siRNAs on RSV or influenza H5N1 infection in vivo.

Example 5

Inhibition of Target Genes by siRNA in Non-human Primate Model

This Example describes studies of siRNA-mediated inhibition of RSV or influenza H5N1 viral replication in non-human primates. The efficacy and safety of dose administration are major goals of this study.

Based upon our protocol used on rhesus monkey model for another respiratory disease, SARS, the dose of siRNA of up to 30 mg/kg weigh is tolerable, showing no signs of toxicity to the animals[22]. The respiratory delivery (by inhalation and instillation) of siRNAs that had been pre-screened by in non-primate mammals showed substantial effect on inhibition of viral replication, and reduction of virus-induced pathology and disease-like symptoms. For the present RSV or influenza H5N1 study, the same delivery route is used, and similar dosages of siRNA are delivered.

In addition to the experiments described for small animal study (Example 4), the following assays are readily performed in primates and contribute to a more direct assessment of therapeutic efficacy.

1) Virus shedding: Viral shedding is measured using nasopharynx wash samples of infected monkeys. The virus yield is titrated by either TCID50 (cell-fusion based) and/or immunofluorescence assay.

2) RTQ-PCR of nasopharynx wash samples: to monitor changes of viral genome copy numbers.

3) Symptom monitoring: it is likely to find bronchiolitis symptoms, as observed in human infant patients.

Although the invention has been described and illustrated with respect to various exemplary embodiments thereof, equivalent embodiments and various other alterations, additions and omissions may be made therein and thereto without departing from the spirit and scope of the present invention.

References

1. Holmes, E. C. 2004, Science, 303: 1787-1788.
2. Abbott, A. 2003, Nature, 424: 121-123.
1. Yuen K Y, et al. *Lancet.* 351:467-71. 1998.
2. Claas E C, et al. *Lancet.* 351:472-7. 1998
3. Peiris J S., . . . Yuen K Y, et al. *Lancet.* 363:617-9. 2004.
4. World Health Organization http://www.who.int/csr/disease/avian_influenza/country/cases_table_2005_06_28/en/index.html
5. World Health Organization http://www.who.int/csr/disease/avian_influenza/
6. Li K S, . . . , Yuen K Y, et al. *Nature.* 430:209-13. 2004.
7. Chen H, et al. *Nature.* 436:191-2. 2005.
8. Liu J, et al. *Science.* www.sciencexpress.org/6 Jul. 2005/Page 1/10.1126/science.1115273. 2005.
9. Bridges C B, et al. *J Infect Dis* 181:344-8. 2000.
10. Ungchusak K, et al. *N Engl J Med* 352:333-40. 2005
11. World Health Organization http://www.who.int/csr/resources/publications
12. Collins, R. M. et al, 2001, *Virology* (4th, ed), p. 1443-1485.
13. www.medimmun.com
14. Smith, D. W. et al, 1991, N Engl. J. Med, P 325: 24-29
15. Sharp, P. A. 2001, Genes & Development, 15: 485-490.
16. Tuschl, T. 2001, Chembiochem, 2: 239-245.
17. Dykxhoorn, D. M. et al, 2003, Nat Rev Mol Cell Biol 4(6):457-67.
18. Elbashir, S. M. et al, 2001, Nature, 411: 494-498.
19. Schiwarz, D. S. et al, 2003, Cell, 115: 199-208.
20. Khvorova, A. et al, 2003, Cell, 115: 209-216.
21. Reynolds, A. et al, 2004, Nat. Biotechnology, 22: 326-330.
22. Pellino, J. L., & Sontheimer, E. J., 203, Cell, 115: 132-133.
23. Ma, J. B. et al, 2004, Nature, 429: 318-322.
24. Ahlquist, P, 2002, Science, 296: 1270-1273.
25. Calain, P. & Roux, L. 1993, J. Vol., 67: 4822-4830.
26. Barik, S. 2004, Virus Research, 102: 27-35.
27. Bitko, V. & Barik, S. 2004, Nature Medicine, 11, 50-55.
28. Gitlin, L. et al, Nature, 418: 430-434.
29. Zheng, B. J. et al, 2004, Antiviral Therapy, 9: 365-374.
30. Li B. J. et al, 2005, Nature Medicine, 11, 944-951.

We claim:

1. An isolated siRNA molecule selected from the group consisting of paired sequences consisting of SEQ ID No. 258 and its complementary sequence, SEQ ID No. 259, and paired sequences consisting of SEQ ID No. 262 and its complementary sequence, SEQ ID No 263.

2. The siRNA molecule of claim 1 wherein the group further includes the paired sequences consisting of SEQ ID No. 260 and its complementary sequence, SEQ ID No. 261.

3. The siRNA molecule of claim 1 further including a dinucleotide overhang bound to the 3' end of both sequences.

4. The siRNA molecule of claim 3 wherein the dinucleotide overhang comprises dTdT.

5. The siRNA molecule of claim 2 further including a dinucleotide overhang bound to the 3' end of both sequences.

6. The siRNA molecule of claim 5 wherein the dinucleotide overhang comprises dTdT.

7. A pharmaceutical composition comprising the siRNA molecule of claim 1 and a pharmaceutically acceptable carrier.

8. The pharmaceutical composition of claim 7 wherein the carrier comprises a synthetic polymer, a liposome, dextrose, glucose, a surfactant, or a combination of any two or more of them.

9. The pharmaceutical composition of claim 7 wherein the carrier comprises a cationic polymer.

10. The pharmaceutical composition of claim 7 wherein the carrier is selected from the group consisting of a histidine-lysine co-polymer, PEGylated polyethyleneimine, glucose, DOTAP, and DOTAP/cholesterol.

11. A pharmaceutical composition comprising the siRNA molecule of claim 2 and a pharmaceutically acceptable carrier.

12. The pharmaceutical composition of claim 11 wherein the carrier comprises a synthetic polymer, a liposome, dextrose, glucose, a surfactant, or a combination of any two or more of them.

13. The pharmaceutical composition of claim 11 wherein the carrier comprises a cationic polymer.

14. The pharmaceutical composition of claim 11 wherein the carrier is selected from the group consisting of a histidine-lysine co-polymer, PEGylated polyethyleneimine, glucose, DOTAP, and DOTAP/cholesterol.

15. A pharmaceutical composition comprising the siRNA molecule of claim 6 and a pharmaceutically acceptable carrier selected from the group consisting of a histidine-lysine co-polymer, PEGylated polyethyleneimine, glucose, DOTAP, and DOTAP/cholesterol.

16. A method of inhibiting replication of an H5N1 avian Influenza A virus in a cell infected with the virus comprising contacting the cell with the siRNA molecule of claim 1.

17. A method of inhibiting replication of an H5N1 avian Influenza A virus in a cell infected with the virus comprising contacting the cell with the siRNA molecule of claim 2.

18. A method of inhibiting replication of an H5N1 avian Influenza A virus in a cell infected with the virus comprising contacting the cell with the siRNA molecule of claim 6.

19. A method of inhibiting replication of an H5N1 avian Influenza A virus in a cell infected with the virus comprising contacting the cell with the pharmaceutical composition of claim 7.

20. A method of inhibiting replication of an H5N1 avian Influenza A virus in a cell infected with the virus comprising contacting the cell with the pharmaceutical composition of claim 11.

21. A method of inhibiting replication of an H5N1 avian Influenza A virus in a cell infected with the virus comprising contacting the cell with the pharmaceutical composition of claim 15.

* * * * *

UNITED STATES PATENT AND TRADEMARK OFFICE
CERTIFICATE OF CORRECTION

PATENT NO. : 8,691,781 B2  Page 1 of 1
APPLICATION NO. : 11/792179
DATED : April 8, 2014
INVENTOR(S) : Tang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 504 days.

Signed and Sealed this
Twenty-ninth Day of September, 2015

Michelle K. Lee
*Director of the United States Patent and Trademark Office*

SEQUENCE LISTING

<160> NUMBER OF SEQ ID NOS: 287

<210> SEQ ID NO 1
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 1
aatggggcaa ataagaattt g                                      21

<210> SEQ ID NO 2
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 2

```
aatggggcaa ataagaattt g                                              21
```

<210> SEQ ID NO 3
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 3

```
aagatggctc ttagcaaagt c                                              21
```

<210> SEQ ID NO 4
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 4

```
aattcctaga atcaataaag g                                              21
```

<210> SEQ ID NO 5
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 5

```
aagcttcacg aaggctccac a                                              21
```

<210> SEQ ID NO 6
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 6

```
aatgatatgc ctataacaaa t                                              21
```

<210> SEQ ID NO 7
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 7

```
aagataagag tgtacaatac t                                              21
```

<210> SEQ ID NO 8
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 8

```
aacatcctcc atcatggtta a                                              21
```

<210> SEQ ID NO 9
<211> LENGTH: 21
<212> TYPE: DNA
<213> ORGANISM: Artificial Sequence

```
<220> FEATURE:
<223> OTHER INFORMATION: Respiratory Syncytial Virus

<400> SEQUENCE: 9
aagtactaat ttagctggac a                                              21

<210> SEQ ID NO 10
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 10
aagattgcaa tgatcatagt t                                              21

<210> SEQ ID NO 11
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 11
aacattcatt ggtcttattt a                                              21

<210> SEQ ID NO 12
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 12
aaatgcgtac aacaaacttg c                                              21

<210> SEQ ID NO 13
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 13
aacaaacttg cataaaccaa a                                              21

<210> SEQ ID NO 14
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 14
aagaatttga taagtaccac t                                              21

<210> SEQ ID NO 15
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 15
aactaacgct ttggctaagg c                                              21
```

```
<210> SEQ ID NO 16
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 16
aataaatcaa ttcagccaac c                                              21

<210> SEQ ID NO 17
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 17
aactattaca caaagtagga a                                              21

<210> SEQ ID NO 18
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 18
aacaaagatc aacttctgtc a                                              21

<210> SEQ ID NO 19
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 19
aagaaatggg agaggtagct c                                              21

<210> SEQ ID NO 20
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 20
aattcaacta ttatcaaccc a                                              21

<210> SEQ ID NO 21
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 21
aacaatgaag aagaatccag c                                              21

<210> SEQ ID NO 22
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 22
```

```
aaataaagat ctgaacacac t                                              21

<210> SEQ ID NO 23
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 23
aaatatccac acccaaggga c                                              21

<210> SEQ ID NO 24
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 24
aaataaagat ctgaacacac t                                              21

<210> SEQ ID NO 25
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 25
aacatagaca agtccacaca c                                              21

<210> SEQ ID NO 26
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 26
aacaatagaa ttctcaagca a                                              21

<210> SEQ ID NO 27
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 27
aaacaaggac caacgcaccg c                                              21

<210> SEQ ID NO 28
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 28
aacttcactt ataattgcag c                                              21

<210> SEQ ID NO 29
<211> LENGTH: 21
<212> TYPE: DNA
<213> ORGANISM: Artificial Sequence
```

```
<220> FEATURE:
<223> OTHER INFORMATION: Respiratory Syncytial Virus

<400> SEQUENCE: 29
aaataagtgt aatggaacag a                                              21

<210> SEQ ID NO 30
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 30
aaacaatcga gccagaagag a                                              21

<210> SEQ ID NO 31
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 31
aaataagtgg agctgcagag t                                              21

<210> SEQ ID NO 32
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 32
aacaatcagc atgtgttgcc a                                              21

<210> SEQ ID NO 33
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 33
aagttacata ttcaatggtc c                                              21

<210> SEQ ID NO 34
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 34
aactaaatat aacacagtcc t                                              21

<210> SEQ ID NO 35
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 35
aatgcgtact acaaacttgc a                                              21
```

```
<210> SEQ ID NO 36
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 36
aaatgcgtac tacaaacttg c                                              21

<210> SEQ ID NO 37
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 37
aattaattct tctgaccaat g                                              21

<210> SEQ ID NO 38
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 38
aacaagcagt gaagtgtgcc c                                              21

<210> SEQ ID NO 39
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 39
aataataaca tctctcacca a                                              21

<210> SEQ ID NO 40
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 40
aatgtattgg cattaagcct a                                              21

<210> SEQ ID NO 41
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 41
aaataaggat cagctgctgt c                                              21

<210> SEQ ID NO 42
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 42
```
aacaaactat gtggtatgct a                                              21

<210> SEQ ID NO 43
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 43
aataaagggc aagttcgcat c                                              21

<210> SEQ ID NO 44
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 44
aacaaatgac aacattacag c                                              21

<210> SEQ ID NO 45
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 45
aatatgggtg cctatgttcc a                                              21

<210> SEQ ID NO 46
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 46
aacatactag tgaagcagat c                                              21

<210> SEQ ID NO 47
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 47
aaatacatcc atcacaatag a                                              21

<210> SEQ ID NO 48
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 48
aaacattctg taacaatact c                                              21

<210> SEQ ID NO 49
<211> LENGTH: 21
<212> TYPE: DNA
<213> ORGANISM: Artificial Sequence

```
<220> FEATURE:
<223> OTHER INFORMATION: Respiratory Syncytial Virus

<400> SEQUENCE: 49
aatctatagc acaaatagca c                                              21

<210> SEQ ID NO 50
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 50
aatattcatc atctctgcca a                                              21

<210> SEQ ID NO 51
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 51
aaagaaacca atgcaatgg a                                               21

<210> SEQ ID NO 52
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 52
aaacaaagct gtagtcagtc t                                              21

<210> SEQ ID NO 53
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 53
aaataagtgg agctgctgaa c                                              21

<210> SEQ ID NO 54
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 54
aacaatcagc atgtgttgct a                                              21

<210> SEQ ID NO 55
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 55
aaataacatc acagatgcag c                                              21
```

```
<210> SEQ ID NO 56
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 56
aatacctaca acagatggcc c                                          21

<210> SEQ ID NO 57
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 57
aatttagctt actgattcca a                                          21

<210> SEQ ID NO 58
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 58
aactaacaat gatacatgtg c                                          21

<210> SEQ ID NO 59
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 59
aatttagcat attgattcca a                                          21

<210> SEQ ID NO 60
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 60
aactaacaat tatacatgtg c                                          21

<210> SEQ ID NO 61
<211> LENGTH: 25
<212> TYPE: DNA
<213> ORGANISM: Artificial Sequence
<220> FEATURE:
<223> OTHER INFORMATION: Influenza A Virus

<400> SEQUENCE: 61
tctagatgga gtgaagcctc taatt                                      25

<210> SEQ ID NO 62
<211> LENGTH: 25
<212> TYPE: DNA
<213> ORGANISM: Artificial Sequence
<220> FEATURE:
<223> OTHER INFORMATION: Influenza A Virus

<400> SEQUENCE: 62
```
gccaatccag tcaatgacct ctgtt                                          25

<210> SEQ ID NO 63
<211> LENGTH: 25
<212> TYPE: DNA
<213> ORGANISM: Artificial Sequence
<220> FEATURE:
<223> OTHER INFORMATION: Influenza A Virus

<400> SEQUENCE: 63
tccataccag ggaaagtcct ccttt 25

<210> SEQ ID NO 64
<211> LENGTH: 25
<212> TYPE: DNA
<213> ORGANISM: Artificial Sequence
<220> FEATURE:
<223> OTHER INFORMATION: Influenza A Virus

<400> SEQUENCE: 64
gcagagcaga caaagctcta tcaaa 25

<210> SEQ ID NO 65
<211> LENGTH: 25
<212> TYPE: DNA
<213> ORGANISM: Artificial Sequence
<220> FEATURE:
<223> OTHER INFORMATION: Influenza A Virus

<400> SEQUENCE: 65
accaagaata gctactagat ccaaa 25

<210> SEQ ID NO 66
<211> LENGTH: 25
<212> TYPE: DNA
<213> ORGANISM: Artificial Sequence
<220> FEATURE:
<223> OTHER INFORMATION: Influenza A Virus

<400> SEQUENCE: 66
ggcaaagtgg aaggatggag ttctt 25

<210> SEQ ID NO 67
<211> LENGTH: 25
<212> TYPE: DNA
<213> ORGANISM: Artificial Sequence
<220> FEATURE:
<223> OTHER INFORMATION: Influenza A Virus

<400> SEQUENCE: 67
ggaaggatgg agttcttctg gacaa 25

<210> SEQ ID NO 68
<211> LENGTH: 25
<212> TYPE: DNA
<213> ORGANISM: Artificial Sequence
<220> FEATURE:
<223> OTHER INFORMATION: Influenza A Virus

<400> SEQUENCE: 68
gcaacaccaa gtgtcaaact ccaat 25

<210> SEQ ID NO 69
<211> LENGTH: 25
<212> TYPE: DNA
<213> ORGANISM: Artificial Sequence

```
<220> FEATURE:
<223> OTHER INFORMATION: Influenza A Virus

<400> SEQUENCE: 69
ggaacgtatg actacccgca gtatt                                            25

<210> SEQ ID NO 70
<211> LENGTH: 25
<212> TYPE: DNA
<213> ORGANISM: Artificial Sequence
<220> FEATURE:
<223> OTHER INFORMATION: Influenza A Virus

<400> SEQUENCE: 70
ccaatgggtc gttacaatgc agaat                                            25

<210> SEQ ID NO 71
<211> LENGTH: 19
<212> TYPE: DNA
<213> ORGANISM: Artificial Sequence
<220> FEATURE:
<223> OTHER INFORMATION: Influenza A Virus

<400> SEQUENCE: 71
gcaatagtca gtcttgtta                                                   19

<210> SEQ ID NO 72
<211> LENGTH: 19
<212> TYPE: DNA
<213> ORGANISM: Artificial Sequence
<220> FEATURE:
<223> OTHER INFORMATION: Influenza A Virus

<400> SEQUENCE: 72
gccggaatgg tcttacata                                                   19

<210> SEQ ID NO 73
<211> LENGTH: 19
<212> TYPE: DNA
<213> ORGANISM: Artificial Sequence
<220> FEATURE:
<223> OTHER INFORMATION: Influenza A Virus

<400> SEQUENCE: 73
ccagtcatga agcctcatt                                                   19

<210> SEQ ID NO 74
<211> LENGTH: 19
<212> TYPE: DNA
<213> ORGANISM: Artificial Sequence
<220> FEATURE:
<223> OTHER INFORMATION: Influenza A Virus

<400> SEQUENCE: 74
ggagctacaa taataccaa                                                   19

<210> SEQ ID NO 75
<211> LENGTH: 19
<212> TYPE: DNA
<213> ORGANISM: Artificial Sequence
<220> FEATURE:
<223> OTHER INFORMATION: Influenza A Virus

<400> SEQUENCE: 75
gctactagat ccaaagtaa                                                   19
```

-continued

<210> SEQ ID NO 76
<211> LENGTH: 19
<212> TYPE: DNA
<213> ORGANISM: Artificial Sequence
<220> FEATURE:
<223> OTHER INFORMATION: Influenza A Virus

<400> SEQUENCE: 76
ccaagtgtca aactccaat                                                19

<210> SEQ ID NO 77
<211> LENGTH: 19
<212> TYPE: DNA
<213> ORGANISM: Artificial Sequence
<220> FEATURE:
<223> OTHER INFORMATION: Influenza A Virus

<400> SEQUENCE: 77
gcgactgggc tcagaaata                                                19

<210> SEQ ID NO 78
<211> LENGTH: 19
<212> TYPE: DNA
<213> ORGANISM: Artificial Sequence
<220> FEATURE:
<223> OTHER INFORMATION: Influenza A Virus

<400> SEQUENCE: 78
cctagatgtc tggacttat                                                19

<210> SEQ ID NO 79
<211> LENGTH: 19
<212> TYPE: DNA
<213> ORGANISM: Artificial Sequence
<220> FEATURE:
<223> OTHER INFORMATION: Influenza A Virus

<400> SEQUENCE: 79
ccctagcact ggcaatcat                                                19

<210> SEQ ID NO 80
<211> LENGTH: 19
<212> TYPE: DNA
<213> ORGANISM: Artificial Sequence
<220> FEATURE:
<223> OTHER INFORMATION: Influenza A Virus

<400> SEQUENCE: 80
gggtcgttac aatgcagaa                                                19

<210> SEQ ID NO 81
<211> LENGTH: 25
<212> TYPE: DNA
<213> ORGANISM: Artificial Sequence
<220> FEATURE:
<223> OTHER INFORMATION: Influenza A Virus

<400> SEQUENCE: 81
gaccaatcct gtcacctctg actaa                                         25

<210> SEQ ID NO 82
<211> LENGTH: 25
<212> TYPE: DNA
<213> ORGANISM: Artificial Sequence
<220> FEATURE:
<223> OTHER INFORMATION: Influenza A Virus

<400> SEQUENCE: 82
accaatcctg tcacctctga ctaaa                                    25

<210> SEQ ID NO 83
<211> LENGTH: 25
<212> TYPE: DNA
<213> ORGANISM: Artificial Sequence
<220> FEATURE:
<223> OTHER INFORMATION: Influenza A Virus

<400> SEQUENCE: 83
cctgtcacct ctgactaaag ggatt                                    25

<210> SEQ ID NO 84
<211> LENGTH: 25
<212> TYPE: DNA
<213> ORGANISM: Artificial Sequence
<220> FEATURE:
<223> OTHER INFORMATION: Influenza A Virus

<400> SEQUENCE: 84
ccagaatgcc ctaaatggaa atgga                                    25

<210> SEQ ID NO 85
<211> LENGTH: 25
<212> TYPE: DNA
<213> ORGANISM: Artificial Sequence
<220> FEATURE:
<223> OTHER INFORMATION: Influenza A Virus

<400> SEQUENCE: 85
gccctaaatg gaaatggaga tccaa                                    25

<210> SEQ ID NO 86
<211> LENGTH: 25
<212> TYPE: DNA
<213> ORGANISM: Artificial Sequence
<220> FEATURE:
<223> OTHER INFORMATION: Influenza A Virus

<400> SEQUENCE: 86
actcagctac tcaaccggtg cactt                                    25

<210> SEQ ID NO 87
<211> LENGTH: 25
<212> TYPE: DNA
<213> ORGANISM: Artificial Sequence
<220> FEATURE:
<223> OTHER INFORMATION: Influenza A Virus

<400> SEQUENCE: 87
gcaactacca ccaacccact aatca                                    25

<210> SEQ ID NO 88
<211> LENGTH: 25
<212> TYPE: DNA
<213> ORGANISM: Artificial Sequence
<220> FEATURE:
<223> OTHER INFORMATION: Influenza A Virus

<400> SEQUENCE: 88
gcgattcaag tgatcctatt gttgt                                    25

<210> SEQ ID NO 89
<211> LENGTH: 25
<212> TYPE: DNA
<213> ORGANISM: Artificial Sequence

```
<220> FEATURE:
<223> OTHER INFORMATION: Influenza A Virus

<400> SEQUENCE: 89
cctattgttg ttgccgcaaa tatca                                    25

<210> SEQ ID NO 90
<211> LENGTH: 25
<212> TYPE: DNA
<213> ORGANISM: Artificial Sequence
<220> FEATURE:
<223> OTHER INFORMATION: Influenza A Virus

<400> SEQUENCE: 90
tgatattgtg gattcttgat cgtct                                    25

<210> SEQ ID NO 91
<211> LENGTH: 19
<212> TYPE: DNA
<213> ORGANISM: Artificial Sequence
<220> FEATURE:
<223> OTHER INFORMATION: Influenza A Virus

<400> SEQUENCE: 91
tcttctaacc gaggtcgaa                                           19

<210> SEQ ID NO 92
<211> LENGTH: 19
<212> TYPE: DNA
<213> ORGANISM: Artificial Sequence
<220> FEATURE:
<223> OTHER INFORMATION: Influenza A Virus

<400> SEQUENCE: 92
tcctgtcacc tctgactaa                                           19

<210> SEQ ID NO 93
<211> LENGTH: 19
<212> TYPE: DNA
<213> ORGANISM: Artificial Sequence
<220> FEATURE:
<223> OTHER INFORMATION: Influenza A Virus

<400> SEQUENCE: 93
cctgtcacct ctgactaaa                                           19

<210> SEQ ID NO 94
<211> LENGTH: 19
<212> TYPE: DNA
<213> ORGANISM: Artificial Sequence
<220> FEATURE:
<223> OTHER INFORMATION: Influenza A Virus

<400> SEQUENCE: 94
ccagttgcat gggtctcat                                           19

<210> SEQ ID NO 95
<211> LENGTH: 19
<212> TYPE: DNA
<213> ORGANISM: Artificial Sequence
<220> FEATURE:
<223> OTHER INFORMATION: Influenza A Virus

<400> SEQUENCE: 95
gcactacagc taaggctat                                           19
```

-continued

```
<210> SEQ ID NO 96
<211> LENGTH: 19
<212> TYPE: DNA
<213> ORGANISM: Artificial Sequence
<220> FEATURE:
<223> OTHER INFORMATION: Influenza A Virus

<400> SEQUENCE: 96
gcgattcaag tgatcctat                                            19

<210> SEQ ID NO 97
<211> LENGTH: 19
<212> TYPE: DNA
<213> ORGANISM: Artificial Sequence
<220> FEATURE:
<223> OTHER INFORMATION: Influenza A Virus

<400> SEQUENCE: 97
gggatcttgc acttgatat                                            19

<210> SEQ ID NO 98
<211> LENGTH: 19
<212> TYPE: DNA
<213> ORGANISM: Artificial Sequence
<220> FEATURE:
<223> OTHER INFORMATION: Influenza A Virus

<400> SEQUENCE: 98
ggatcttgca cttgatatt                                            19

<210> SEQ ID NO 99
<211> LENGTH: 19
<212> TYPE: DNA
<213> ORGANISM: Artificial Sequence
<220> FEATURE:
<223> OTHER INFORMATION: Influenza A Virus

<400> SEQUENCE: 99
gcacttgata ttgtggatt                                            19

<210> SEQ ID NO 100
<211> LENGTH: 19
<212> TYPE: DNA
<213> ORGANISM: Artificial Sequence
<220> FEATURE:
<223> OTHER INFORMATION: Influenza A Virus

<400> SEQUENCE: 100
gcatttatcg tcgccttaa                                            19

<210> SEQ ID NO 101
<211> LENGTH: 25
<212> TYPE: DNA
<213> ORGANISM: Artificial Sequence
<220> FEATURE:
<223> OTHER INFORMATION: Influenza A Virus

<400> SEQUENCE: 101
accatcggat caatctgtat ggtaa                                     25

<210> SEQ ID NO 102
<211> LENGTH: 25
<212> TYPE: DNA
<213> ORGANISM: Artificial Sequence
<220> FEATURE:
<223> OTHER INFORMATION: Influenza A Virus

<400> SEQUENCE: 102
```

```
gctgaaccaa tcagcaatac taatt                                              25

<210> SEQ ID NO 103
<211> LENGTH: 25
<212> TYPE: DNA
<213> ORGANISM: Artificial Sequence
<220> FEATURE:
<223> OTHER INFORMATION: Influenza A Virus

<400> SEQUENCE: 103
tccaatggga ctgtcaaaga cagaa                                              25

<210> SEQ ID NO 104
<211> LENGTH: 25
<212> TYPE: DNA
<213> ORGANISM: Artificial Sequence
<220> FEATURE:
<223> OTHER INFORMATION: Influenza A Virus

<400> SEQUENCE: 104
ggctgtattg aaatacaatg gcata                                              25

<210> SEQ ID NO 105
<211> LENGTH: 25
<212> TYPE: DNA
<213> ORGANISM: Artificial Sequence
<220> FEATURE:
<223> OTHER INFORMATION: Influenza A Virus

<400> SEQUENCE: 105
gcatgtgtaa atggctcttg cttta                                              25

<210> SEQ ID NO 106
<211> LENGTH: 25
<212> TYPE: DNA
<213> ORGANISM: Artificial Sequence
<220> FEATURE:
<223> OTHER INFORMATION: Influenza A Virus

<400> SEQUENCE: 106
gggaaagtgg ttaaatcagt cgaat                                              25

<210> SEQ ID NO 107
<211> LENGTH: 25
<212> TYPE: DNA
<213> ORGANISM: Artificial Sequence
<220> FEATURE:
<223> OTHER INFORMATION: Influenza A Virus

<400> SEQUENCE: 107
ggaaagtggt taaatcagtc gaatt                                              25

<210> SEQ ID NO 108
<211> LENGTH: 25
<212> TYPE: DNA
<213> ORGANISM: Artificial Sequence
<220> FEATURE:
<223> OTHER INFORMATION: Influenza A Virus

<400> SEQUENCE: 108
gctcctaatt atcactatga ggaat                                              25

<210> SEQ ID NO 109
<211> LENGTH: 25
<212> TYPE: DNA
<213> ORGANISM: Artificial Sequence
```

```
<220> FEATURE:
<223> OTHER INFORMATION: Influenza A Virus

<400> SEQUENCE: 109
gcagggataa ttggcatggc tcaaa                                         25

<210> SEQ ID NO 110
<211> LENGTH: 25
<212> TYPE: DNA
<213> ORGANISM: Artificial Sequence
<220> FEATURE:
<223> OTHER INFORMATION: Influenza A Virus

<400> SEQUENCE: 110
ccagcatcca gaactgacag gacta                                         25

<210> SEQ ID NO 111
<211> LENGTH: 19
<212> TYPE: DNA
<213> ORGANISM: Artificial Sequence
<220> FEATURE:
<223> OTHER INFORMATION: Influenza A Virus

<400> SEQUENCE: 111
ccatcggatc aatctgtat                                                19

<210> SEQ ID NO 112
<211> LENGTH: 19
<212> TYPE: DNA
<213> ORGANISM: Artificial Sequence
<220> FEATURE:
<223> OTHER INFORMATION: Influenza A Virus

<400> SEQUENCE: 112
ggatcaatct gtatggtaa                                                19

<210> SEQ ID NO 113
<211> LENGTH: 19
<212> TYPE: DNA
<213> ORGANISM: Artificial Sequence
<220> FEATURE:
<223> OTHER INFORMATION: Influenza A Virus

<400> SEQUENCE: 113
gctgaaccaa tcagcaata                                                19

<210> SEQ ID NO 114
<211> LENGTH: 19
<212> TYPE: DNA
<213> ORGANISM: Artificial Sequence
<220> FEATURE:
<223> OTHER INFORMATION: Influenza A Virus

<400> SEQUENCE: 114
gggactgtca aagacagaa                                                19

<210> SEQ ID NO 115
<211> LENGTH: 19
<212> TYPE: DNA
<213> ORGANISM: Artificial Sequence
<220> FEATURE:
<223> OTHER INFORMATION: Influenza A Virus

<400> SEQUENCE: 115
gcttggtcag caagtgctt                                                19
```

```
<210> SEQ ID NO 116
<211> LENGTH: 19
<212> TYPE: DNA
<213> ORGANISM: Artificial Sequence
<220> FEATURE:
<223> OTHER INFORMATION: Influenza A Virus

<400> SEQUENCE: 116
gcaccagttg gttgacaat                                              19

<210> SEQ ID NO 117
<211> LENGTH: 19
<212> TYPE: DNA
<213> ORGANISM: Artificial Sequence
<220> FEATURE:
<223> OTHER INFORMATION: Influenza A Virus

<400> SEQUENCE: 117
gctgtggctg tattgaaat                                              19

<210> SEQ ID NO 118
<211> LENGTH: 19
<212> TYPE: DNA
<213> ORGANISM: Artificial Sequence
<220> FEATURE:
<223> OTHER INFORMATION: Influenza A Virus

<400> SEQUENCE: 118
gcatgtgtaa atggctctt                                              19

<210> SEQ ID NO 119
<211> LENGTH: 19
<212> TYPE: DNA
<213> ORGANISM: Artificial Sequence
<220> FEATURE:
<223> OTHER INFORMATION: Influenza A Virus

<400> SEQUENCE: 119
gctcttgctt tactgtaat                                              19

<210> SEQ ID NO 120
<211> LENGTH: 19
<212> TYPE: DNA
<213> ORGANISM: Artificial Sequence
<220> FEATURE:
<223> OTHER INFORMATION: Influenza A Virus

<400> SEQUENCE: 120
ccaggagcgg ctttgaaat                                              19

<210> SEQ ID NO 121
<211> LENGTH: 25
<212> TYPE: DNA
<213> ORGANISM: Artificial Sequence
<220> FEATURE:
<223> OTHER INFORMATION: Influenza A Virus

<400> SEQUENCE: 121
gcgtctcaag gcaccaaacg atctt                                       25

<210> SEQ ID NO 122
<211> LENGTH: 25
<212> TYPE: DNA
<213> ORGANISM: Artificial Sequence
<220> FEATURE:
<223> OTHER INFORMATION: Influenza A Virus

<400> SEQUENCE: 122
```
gcacagaact caaactcagt gacta                                          25

<210> SEQ ID NO 123
<211> LENGTH: 25
<212> TYPE: DNA
<213> ORGANISM: Artificial Sequence
<220> FEATURE:
<223> OTHER INFORMATION: Influenza A Virus

<400> SEQUENCE: 123
gctggtctta cccacctgat gatat                                          25

<210> SEQ ID NO 124
<211> LENGTH: 25
<212> TYPE: DNA
<213> ORGANISM: Artificial Sequence
<220> FEATURE:
<223> OTHER INFORMATION: Influenza A Virus

<400> SEQUENCE: 124
ggtgatggag ctgattcgga tgata                                          25

<210> SEQ ID NO 125
<211> LENGTH: 25
<212> TYPE: DNA
<213> ORGANISM: Artificial Sequence
<220> FEATURE:
<223> OTHER INFORMATION: Influenza A Virus

<400> SEQUENCE: 125
tcctgagagg atcagtggcc cataa                                          25

<210> SEQ ID NO 126
<211> LENGTH: 25
<212> TYPE: DNA
<213> ORGANISM: Artificial Sequence
<220> FEATURE:
<223> OTHER INFORMATION: Influenza A Virus

<400> SEQUENCE: 126
gcagtggcca gtggatatga ctttg                                          25

<210> SEQ ID NO 127
<211> LENGTH: 25
<212> TYPE: DNA
<213> ORGANISM: Artificial Sequence
<220> FEATURE:
<223> OTHER INFORMATION: Influenza A Virus

<400> SEQUENCE: 127
gccagtggat atgactttga gagag                                          25

<210> SEQ ID NO 128
<211> LENGTH: 25
<212> TYPE: DNA
<213> ORGANISM: Artificial Sequence
<220> FEATURE:
<223> OTHER INFORMATION: Influenza A Virus

<400> SEQUENCE: 128
ggtctttagt ctcattagac caaat                                          25

<210> SEQ ID NO 129
<211> LENGTH: 25
<212> TYPE: DNA
<213> ORGANISM: Artificial Sequence

```
<220> FEATURE:
<223> OTHER INFORMATION: Influenza A Virus

<400> SEQUENCE: 129
ggaggcaatg gactccaaca ctctt                                          25

<210> SEQ ID NO 130
<211> LENGTH: 25
<212> TYPE: DNA
<213> ORGANISM: Artificial Sequence
<220> FEATURE:
<223> OTHER INFORMATION: Influenza A Virus

<400> SEQUENCE: 130
ccattatggc agcatttaca ggaaa                                          25

<210> SEQ ID NO 131
<211> LENGTH: 19
<212> TYPE: DNA
<213> ORGANISM: Artificial Sequence
<220> FEATURE:
<223> OTHER INFORMATION: Influenza A Virus

<400> SEQUENCE: 131
gccagaatgc tactgagat                                                 19

<210> SEQ ID NO 132
<211> LENGTH: 19
<212> TYPE: DNA
<213> ORGANISM: Artificial Sequence
<220> FEATURE:
<223> OTHER INFORMATION: Influenza A Virus

<400> SEQUENCE: 132
gctaattctg tacgacaaa                                                 19

<210> SEQ ID NO 133
<211> LENGTH: 19
<212> TYPE: DNA
<213> ORGANISM: Artificial Sequence
<220> FEATURE:
<223> OTHER INFORMATION: Influenza A Virus

<400> SEQUENCE: 133
ggatttggcg tcaagcgaa                                                 19

<210> SEQ ID NO 134
<211> LENGTH: 19
<212> TYPE: DNA
<213> ORGANISM: Artificial Sequence
<220> FEATURE:
<223> OTHER INFORMATION: Influenza A Virus

<400> SEQUENCE: 134
gccaggtctt tagtctcat                                                 19

<210> SEQ ID NO 135
<211> LENGTH: 19
<212> TYPE: DNA
<213> ORGANISM: Artificial Sequence
<220> FEATURE:
<223> OTHER INFORMATION: Influenza A Virus

<400> SEQUENCE: 135
ccagcacata agagtcaat                                                 19
```

```
<210> SEQ ID NO 136
<211> LENGTH: 19
<212> TYPE: DNA
<213> ORGANISM: Artificial Sequence
<220> FEATURE:
<223> OTHER INFORMATION: Influenza A Virus

<400> SEQUENCE: 136
gcagcatttg aggacctta                                              19

<210> SEQ ID NO 137
<211> LENGTH: 19
<212> TYPE: DNA
<213> ORGANISM: Artificial Sequence
<220> FEATURE:
<223> OTHER INFORMATION: Influenza A Virus

<400> SEQUENCE: 137
ggactccaac actcttgaa                                              19

<210> SEQ ID NO 138
<211> LENGTH: 19
<212> TYPE: DNA
<213> ORGANISM: Artificial Sequence
<220> FEATURE:
<223> OTHER INFORMATION: Influenza A Virus

<400> SEQUENCE: 138
gcgaccatta tggcagcat                                              19

<210> SEQ ID NO 139
<211> LENGTH: 19
<212> TYPE: DNA
<213> ORGANISM: Artificial Sequence
<220> FEATURE:
<223> OTHER INFORMATION: Influenza A Virus

<400> SEQUENCE: 139
gcagcattta caggaaata                                              19

<210> SEQ ID NO 140
<211> LENGTH: 19
<212> TYPE: DNA
<213> ORGANISM: Artificial Sequence
<220> FEATURE:
<223> OTHER INFORMATION: Influenza A Virus

<400> SEQUENCE: 140
ggaaatactg agggcagaa                                              19

<210> SEQ ID NO 141
<211> LENGTH: 25
<212> TYPE: DNA
<213> ORGANISM: Artificial Sequence
<220> FEATURE:
<223> OTHER INFORMATION: Influenza A Virus

<400> SEQUENCE: 141
tctttggcat gtccgcaaac gattt                                       25

<210> SEQ ID NO 142
<211> LENGTH: 25
<212> TYPE: DNA
<213> ORGANISM: Artificial Sequence
<220> FEATURE:
<223> OTHER INFORMATION: Influenza A Virus

<400> SEQUENCE: 142
```
gacatgactc tcgaagaaat gtcaa          25

<210> SEQ ID NO 143
<211> LENGTH: 25
<212> TYPE: DNA
<213> ORGANISM: Artificial Sequence
<220> FEATURE:
<223> OTHER INFORMATION: Influenza A Virus

<400> SEQUENCE: 143
ccattacctt ctcttccagg acata          25

<210> SEQ ID NO 144
<211> LENGTH: 25
<212> TYPE: DNA
<213> ORGANISM: Artificial Sequence
<220> FEATURE:
<223> OTHER INFORMATION: Influenza A Virus

<400> SEQUENCE: 144
tcctcatcgg aggacttgaa tggaa          25

<210> SEQ ID NO 145
<211> LENGTH: 25
<212> TYPE: DNA
<213> ORGANISM: Artificial Sequence
<220> FEATURE:
<223> OTHER INFORMATION: Influenza A Virus

<400> SEQUENCE: 145
cctcatcgga ggacttgaat ggaat          25

<210> SEQ ID NO 146
<211> LENGTH: 25
<212> TYPE: DNA
<213> ORGANISM: Artificial Sequence
<220> FEATURE:
<223> OTHER INFORMATION: Influenza A Virus

<400> SEQUENCE: 146
tcggaggact tgaatggaat gataa          25

<210> SEQ ID NO 147
<211> LENGTH: 25
<212> TYPE: DNA
<213> ORGANISM: Artificial Sequence
<220> FEATURE:
<223> OTHER INFORMATION: Influenza A Virus

<400> SEQUENCE: 147
gagtcactga aactatacag agatt          25

<210> SEQ ID NO 148
<211> LENGTH: 25
<212> TYPE: DNA
<213> ORGANISM: Artificial Sequence
<220> FEATURE:
<223> OTHER INFORMATION: Influenza A Virus

<400> SEQUENCE: 148
gcaagagata agagccttct cgttt          25

<210> SEQ ID NO 149
<211> LENGTH: 25
<212> TYPE: DNA
<213> ORGANISM: Artificial Sequence -continued
<220> FEATURE:
<223> OTHER INFORMATION: Influenza A Virus

<400> SEQUENCE: 149
gagccttctc gtttcagctt attta 25

<210> SEQ ID NO 150
<211> LENGTH: 25
<212> TYPE: DNA
<213> ORGANISM: Artificial Sequence
<220> FEATURE:
<223> OTHER INFORMATION: Influenza A Virus

<400> SEQUENCE: 150
gccttctcgt ttcagcttat ttaat 25

<210> SEQ ID NO 151
<211> LENGTH: 19
<212> TYPE: DNA
<213> ORGANISM: Artificial Sequence
<220> FEATURE:
<223> OTHER INFORMATION: Influenza A Virus

<400> SEQUENCE: 151
ccaacactgt gtcaagctt 19

<210> SEQ ID NO 152
<211> LENGTH: 19
<212> TYPE: DNA
<213> ORGANISM: Artificial Sequence
<220> FEATURE:
<223> OTHER INFORMATION: Influenza A Virus

<400> SEQUENCE: 152
gctttcaggt agactgctt 19

<210> SEQ ID NO 153
<211> LENGTH: 19
<212> TYPE: DNA
<213> ORGANISM: Artificial Sequence
<220> FEATURE:
<223> OTHER INFORMATION: Influenza A Virus

<400> SEQUENCE: 153
gcatgtccgc aaacgattt 19

<210> SEQ ID NO 154
<211> LENGTH: 19
<212> TYPE: DNA
<213> ORGANISM: Artificial Sequence
<220> FEATURE:
<223> OTHER INFORMATION: Influenza A Virus

<400> SEQUENCE: 154
ccctaagagg aagaggcaa 19

<210> SEQ ID NO 155
<211> LENGTH: 19
<212> TYPE: DNA
<213> ORGANISM: Artificial Sequence
<220> FEATURE:
<223> OTHER INFORMATION: Influenza A Virus

<400> SEQUENCE: 155
ggagtctgat aaggcactt 19

<210> SEQ ID NO 156
<211> LENGTH: 19
<212> TYPE: DNA
<213> ORGANISM: Artificial Sequence
<220> FEATURE:
<223> OTHER INFORMATION: Influenza A Virus

<400> SEQUENCE: 156
gggactggtt catgctcat                                              19

<210> SEQ ID NO 157
<211> LENGTH: 19
<212> TYPE: DNA
<213> ORGANISM: Artificial Sequence
<220> FEATURE:
<223> OTHER INFORMATION: Influenza A Virus

<400> SEQUENCE: 157
ggttcatgct catgcccaa                                              19

<210> SEQ ID NO 158
<211> LENGTH: 19
<212> TYPE: DNA
<213> ORGANISM: Artificial Sequence
<220> FEATURE:
<223> OTHER INFORMATION: Influenza A Virus

<400> SEQUENCE: 158
gctcatgccc aagcagaaa                                              19

<210> SEQ ID NO 159
<211> LENGTH: 19
<212> TYPE: DNA
<213> ORGANISM: Artificial Sequence
<220> FEATURE:
<223> OTHER INFORMATION: Influenza A Virus

<400> SEQUENCE: 159
gccttctcgt ttcagctta                                              19

<210> SEQ ID NO 160
<211> LENGTH: 19
<212> TYPE: DNA
<213> ORGANISM: Artificial Sequence
<220> FEATURE:
<223> OTHER INFORMATION: Influenza A Virus

<400> SEQUENCE: 160
ccttctcgtt tcagcttat                                              19

<210> SEQ ID NO 161
<211> LENGTH: 25
<212> TYPE: DNA
<213> ORGANISM: Artificial Sequence
<220> FEATURE:
<223> OTHER INFORMATION: Influenza A Virus

<400> SEQUENCE: 161
ccaatgatcg tcgagcttgc ggaaa                                       25

<210> SEQ ID NO 162
<211> LENGTH: 25
<212> TYPE: DNA
<213> ORGANISM: Artificial Sequence
<220> FEATURE:
<223> OTHER INFORMATION: Influenza A Virus

<400> SEQUENCE: 162
ggaggtctgt ttcatgtatt cggat          25

<210> SEQ ID NO 163
<211> LENGTH: 25
<212> TYPE: DNA
<213> ORGANISM: Artificial Sequence
<220> FEATURE:
<223> OTHER INFORMATION: Influenza A Virus

<400> SEQUENCE: 163
ggactgtggt gaatagtatc tgcaa          25

<210> SEQ ID NO 164
<211> LENGTH: 25
<212> TYPE: DNA
<213> ORGANISM: Artificial Sequence
<220> FEATURE:
<223> OTHER INFORMATION: Influenza A Virus

<400> SEQUENCE: 164
gggtctatgg gattcctttc gtcaa 25

<210> SEQ ID NO 165
<211> LENGTH: 25
<212> TYPE: DNA
<213> ORGANISM: Artificial Sequence
<220> FEATURE:
<223> OTHER INFORMATION: Influenza A Virus

<400> SEQUENCE: 165
ccaccgaact tctccagcct tgaaa 25

<210> SEQ ID NO 166
<211> LENGTH: 25
<212> TYPE: DNA
<213> ORGANISM: Artificial Sequence
<220> FEATURE:
<223> OTHER INFORMATION: Influenza A Virus

<400> SEQUENCE: 166
ggatgccctt aaattaagca tcgaa 25

<210> SEQ ID NO 167
<211> LENGTH: 25
<212> TYPE: DNA
<213> ORGANISM: Artificial Sequence
<220> FEATURE:
<223> OTHER INFORMATION: Influenza A Virus

<400> SEQUENCE: 167
ggataccact atacgatgca atcaa 25

<210> SEQ ID NO 168
<211> LENGTH: 25
<212> TYPE: DNA
<213> ORGANISM: Artificial Sequence
<220> FEATURE:
<223> OTHER INFORMATION: Influenza A Virus

<400> SEQUENCE: 168
cccaacatcg tgaaaccaca tgaaa 25

<210> SEQ ID NO 169
<211> LENGTH: 25
<212> TYPE: DNA
<213> ORGANISM: Artificial Sequence

```
<220> FEATURE:
<223> OTHER INFORMATION: Influenza A Virus

<400> SEQUENCE: 169
ggaatgatac cgatgtggta aattt                                              25

<210> SEQ ID NO 170
<211> LENGTH: 25
<212> TYPE: DNA
<213> ORGANISM: Artificial Sequence
<220> FEATURE:
<223> OTHER INFORMATION: Influenza A Virus

<400> SEQUENCE: 170
ggcaatgcta ctatttgcta tccat                                              25

<210> SEQ ID NO 171
<211> LENGTH: 19
<212> TYPE: DNA
<213> ORGANISM: Artificial Sequence
<220> FEATURE:
<223> OTHER INFORMATION: Influenza A Virus

<400> SEQUENCE: 171
ggaagacttt gtgcgacaa                                                     19

<210> SEQ ID NO 172
<211> LENGTH: 19
<212> TYPE: DNA
<213> ORGANISM: Artificial Sequence
<220> FEATURE:
<223> OTHER INFORMATION: Influenza A Virus

<400> SEQUENCE: 172
cctaaatttc tcccagatt                                                     19

<210> SEQ ID NO 173
<211> LENGTH: 19
<212> TYPE: DNA
<213> ORGANISM: Artificial Sequence
<220> FEATURE:
<223> OTHER INFORMATION: Influenza A Virus

<400> SEQUENCE: 173
ggactacacc cttgatgaa                                                     19

<210> SEQ ID NO 174
<211> LENGTH: 19
<212> TYPE: DNA
<213> ORGANISM: Artificial Sequence
<220> FEATURE:
<223> OTHER INFORMATION: Influenza A Virus

<400> SEQUENCE: 174
gctgatggat gcccttaaa                                                     19

<210> SEQ ID NO 175
<211> LENGTH: 19
<212> TYPE: DNA
<213> ORGANISM: Artificial Sequence
<220> FEATURE:
<223> OTHER INFORMATION: Influenza A Virus

<400> SEQUENCE: 175
ggaattctct cttactgat                                                     19
```

```
<210> SEQ ID NO 176
<211> LENGTH: 19
<212> TYPE: DNA
<213> ORGANISM: Artificial Sequence
<220> FEATURE:
<223> OTHER INFORMATION: Influenza A Virus

<400> SEQUENCE: 176
gcagtaggcc aagtttcaa                                             19

<210> SEQ ID NO 177
<211> LENGTH: 19
<212> TYPE: DNA
<213> ORGANISM: Artificial Sequence
<220> FEATURE:
<223> OTHER INFORMATION: Influenza A Virus

<400> SEQUENCE: 177
gcccatgttc ctgtatgta                                             19

<210> SEQ ID NO 178
<211> LENGTH: 19
<212> TYPE: DNA
<213> ORGANISM: Artificial Sequence
<220> FEATURE:
<223> OTHER INFORMATION: Influenza A Virus

<400> SEQUENCE: 178
ggaaatgagg cgatgcctt                                             19

<210> SEQ ID NO 179
<211> LENGTH: 19
<212> TYPE: DNA
<213> ORGANISM: Artificial Sequence
<220> FEATURE:
<223> OTHER INFORMATION: Influenza A Virus

<400> SEQUENCE: 179
cctcgcacat gcactgaaa                                             19

<210> SEQ ID NO 180
<211> LENGTH: 19
<212> TYPE: DNA
<213> ORGANISM: Artificial Sequence
<220> FEATURE:
<223> OTHER INFORMATION: Influenza A Virus

<400> SEQUENCE: 180
gcaatgctac tatttgcta                                             19

<210> SEQ ID NO 181
<211> LENGTH: 25
<212> TYPE: DNA
<213> ORGANISM: Artificial Sequence
<220> FEATURE:
<223> OTHER INFORMATION: Influenza A Virus

<400> SEQUENCE: 181
ggcaaaccat ttgaatggat gtcaa                                      25

<210> SEQ ID NO 182
<211> LENGTH: 25
<212> TYPE: DNA
<213> ORGANISM: Artificial Sequence
<220> FEATURE:
<223> OTHER INFORMATION: Influenza A Virus

<400> SEQUENCE: 182
```
gctataagta ccacattccc ttata                                              25

<210> SEQ ID NO 183
<211> LENGTH: 25
<212> TYPE: DNA
<213> ORGANISM: Artificial Sequence
<220> FEATURE:
<223> OTHER INFORMATION: Influenza A Virus

<400> SEQUENCE: 183
cctatgactg gacattgaat agaaa                                              25

<210> SEQ ID NO 184
<211> LENGTH: 25
<212> TYPE: DNA
<213> ORGANISM: Artificial Sequence
<220> FEATURE:
<223> OTHER INFORMATION: Influenza A Virus

<400> SEQUENCE: 184
gccagaatgg tttcggaatg tctta                                              25

<210> SEQ ID NO 185
<211> LENGTH: 25
<212> TYPE: DNA
<213> ORGANISM: Artificial Sequence
<220> FEATURE:
<223> OTHER INFORMATION: Influenza A Virus

<400> SEQUENCE: 185
ggaatgtctt aagcattgca cctat                                              25

<210> SEQ ID NO 186
<211> LENGTH: 25
<212> TYPE: DNA
<213> ORGANISM: Artificial Sequence
<220> FEATURE:
<223> OTHER INFORMATION: Influenza A Virus

<400> SEQUENCE: 186
ggacggactc caatcctctg atgat                                              25

<210> SEQ ID NO 187
<211> LENGTH: 25
<212> TYPE: DNA
<213> ORGANISM: Artificial Sequence
<220> FEATURE:
<223> OTHER INFORMATION: Influenza A Virus

<400> SEQUENCE: 187
ggacttgtaa actagttgga atcaa                                              25

<210> SEQ ID NO 188
<211> LENGTH: 25
<212> TYPE: DNA
<213> ORGANISM: Artificial Sequence
<220> FEATURE:
<223> OTHER INFORMATION: Influenza A Virus

<400> SEQUENCE: 188
ggaccaaatc tatacaatat ccgaa                                              25

<210> SEQ ID NO 189
<211> LENGTH: 25
<212> TYPE: DNA
<213> ORGANISM: Artificial Sequence

```
<220> FEATURE:
<223> OTHER INFORMATION: Influenza A Virus

<400> SEQUENCE: 189
gcaactacac attcatggat tccta                                        25

<210> SEQ ID NO 190
<211> LENGTH: 25
<212> TYPE: DNA
<213> ORGANISM: Artificial Sequence
<220> FEATURE:
<223> OTHER INFORMATION: Influenza A Virus

<400> SEQUENCE: 190
cccgaattga cgcacgaatt gattt                                        25

<210> SEQ ID NO 191
<211> LENGTH: 19
<212> TYPE: DNA
<213> ORGANISM: Artificial Sequence
<220> FEATURE:
<223> OTHER INFORMATION: Influenza A Virus

<400> SEQUENCE: 191
gcaggcaaac catttgaat                                               19

<210> SEQ ID NO 192
<211> LENGTH: 19
<212> TYPE: DNA
<213> ORGANISM: Artificial Sequence
<220> FEATURE:
<223> OTHER INFORMATION: Influenza A Virus

<400> SEQUENCE: 192
ccatttgaat ggatgtcaa                                               19

<210> SEQ ID NO 193
<211> LENGTH: 19
<212> TYPE: DNA
<213> ORGANISM: Artificial Sequence
<220> FEATURE:
<223> OTHER INFORMATION: Influenza A Virus

<400> SEQUENCE: 193
gcacaaacag attgtgtat                                               19

<210> SEQ ID NO 194
<211> LENGTH: 19
<212> TYPE: DNA
<213> ORGANISM: Artificial Sequence
<220> FEATURE:
<223> OTHER INFORMATION: Influenza A Virus

<400> SEQUENCE: 194
gcactgacac tgaacacaa                                               19

<210> SEQ ID NO 195
<211> LENGTH: 19
<212> TYPE: DNA
<213> ORGANISM: Artificial Sequence
<220> FEATURE:
<223> OTHER INFORMATION: Influenza A Virus

<400> SEQUENCE: 195
gcaacacccg gaatgcaaa                                               19
```

```
<210> SEQ ID NO 196
<211> LENGTH: 19
<212> TYPE: DNA
<213> ORGANISM: Artificial Sequence
<220> FEATURE:
<223> OTHER INFORMATION: Influenza A Virus

<400> SEQUENCE: 196
ggatgtttct ggcaatgat                                              19

<210> SEQ ID NO 197
<211> LENGTH: 19
<212> TYPE: DNA
<213> ORGANISM: Artificial Sequence
<220> FEATURE:
<223> OTHER INFORMATION: Influenza A Virus

<400> SEQUENCE: 197
ggaaccagcc agaatggtt                                              19

<210> SEQ ID NO 198
<211> LENGTH: 19
<212> TYPE: DNA
<213> ORGANISM: Artificial Sequence
<220> FEATURE:
<223> OTHER INFORMATION: Influenza A Virus

<400> SEQUENCE: 198
gcacctataa tgttctcaa                                              19

<210> SEQ ID NO 199
<211> LENGTH: 19
<212> TYPE: DNA
<213> ORGANISM: Artificial Sequence
<220> FEATURE:
<223> OTHER INFORMATION: Influenza A Virus

<400> SEQUENCE: 199
gcttgcaaac attgatctt                                              19

<210> SEQ ID NO 200
<211> LENGTH: 19
<212> TYPE: DNA
<213> ORGANISM: Artificial Sequence
<220> FEATURE:
<223> OTHER INFORMATION: Influenza A Virus

<400> SEQUENCE: 200
ggagatcatt cgagctgaa                                              19

<210> SEQ ID NO 201
<211> LENGTH: 25
<212> TYPE: DNA
<213> ORGANISM: Artificial Sequence
<220> FEATURE:
<223> OTHER INFORMATION: Influenza A Virus

<400> SEQUENCE: 201
cccgcactcg cgagatacta acaaa                                       25

<210> SEQ ID NO 202
<211> LENGTH: 25
<212> TYPE: DNA
<213> ORGANISM: Artificial Sequence
<220> FEATURE:
<223> OTHER INFORMATION: Influenza A Virus

<400> SEQUENCE: 202
```
ccaatcacag cggacaagag aataa                                    25

<210> SEQ ID NO 203
<211> LENGTH: 25
<212> TYPE: DNA
<213> ORGANISM: Artificial Sequence
<220> FEATURE:
<223> OTHER INFORMATION: Influenza A Virus

<400> SEQUENCE: 203
ggagatgtgt cacagcacac aaatt                                    25

<210> SEQ ID NO 204
<211> LENGTH: 25
<212> TYPE: DNA
<213> ORGANISM: Artificial Sequence
<220> FEATURE:
<223> OTHER INFORMATION: Influenza A Virus

<400> SEQUENCE: 204
ggaacaagct gtggatatat gcaaa                                    25

<210> SEQ ID NO 205
<211> LENGTH: 25
<212> TYPE: DNA
<213> ORGANISM: Artificial Sequence
<220> FEATURE:
<223> OTHER INFORMATION: Influenza A Virus

<400> SEQUENCE: 205
cccatgcatc aactcctgag acatt                                    25

<210> SEQ ID NO 206
<211> LENGTH: 25
<212> TYPE: DNA
<213> ORGANISM: Artificial Sequence
<220> FEATURE:
<223> OTHER INFORMATION: Influenza A Virus

<400> SEQUENCE: 206
ggatgatcgg aatattacct gacat                                    25

<210> SEQ ID NO 207
<211> LENGTH: 25
<212> TYPE: DNA
<213> ORGANISM: Artificial Sequence
<220> FEATURE:
<223> OTHER INFORMATION: Influenza A Virus

<400> SEQUENCE: 207
cctgacatga ctcccagcac agaaa                                    25

<210> SEQ ID NO 208
<211> LENGTH: 25
<212> TYPE: DNA
<213> ORGANISM: Artificial Sequence
<220> FEATURE:
<223> OTHER INFORMATION: Influenza A Virus

<400> SEQUENCE: 208
gggacatttg atactgtcca gataa                                    25

<210> SEQ ID NO 209
<211> LENGTH: 25
<212> TYPE: DNA
<213> ORGANISM: Artificial Sequence

```
<220> FEATURE:
<223> OTHER INFORMATION: Influenza A Virus

<400> SEQUENCE: 209
ccagataata aagctgctac cattt                                              25

<210> SEQ ID NO 210
<211> LENGTH: 25
<212> TYPE: DNA
<213> ORGANISM: Artificial Sequence
<220> FEATURE:
<223> OTHER INFORMATION: Influenza A Virus

<400> SEQUENCE: 210
ggtatggacc agcattgagc atcaa                                              25

<210> SEQ ID NO 211
<211> LENGTH: 19
<212> TYPE: DNA
<213> ORGANISM: Artificial Sequence
<220> FEATURE:
<223> OTHER INFORMATION: Influenza A Virus

<400> SEQUENCE: 211
gctgtaactt ggtggaata                                                     19

<210> SEQ ID NO 212
<211> LENGTH: 19
<212> TYPE: DNA
<213> ORGANISM: Artificial Sequence
<220> FEATURE:
<223> OTHER INFORMATION: Influenza A Virus

<400> SEQUENCE: 212
cctttggtcc cgttcattt                                                     19

<210> SEQ ID NO 213
<211> LENGTH: 19
<212> TYPE: DNA
<213> ORGANISM: Artificial Sequence
<220> FEATURE:
<223> OTHER INFORMATION: Influenza A Virus

<400> SEQUENCE: 213
gctccaagat tgtaagatt                                                     19

<210> SEQ ID NO 214
<211> LENGTH: 19
<212> TYPE: DNA
<213> ORGANISM: Artificial Sequence
<220> FEATURE:
<223> OTHER INFORMATION: Influenza A Virus

<400> SEQUENCE: 214
ggtattgcat ttgactcaa                                                     19

<210> SEQ ID NO 215
<211> LENGTH: 19
<212> TYPE: DNA
<213> ORGANISM: Artificial Sequence
<220> FEATURE:
<223> OTHER INFORMATION: Influenza A Virus

<400> SEQUENCE: 215
gctgccagaa acattgtta                                                     19
```

```
<210> SEQ ID NO 216
<211> LENGTH: 19
<212> TYPE: DNA
<213> ORGANISM: Artificial Sequence
<220> FEATURE:
<223> OTHER INFORMATION: Influenza A Virus

<400> SEQUENCE: 216
ggataaggat ggtggacat                                               19

<210> SEQ ID NO 217
<211> LENGTH: 19
<212> TYPE: DNA
<213> ORGANISM: Artificial Sequence
<220> FEATURE:
<223> OTHER INFORMATION: Influenza A Virus

<400> SEQUENCE: 217
ggaagagacg aacaatcaa                                               19

<210> SEQ ID NO 218
<211> LENGTH: 19
<212> TYPE: DNA
<213> ORGANISM: Artificial Sequence
<220> FEATURE:
<223> OTHER INFORMATION: Influenza A Virus

<400> SEQUENCE: 218
gcatcaactc ctgagacat                                               19

<210> SEQ ID NO 219
<211> LENGTH: 19
<212> TYPE: DNA
<213> ORGANISM: Artificial Sequence
<220> FEATURE:
<223> OTHER INFORMATION: Influenza A Virus

<400> SEQUENCE: 219
gcatcaatga actgagcaa                                               19

<210> SEQ ID NO 220
<211> LENGTH: 19
<212> TYPE: DNA
<213> ORGANISM: Artificial Sequence
<220> FEATURE:
<223> OTHER INFORMATION: Influenza A Virus

<400> SEQUENCE: 220
gccatcaatt agtgtcgaa                                               19

<210> SEQ ID NO 221
<211> LENGTH: 21
<212> TYPE: DNA
<213> ORGANISM: Artificial Sequence
<220> FEATURE:
<223> OTHER INFORMATION: Influenza A Virus

<400> SEQUENCE: 221
aatggtagat ggttggtatg g                                            21

<210> SEQ ID NO 222
<211> LENGTH: 21
<212> TYPE: DNA
<213> ORGANISM: Artificial Sequence
<220> FEATURE:
<223> OTHER INFORMATION: Influenza A Virus

<400> SEQUENCE: 222
```

-continued aaggcaatag atggagtcac c                                              21

<210> SEQ ID NO 223
<211> LENGTH: 21
<212> TYPE: DNA
<213> ORGANISM: Artificial Sequence
<220> FEATURE:
<223> OTHER INFORMATION: Influenza A Virus

<400> SEQUENCE: 223
aacactcagt ttgaggccgt t                                              21

<210> SEQ ID NO 224
<211> LENGTH: 21
<212> TYPE: DNA
<213> ORGANISM: Artificial Sequence
<220> FEATURE:
<223> OTHER INFORMATION: Influenza A Virus

<400> SEQUENCE: 224
aagatggaag acggattcct a                                              21

<210> SEQ ID NO 225
<211> LENGTH: 21
<212> TYPE: DNA
<213> ORGANISM: Artificial Sequence
<220> FEATURE:
<223> OTHER INFORMATION: Influenza A Virus

<400> SEQUENCE: 225
aatgctgaac ttctggttct c                                              21

<210> SEQ ID NO 226
<211> LENGTH: 21
<212> TYPE: DNA
<213> ORGANISM: Artificial Sequence
<220> FEATURE:
<223> OTHER INFORMATION: Influenza A Virus

<400> SEQUENCE: 226
aactctagac tttcatgact c                                              21

<210> SEQ ID NO 227
<211> LENGTH: 21
<212> TYPE: DNA
<213> ORGANISM: Artificial Sequence
<220> FEATURE:
<223> OTHER INFORMATION: Influenza A Virus

<400> SEQUENCE: 227
aaggtccgac tacagcttag g                                              21

<210> SEQ ID NO 228
<211> LENGTH: 21
<212> TYPE: DNA
<213> ORGANISM: Artificial Sequence
<220> FEATURE:
<223> OTHER INFORMATION: Influenza A Virus

<400> SEQUENCE: 228
aatgtgataa tgaatgtatg g                                              21

<210> SEQ ID NO 229
<211> LENGTH: 21
<212> TYPE: DNA
<213> ORGANISM: Artificial Sequence
<220> FEATURE:
<223> OTHER INFORMATION: Influenza A Virus

<400> SEQUENCE: 229
aacagtggcg agttccctag c 21

<210> SEQ ID NO 230
<211> LENGTH: 21
<212> TYPE: DNA
<213> ORGANISM: Artificial Sequence
<220> FEATURE:
<223> OTHER INFORMATION: Influenza A Virus

<400> SEQUENCE: 230
aatctgtatg gtaattggaa t 21

<210> SEQ ID NO 231
<211> LENGTH: 21
<212> TYPE: DNA
<213> ORGANISM: Artificial Sequence
<220> FEATURE:
<223> OTHER INFORMATION: Influenza A Virus

<400> SEQUENCE: 231
aacattagcg ggcaattcat c 21

<210> SEQ ID NO 232
<211> LENGTH: 21
<212> TYPE: DNA
<213> ORGANISM: Artificial Sequence
<220> FEATURE:
<223> OTHER INFORMATION: Influenza A Virus

<400> SEQUENCE: 232
aaagacagaa gccctcacag a 21

<210> SEQ ID NO 233
<211> LENGTH: 21
<212> TYPE: DNA
<213> ORGANISM: Artificial Sequence
<220> FEATURE:
<223> OTHER INFORMATION: Influenza A Virus

<400> SEQUENCE: 233
aattggaatt tctggcccag a 21

<210> SEQ ID NO 234
<211> LENGTH: 21
<212> TYPE: DNA
<213> ORGANISM: Artificial Sequence
<220> FEATURE:
<223> OTHER INFORMATION: Influenza A Virus

<400> SEQUENCE: 234
aatggggctg tggctgtatt g 21

<210> SEQ ID NO 235
<211> LENGTH: 21
<212> TYPE: DNA
<213> ORGANISM: Artificial Sequence
<220> FEATURE:
<223> OTHER INFORMATION: Influenza A Virus

<400> SEQUENCE: 235
aacagacact atcaagagtt g 21

-continued

<210> SEQ ID NO 236
<211> LENGTH: 21
<212> TYPE: DNA
<213> ORGANISM: Artificial Sequence
<220> FEATURE:
<223> OTHER INFORMATION: Influenza A Virus

<400> SEQUENCE: 236
aacatactga gaactcaaga g                                              21

<210> SEQ ID NO 237
<211> LENGTH: 21
<212> TYPE: DNA
<213> ORGANISM: Artificial Sequence
<220> FEATURE:
<223> OTHER INFORMATION: Influenza A Virus

<400> SEQUENCE: 237
aatgtgcatg tgtaaatggc t                                              21

<210> SEQ ID NO 238
<211> LENGTH: 21
<212> TYPE: DNA
<213> ORGANISM: Artificial Sequence
<220> FEATURE:
<223> OTHER INFORMATION: Influenza A Virus

<400> SEQUENCE: 238
aattatcact atgaggagtg c                                              21

<210> SEQ ID NO 239
<211> LENGTH: 21
<212> TYPE: DNA
<213> ORGANISM: Artificial Sequence
<220> FEATURE:
<223> OTHER INFORMATION: Influenza A Virus

<400> SEQUENCE: 239
aatcacatgt gtgtgcaggg a                                              21

<210> SEQ ID NO 240
<211> LENGTH: 21
<212> TYPE: DNA
<213> ORGANISM: Artificial Sequence
<220> FEATURE:
<223> OTHER INFORMATION: Influenza A Virus

<400> SEQUENCE: 240
aagggttttc atttaaatac g                                              21

<210> SEQ ID NO 241
<211> LENGTH: 21
<212> TYPE: DNA
<213> ORGANISM: Artificial Sequence
<220> FEATURE:
<223> OTHER INFORMATION: Influenza A Virus

<400> SEQUENCE: 241
aatgggtgga ctggaacgga c                                              21

<210> SEQ ID NO 242
<211> LENGTH: 21
<212> TYPE: DNA
<213> ORGANISM: Artificial Sequence
<220> FEATURE:
<223> OTHER INFORMATION: Influenza A Virus

<400> SEQUENCE: 242
aactgattgg tcaggatata g                                21

<210> SEQ ID NO 243
<211> LENGTH: 21
<212> TYPE: DNA
<213> ORGANISM: Artificial Sequence
<220> FEATURE:
<223> OTHER INFORMATION: Influenza A Virus

<400> SEQUENCE: 243
aactgacagg attagattgc a                                21

<210> SEQ ID NO 244
<211> LENGTH: 21
<212> TYPE: DNA
<213> ORGANISM: Artificial Sequence
<220> FEATURE:
<223> OTHER INFORMATION: Influenza A Virus

<400> SEQUENCE: 244
aagaccttgt ttctgggttg a                                21

<210> SEQ ID NO 245
<211> LENGTH: 21
<212> TYPE: DNA
<213> ORGANISM: Artificial Sequence
<220> FEATURE:
<223> OTHER INFORMATION: Influenza A Virus

<400> SEQUENCE: 245
aatcagaggg cggcccaaag a                                21

<210> SEQ ID NO 246
<211> LENGTH: 21
<212> TYPE: DNA
<213> ORGANISM: Artificial Sequence
<220> FEATURE:
<223> OTHER INFORMATION: Influenza A Virus

<400> SEQUENCE: 246
aaggtctgat tgatgggtgg t 21

<210> SEQ ID NO 247
<211> LENGTH: 21
<212> TYPE: DNA
<213> ORGANISM: Artificial Sequence
<220> FEATURE:
<223> OTHER INFORMATION: Influenza A Virus

<400> SEQUENCE: 247
aatgcacaag gggagggaac t 21

<210> SEQ ID NO 248
<211> LENGTH: 21
<212> TYPE: DNA
<213> ORGANISM: Artificial Sequence
<220> FEATURE:
<223> OTHER INFORMATION: Influenza A Virus

<400> SEQUENCE: 248
aagcacccaa tcagcaattg a 21

<210> SEQ ID NO 249
<211> LENGTH: 21
<212> TYPE: DNA
<213> ORGANISM: Artificial Sequence

```
<220> FEATURE:
<223> OTHER INFORMATION: Influenza A Virus

<400> SEQUENCE: 249
aatagacaat gaattcactg a                                              21

<210> SEQ ID NO 250
<211> LENGTH: 21
<212> TYPE: DNA
<213> ORGANISM: Artificial Sequence
<220> FEATURE:
<223> OTHER INFORMATION: Influenza A Virus

<400> SEQUENCE: 250
aagcaaattg gcaatgtgat a                                              21

<210> SEQ ID NO 251
<211> LENGTH: 21
<212> TYPE: DNA
<213> ORGANISM: Artificial Sequence
<220> FEATURE:
<223> OTHER INFORMATION: Influenza A Virus

<400> SEQUENCE: 251
aattggacca gagattccat g                                              21

<210> SEQ ID NO 252
<211> LENGTH: 21
<212> TYPE: DNA
<213> ORGANISM: Artificial Sequence
<220> FEATURE:
<223> OTHER INFORMATION: Influenza A Virus

<400> SEQUENCE: 252
aagagacaac tgagagagaa t                                              21

<210> SEQ ID NO 253
<211> LENGTH: 21
<212> TYPE: DNA
<213> ORGANISM: Artificial Sequence
<220> FEATURE:
<223> OTHER INFORMATION: Influenza A Virus

<400> SEQUENCE: 253
aagatggcac tggttgcttc g                                              21

<210> SEQ ID NO 254
<211> LENGTH: 21
<212> TYPE: DNA
<213> ORGANISM: Artificial Sequence
<220> FEATURE:
<223> OTHER INFORMATION: Influenza A Virus

<400> SEQUENCE: 254
aacacctatg atcacagcaa g                                              21

<210> SEQ ID NO 255
<211> LENGTH: 21
<212> TYPE: DNA
<213> ORGANISM: Artificial Sequence
<220> FEATURE:
<223> OTHER INFORMATION: Influenza A Virus

<400> SEQUENCE: 255
aatagaatac agattgaccc a                                              21
```

```
<210> SEQ ID NO 256
<211> LENGTH: 21
<212> TYPE: DNA
<213> ORGANISM: Artificial Sequence
<220> FEATURE:
<223> OTHER INFORMATION: Influenza A Virus
<220> FEATURE:
<221> NAME/KEY: misc-feature
<220> FEATURE:
<221> NAME/KEY: (1)...(21)
<223> OTHER INFORMATION: combined DNA/RNA molecule

<400> SEQUENCE: 256
ggaucuuauu ucuucggagt t                                              21

<210> SEQ ID NO 257
<211> LENGTH: 21
<212> TYPE: DNA
<213> ORGANISM: Artificial Sequence
<220> FEATURE:
<223> OTHER INFORMATION: Influenza A Virus
<220> FEATURE:
<221> NAME/KEY: misc-feature
<220> FEATURE:
<221> NAME/KEY: (1)...(21)
<223> OTHER INFORMATION: combined DNA/RNA molecule

<400> SEQUENCE: 257
cuccgaagaa auaagaucct t                                              21

<210> SEQ ID NO 258
<211> LENGTH: 21
<212> TYPE: DNA
<213> ORGANISM: Artificial Sequence
<220> FEATURE:
<223> OTHER INFORMATION: Influenza A Virus
<220> FEATURE:
<221> NAME/KEY: misc-feature
<220> FEATURE:
<221> NAME/KEY: (1)...(21)
<223> OTHER INFORMATION: combined DNA/RNA molecule

<400> SEQUENCE: 258
uaugagagaa ugugcaacat t                                              21

<210> SEQ ID NO 259
<211> LENGTH: 21
<212> TYPE: DNA
<213> ORGANISM: Artificial Sequence
<220> FEATURE:
<223> OTHER INFORMATION: Influenza A Virus
<220> FEATURE:
<221> NAME/KEY: misc-feature
<220> FEATURE:
<221> NAME/KEY: (1)...(21)
<223> OTHER INFORMATION: combined DNA/RNA molecule

<400> SEQUENCE: 259
uguugcacau ucucucauat t                                              21

<210> SEQ ID NO 260
<211> LENGTH: 21
<212> TYPE: DNA
<213> ORGANISM: Artificial Sequence
<220> FEATURE:
<223> OTHER INFORMATION: Influenza A Virus
<220> FEATURE:
<221> NAME/KEY: misc-feature
<220> FEATURE:
<221> NAME/KEY: (1)...(21)
<223> OTHER INFORMATION: combined DNA/RNA molecule
```

```
<400> SEQUENCE: 260
acagcagaau gcuguggaut t                                              21

<210> SEQ ID NO 261
<211> LENGTH: 21
<212> TYPE: DNA
<213> ORGANISM: Artificial Sequence
<220> FEATURE:
<223> OTHER INFORMATION: Influenza A Virus
<220> FEATURE:
<221> NAME/KEY: misc-feature
<220> FEATURE:
<221> NAME/KEY: (1)...(21)
<223> OTHER INFORMATION: combined DNA/RNA molecule

<400> SEQUENCE: 261
auccacagca uucugcugut t                                              21

<210> SEQ ID NO 262
<211> LENGTH: 21
<212> TYPE: DNA
<213> ORGANISM: Artificial Sequence
<220> FEATURE:
<223> OTHER INFORMATION: Influenza A Virus
<220> FEATURE:
<221> NAME/KEY: misc-feature
<220> FEATURE:
<221> NAME/KEY: (1)...(21)
<223> OTHER INFORMATION: combined DNA/RNA molecule

<400> SEQUENCE: 262
cugagucuau gagggaagat t                                              21

<210> SEQ ID NO 263
<211> LENGTH: 21
<212> TYPE: DNA
<213> ORGANISM: Artificial Sequence
<220> FEATURE:
<223> OTHER INFORMATION: Influenza A Virus
<220> FEATURE:
<221> NAME/KEY: misc-feature
<220> FEATURE:
<221> NAME/KEY: (1)...(21)
<223> OTHER INFORMATION: combined DNA/RNA molecule

<400> SEQUENCE: 263
ucuucccuca uagacucagt t                                              21

<210> SEQ ID NO 264
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 264
cctaatggtc tactagatga c                                              21

<210> SEQ ID NO 265
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 265
tgtgtgttat gatgtctctg g                                              21
```

-continued

<210> SEQ ID NO 266
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 266
gacatacaag agtatgacct c                                              21

<210> SEQ ID NO 267
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 267
atccgcatct taagcctaag c                                              21

<210> SEQ ID NO 268
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 268
aggctatctt agtgctctga g                                              21

<210> SEQ ID NO 269
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 269
gataagctga ctagagcctt g                                              21

<210> SEQ ID NO 270
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 270
gaaaggacct gggacactct c                                              21

<210> SEQ ID NO 271
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 271
atggttggct cttctgtggg c                                              21

<210> SEQ ID NO 272
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 272
ttgctcctga attccatgga g 21

<210> SEQ ID NO 273
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 273
gccactacta atgtgtgaag c 21

<210> SEQ ID NO 274
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 274
caagcagtga agtgtgccct g 21

<210> SEQ ID NO 275
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 275
ctccctactt tgtgcagtag c 21

<210> SEQ ID NO 276
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 276
agtgatgtaa aggtgtacgc c 21

<210> SEQ ID NO 277
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 277
tgctaaggct gatgtctttc c 21

<210> SEQ ID NO 278
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 278
atgtagtgca gttagcagag g 21

<210> SEQ ID NO 279
<211> LENGTH: 21
<212> TYPE: DNA
<213> ORGANISM: Artificial Sequence

```
<220> FEATURE:
<223> OTHER INFORMATION: Respiratory Syncytial Virus

<400> SEQUENCE: 279
gctctgttga tttactatgg g                                              21

<210> SEQ ID NO 280
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 280
acctctctca taattgcagc c                                              21

<210> SEQ ID NO 281
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 281
gtttgtgggt ttgatggttg g                                              21

<210> SEQ ID NO 282
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 282
aagggcaagt tcgcatcatc c                                              21

<210> SEQ ID NO 283
<211> LENGTH: 21
<212> TYPE: DNA
<213> ORGANISM: Artificial Sequence
<220> FEATURE:
<223> OTHER INFORMATION: Respiratory Syncytial Virus

<400> SEQUENCE: 283
ttcctaagtc ttgccatagc c                                              21

<210> SEQ ID NO 284
<211> LENGTH: 20
<212> TYPE: DNA
<213> ORGANISM: Artificial Sequence
<220> FEATURE:
<223> OTHER INFORMATION: Influenza A Virus

<400> SEQUENCE: 284
gaccaggagt ggaggaaaca                                                20

<210> SEQ ID NO 285
<211> LENGTH: 20
<212> TYPE: DNA
<213> ORGANISM: Artificial Sequence
<220> FEATURE:
<223> OTHER INFORMATION: Influenza A Virus

<400> SEQUENCE: 285 cggcccataat ggtcactctt                                               20
```

```
<210> SEQ ID NO 286
<211> LENGTH: 21
<212> TYPE: DNA
<213> ORGANISM: Artificial Sequence
<220> FEATURE:
<223> OTHER INFORMATION: Influenza A Virus

<400> SEQUENCE: 286
cgtcgcttta aatacggttt g                                        21

<210> SEQ ID NO 287
<211> LENGTH: 20
<212> TYPE: DNA
<213> ORGANISM: Artificial Sequence
<220> FEATURE:
<223> OTHER INFORMATION: Influenza A Virus

<400> SEQUENCE: 287
cgtcaacatc cacagcattc                                          20
```